US009185789B2

(12) United States Patent
Zwart et al.

(10) Patent No.: US 9,185,789 B2
(45) Date of Patent: Nov. 10, 2015

(54) MAGNETIC SHIMS TO ALTER MAGNETIC FIELDS

(71) Applicant: Mevion Medical Systems, Inc., Littleton, MA (US)

(72) Inventors: Gerrit Townsend Zwart, Durham, NH (US); Jan Van der Laan, Danvers, MA (US); Kenneth P. Gall, Harvard, MA (US); Stanislaw P. Sobczynski, Boxford, MA (US)

(73) Assignee: Mevion Medical Systems, Inc., Littleton, MA (US)

( * ) Notice: Subject to any disclaimer, the term of this patent is extended or adjusted under 35 U.S.C. 154(b) by 0 days.

(21) Appl. No.: 14/039,073

(22) Filed: Sep. 27, 2013

(65) Prior Publication Data

US 2014/0094371 A1    Apr. 3, 2014

Related U.S. Application Data

(60) Provisional application No. 61/707,548, filed on Sep. 28, 2012.

(51) Int. Cl.
*H05H 7/10* (2006.01)
*A61N 5/10* (2006.01)
*A61N 5/00* (2006.01)
(Continued)

(52) U.S. Cl.
CPC ............... *H05H 7/04* (2013.01); *A61N 5/1077* (2013.01); *H01F 6/06* (2013.01); *H05H 13/02* (2013.01); *A61N 2005/1087* (2013.01); *A61N 2005/1095* (2013.01)

(58) Field of Classification Search
CPC .. H05H 7/12; H01J 37/32623; H01J 37/3266; A61N 2005/1095; A61N 5/1077
USPC ................. 250/505.1, 492.1, 492.3; 315/500, 315/111.41, 111.61; 335/209
See application file for complete search history.

(56) References Cited

U.S. PATENT DOCUMENTS 2,280,606 A    4/1942  Van et al.
2,492,324 A    12/1949 Salisbury
(Continued)

FOREIGN PATENT DOCUMENTS

CA    2629333    5/2007
CN    1377521    10/2002
(Continued)

OTHER PUBLICATIONS

International Search Report and Written Opinion mailed May 26, 2014 from corresponding PCT application No. PCT/US2013/062117 (14 pages).
(Continued)

*Primary Examiner* — Nikita Wells
(74) *Attorney, Agent, or Firm* — Fish & Richardson P.C.

(57) ABSTRACT

An example particle accelerator includes a coil to provide a magnetic field to a cavity; a cryostat comprising a chamber for holding the coil, where the coil is arranged in the chamber to define an interior region of the coil and an exterior region of the coil; magnetic structures adjacent to the cryostat, where the magnetic structures have one or more slots at least partway therethrough; and one or more magnetic shims in one or more corresponding slots. The one or more magnetic shims are movable to adjust a position of the coil by changing a magnetic field produced by the magnetic structures.

35 Claims, 19 Drawing Sheets

(51) Int. Cl.
  *H05H 7/04* (2006.01)
  *H01F 6/06* (2006.01)
  *H05H 13/02* (2006.01)

(56) References Cited

U.S. PATENT DOCUMENTS

| | | | |
|---|---|---|---|
| 2,615,129 A | 10/1952 | McMillan |
| 2,616,042 A | 10/1952 | Weeks |
| 2,659,000 A | 11/1953 | Salisbury |
| 2,701,304 A | 2/1955 | Dickinson |
| 2,789,222 A | 4/1957 | Martin |
| 2,812,463 A | 11/1957 | Teng et al. |
| 3,024,379 A | 3/1962 | Verster |
| 3,175,131 A | 3/1965 | Burleigh et al. |
| 3,432,721 A | 3/1969 | Naydan et al. |
| 3,582,650 A | 6/1971 | Avery |
| 3,679,899 A | 7/1972 | Dimeff |
| 3,689,847 A | 9/1972 | Verster |
| 3,757,118 A | 9/1973 | Hodge et al. |
| 3,868,522 A | 2/1975 | Bigham et al. |
| 3,886,367 A | 5/1975 | Castle |
| 3,925,676 A | 12/1975 | Bigham et al. |
| 2,958,327 A | 5/1976 | Marancik et al. |
| 3,955,089 A | 5/1976 | McIntyre et al. |
| 3,958,327 A | 5/1976 | Marancik et al. |
| 3,992,625 A | 11/1976 | Schmidt et al. |
| 4,038,622 A | 7/1977 | Purcell |
| 4,047,068 A | 9/1977 | Ress et al. |
| 4,112,306 A | 9/1978 | Nunan |
| 4,129,784 A | 12/1978 | Tschunt et al. |
| 4,139,777 A | 2/1979 | Rautenbach |
| 4,197,510 A | 4/1980 | Szu |
| 4,220,866 A | 9/1980 | Symmons et al. |
| 4,230,129 A | 10/1980 | LeVeen |
| 4,256,966 A | 3/1981 | Heinz |
| 4,293,772 A | 10/1981 | Stieber |
| 4,336,505 A | 6/1982 | Meyer |
| 4,342,060 A | 7/1982 | Gibson |
| 4,345,210 A | 8/1982 | Tran |
| 4,353,033 A | 10/1982 | Karasawa |
| 4,425,506 A | 1/1984 | Brown et al. |
| 4,490,616 A | 12/1984 | Cipollina et al. |
| 4,507,614 A | 3/1985 | Prono et al. |
| 4,507,616 A | 3/1985 | Blosser et al. |
| 4,589,126 A | 5/1986 | Augustsson et al. |
| 4,598,208 A | 7/1986 | Brunelli et al. |
| 4,628,523 A | 12/1986 | Heflin |
| 4,633,125 A | 12/1986 | Blosser et al. |
| 4,641,057 A | 2/1987 | Blosser et al. |
| 4,641,104 A | 2/1987 | Blosser et al. |
| 4,651,007 A | 3/1987 | Perusek et al. |
| 4,680,565 A | 7/1987 | Jahnke |
| 4,705,955 A | 11/1987 | Mileikowsky |
| 4,710,722 A | 12/1987 | Jahnke |
| 4,726,046 A | 2/1988 | Nunan |
| 4,734,653 A | 3/1988 | Jahnke |
| 4,736,173 A | 4/1988 | Blosser et al. |
| 4,737,727 A | 4/1988 | Yamada et al. |
| 4,739,173 A | 4/1988 | Blosser et al. |
| 4,745,367 A | 5/1988 | Dustmann et al. |
| 4,754,147 A | 6/1988 | Maughan et al. |
| 4,763,483 A | 8/1988 | Olsen |
| 4,767,930 A | 8/1988 | Stieber et al. |
| 4,769,623 A | 9/1988 | Marsing et al. |
| 4,771,208 A | 9/1988 | Jongen et al. |
| 4,783,634 A | 11/1988 | Yamamoto et al. |
| 4,808,941 A | 2/1989 | Marsing |
| 4,812,658 A | 3/1989 | Koehler |
| 4,843,333 A | 6/1989 | Marsing et al. |
| 4,845,371 A | 7/1989 | Stieber |
| 4,865,284 A | 9/1989 | Gosis et al. |
| 4,868,843 A | 9/1989 | Nunan |
| 4,868,844 A | 9/1989 | Nunan |
| 4,870,287 A | 9/1989 | Cole et al. |
| 4,880,985 A | 11/1989 | Jones |
| 4,894,541 A | 1/1990 | Ono |
| 4,896,206 A | 1/1990 | Denham |
| 4,902,993 A | 2/1990 | Krevent |
| 4,904,949 A | 2/1990 | Wilson |
| 4,905,267 A | 2/1990 | Miller et al. |
| 4,917,344 A | 4/1990 | Prechter et al. |
| 4,943,781 A | 7/1990 | Wilson et al. |
| 4,945,478 A | 7/1990 | Merickel et al. |
| 4,968,915 A | 11/1990 | Wilson et al. |
| 4,987,309 A | 1/1991 | Klasen et al. |
| 4,992,744 A | 2/1991 | Fujita et al. |
| 4,996,496 A | 2/1991 | Kitamura et al. |
| 5,006,759 A | 4/1991 | Krispel |
| 5,010,562 A | 4/1991 | Hernandez et al. |
| 5,012,111 A | 4/1991 | Ueda |
| 5,017,789 A | 5/1991 | Young et al. |
| 5,017,882 A | 5/1991 | Finlan |
| 5,036,290 A | 7/1991 | Sonobe et al. |
| 5,039,057 A | 8/1991 | Prechter et al. |
| 5,039,867 A | 8/1991 | Nishihara et al. |
| 5,046,078 A | 9/1991 | Hernandez et al. |
| 5,072,123 A | 12/1991 | Johnsen |
| 5,111,042 A | 5/1992 | Sullivan et al. |
| 5,111,173 A | 5/1992 | Matsuda et al. |
| 5,117,194 A | 5/1992 | Nakanishi et al. |
| 5,117,212 A | 5/1992 | Yamamoto et al. |
| 5,117,829 A | 6/1992 | Miller et al. |
| 5,148,032 A | 9/1992 | Hernandez |
| 5,166,531 A | 11/1992 | Huntzinger |
| 5,189,687 A | 2/1993 | Bova et al. |
| 5,191,706 A | 3/1993 | Cosden |
| 5,240,218 A | 8/1993 | Dye |
| 5,260,579 A | 11/1993 | Yasuda et al. |
| 5,260,581 A | 11/1993 | Lesyna et al. |
| 5,278,533 A | 1/1994 | Kawaguchi |
| 5,285,166 A | 2/1994 | Hiramoto et al. |
| 5,317,164 A | 5/1994 | Kurokawa |
| 5,336,891 A | 8/1994 | Crewe |
| 5,341,104 A | 8/1994 | Anton et al. |
| 5,349,198 A | 9/1994 | Takanaka |
| 5,365,742 A | 11/1994 | Boffito et al. |
| 5,374,913 A | 12/1994 | Pissantezky et al. |
| 5,382,914 A | 1/1995 | Hamm et al. |
| 5,401,973 A | 3/1995 | McKeown et al. |
| 5,405,235 A | 4/1995 | Lebre et al. |
| 5,434,420 A | 7/1995 | McKeown et al. |
| 5,440,133 A | 8/1995 | Moyers et al. |
| 5,451,794 A | 9/1995 | McKeown et al. |
| 5,461,773 A | 10/1995 | Kawaguchi |
| 5,463,291 A | 10/1995 | Carroll et al. |
| 5,464,411 A | 11/1995 | Schulte et al. |
| 5,492,922 A | 2/1996 | Palkowitz |
| 5,511,549 A | 4/1996 | Legg et al. |
| 5,521,469 A | 5/1996 | Laisne |
| 5,538,942 A | 7/1996 | Koyama et al. |
| 5,549,616 A | 8/1996 | Schulte et al. |
| 5,561,697 A | 10/1996 | Takafuji et al. |
| 5,585,642 A | 12/1996 | Britton et al. |
| 5,633,747 A | 5/1997 | Nikoonahad |
| 5,635,721 A | 6/1997 | Bardi et al. |
| 5,668,371 A | 9/1997 | Deasy et al. |
| 5,672,878 A | 9/1997 | Yao |
| 5,691,679 A | 11/1997 | Ackermann et al. |
| 5,726,448 A | 3/1998 | Smith et al. |
| 5,727,554 A | 3/1998 | Kalend et al. |
| 5,730,745 A | 3/1998 | Schulte et al. |
| 5,751,781 A | 5/1998 | Brown et al. |
| 5,778,047 A | 7/1998 | Mansfield et al. |
| 5,783,914 A | 7/1998 | Hiramoto et al. |
| 5,784,431 A | 7/1998 | Kalend et al. |
| 5,797,924 A | 8/1998 | Schulte et al. |
| 5,811,944 A | 9/1998 | Sampayan et al. |
| 5,818,058 A | 10/1998 | Nakanishi et al. |
| 5,821,705 A | 10/1998 | Caporasco et al. |
| 5,825,845 A | 10/1998 | Blair et al. |
| 5,841,237 A | 11/1998 | Alton |
| 5,846,043 A | 12/1998 | Spath |
| 5,851,182 A | 12/1998 | Sahadevan |
| 5,866,912 A | 2/1999 | Slater et al. |

(56) References Cited

U.S. PATENT DOCUMENTS

| | | |
|---|---|---|
| 5,874,811 A | 2/1999 | Finlan et al. |
| 5,895,926 A | 4/1999 | Britton et al. |
| 5,920,601 A | 7/1999 | Nigg et al. |
| 5,929,458 A | 7/1999 | Nemezawa et al. |
| 5,963,615 A | 10/1999 | Egley et al. |
| 5,993,373 A | 11/1999 | Nonaka et al. |
| 6,008,499 A | 12/1999 | Hiramoto et al. |
| 6,034,377 A | 3/2000 | Pu |
| 6,057,655 A | 5/2000 | Jongen |
| 6,061,426 A | 5/2000 | Linders et al. |
| 6,064,807 A | 5/2000 | Arai et al. |
| 6,066,851 A | 5/2000 | Madono et al. |
| 6,080,992 A | 6/2000 | Nonaka et al. |
| 6,087,670 A | 7/2000 | Hiramoto et al. |
| 6,094,760 A | 8/2000 | Nonaka et al. |
| 6,118,848 A | 9/2000 | Reiffel |
| 6,140,021 A | 10/2000 | Nakasuji et al. |
| 6,144,875 A | 11/2000 | Schweikard et al. |
| 6,158,708 A | 12/2000 | Egley et al. |
| 6,207,952 B1 | 3/2001 | Kan et al. |
| 6,219,403 B1 | 4/2001 | Nishihara |
| 6,222,905 B1 | 4/2001 | Yoda et al. |
| 6,241,671 B1 | 6/2001 | Ritter et al. |
| 6,246,066 B1 | 6/2001 | Yuehu |
| 6,256,591 B1 | 7/2001 | Yoda et al. |
| 6,265,837 B1 | 7/2001 | Akiyama et al. |
| 6,268,610 B1 | 7/2001 | Pu |
| 6,278,239 B1 | 8/2001 | Caporaso et al. |
| 6,279,579 B1 | 8/2001 | Riaziat et al. |
| 6,307,914 B1 | 10/2001 | Kunieda et al. |
| 6,316,776 B1 | 11/2001 | Hiramoto et al. |
| 6,366,021 B1 | 4/2002 | Meddaugh et al. |
| 6,369,585 B2 | 4/2002 | Yao |
| 6,380,545 B1 | 4/2002 | Yan |
| 6,407,505 B1 | 6/2002 | Bertsche |
| 6,417,634 B1 | 7/2002 | Bergstrom |
| 6,433,336 B1 | 8/2002 | Jongen et al. |
| 6,433,349 B2 | 8/2002 | Akiyama et al. |
| 6,433,494 B1 | 8/2002 | Kulish et al. |
| 6,441,569 B1 | 8/2002 | Janzow |
| 6,443,349 B1 | 9/2002 | Van Der Burg |
| 6,465,957 B1 | 10/2002 | Whitham et al. |
| 6,472,834 B2 | 10/2002 | Hiramoto et al. |
| 6,476,403 B1 | 11/2002 | Dolinskii et al. |
| 6,492,922 B1 | 12/2002 | New |
| 6,493,424 B2 | 12/2002 | Whitham |
| 6,498,444 B1 | 12/2002 | Hanna et al. |
| 6,501,981 B1 | 12/2002 | Schweikard et al. |
| 6,519,316 B1 | 2/2003 | Collins |
| 6,593,696 B2 | 7/2003 | Ding et al. |
| 6,594,336 B2 | 7/2003 | Nishizawa et al. |
| 6,600,164 B1 | 7/2003 | Badura et al. |
| 6,617,598 B1 | 9/2003 | Matsuda |
| 6,621,889 B1 | 9/2003 | Mostafavi |
| 6,639,234 B1 | 10/2003 | Badura et al. |
| 6,646,383 B2 | 11/2003 | Bertsche et al. |
| 6,670,618 B1 | 12/2003 | Hartmann et al. |
| 6,683,318 B1 | 1/2004 | Haberer et al. |
| 6,683,426 B1 | 1/2004 | Kleeven |
| 6,693,283 B2 | 2/2004 | Eickhoff et al. |
| 6,710,362 B2 | 3/2004 | Kraft et al. |
| 6,713,773 B1 | 3/2004 | Lyons et al. |
| 6,713,976 B1 | 3/2004 | Zumoto et al. |
| 6,717,162 B1 | 4/2004 | Jongen |
| 6,736,831 B1 | 5/2004 | Hartmann et al. |
| 6,745,072 B1 | 6/2004 | Badura et al. |
| 6,769,806 B2 | 8/2004 | Moyers |
| 6,774,383 B2 | 8/2004 | Norimine et al. |
| 6,777,689 B2 | 8/2004 | Nelson |
| 6,777,700 B2 | 8/2004 | Yanagisawa et al. |
| 6,780,149 B1 | 8/2004 | Schulte |
| 6,794,868 B1 * | 9/2004 | Wong et al. ............... 324/307 |
| 6,799,068 B1 | 9/2004 | Hartmann et al. |
| 6,800,866 B2 | 10/2004 | Amemiya et al. |
| 6,803,591 B2 | 10/2004 | Muramatsu et al. |
| 6,814,694 B1 | 11/2004 | Pedroni |
| 6,822,244 B2 | 11/2004 | Beloussov et al. |
| 6,853,142 B2 | 2/2005 | Chistyakov |
| 6,853,703 B2 | 2/2005 | Svatos et al. |
| 6,864,770 B2 | 3/2005 | Nemoto et al. |
| 6,865,254 B2 | 3/2005 | Nafstadius |
| 6,873,123 B2 | 3/2005 | Marchand et al. |
| 6,891,177 B1 | 5/2005 | Kraft et al. |
| 6,891,924 B1 | 5/2005 | Yoda et al. |
| 6,894,300 B2 | 5/2005 | Reimoser et al. |
| 6,897,451 B2 | 5/2005 | Kaercher et al. |
| 6,914,396 B1 | 7/2005 | Symons et al. |
| 6,936,832 B2 | 8/2005 | Norimine et al. |
| 6,953,943 B2 | 10/2005 | Yanagisawa et al. |
| 6,965,116 B1 | 11/2005 | Wagner et al. |
| 6,969,194 B1 | 11/2005 | Nafstadius |
| 6,979,832 B2 | 12/2005 | Yanagisawa et al. |
| 6,984,835 B2 | 1/2006 | Harada |
| 6,992,312 B2 | 1/2006 | Yanagisawa et al. |
| 6,993,112 B2 | 1/2006 | Hesse |
| 7,008,105 B2 | 3/2006 | Amann et al. |
| 7,011,447 B2 | 3/2006 | Moyers |
| 7,012,267 B2 | 3/2006 | Moriyama et al. |
| 7,014,361 B1 | 3/2006 | Ein-Gal |
| 7,026,636 B2 | 4/2006 | Yanagisawa et al. |
| 7,038,403 B2 | 5/2006 | Mastrangeli et al. |
| 7,041,479 B2 | 5/2006 | Swartz et al. |
| 7,045,781 B2 | 5/2006 | Adamec et al. |
| 7,049,613 B2 | 5/2006 | Yanagisawa et al. |
| 7,053,389 B2 | 5/2006 | Yanagisawa et al. |
| 7,054,801 B2 | 5/2006 | Sakamoto et al. |
| 7,060,997 B2 | 6/2006 | Norimine et al. |
| 7,071,479 B2 | 7/2006 | Yanagisawa et al. |
| 7,073,508 B2 | 7/2006 | Moyers |
| 7,081,619 B2 | 7/2006 | Bashkirov et al. |
| 7,084,410 B2 | 8/2006 | Beloussov et al. |
| 7,091,478 B2 | 8/2006 | Haberer |
| 7,102,144 B2 | 9/2006 | Matsuda et al. |
| 7,122,811 B2 | 10/2006 | Matsuda et al. |
| 7,122,966 B2 | 10/2006 | Norling et al. |
| 7,122,978 B2 | 10/2006 | Nakanishi et al. |
| 7,135,678 B2 | 11/2006 | Wang et al. |
| 7,138,771 B2 | 11/2006 | Bechthold et al. |
| 7,154,107 B2 | 12/2006 | Yanagisawa et al. |
| 7,154,108 B2 | 12/2006 | Tadokoro et al. |
| 7,154,991 B2 | 12/2006 | Earnst et al. |
| 7,162,005 B2 | 1/2007 | Bjorkholm |
| 7,173,264 B2 | 2/2007 | Moriyama et al. |
| 7,173,265 B2 | 2/2007 | Miller et al. |
| 7,173,385 B2 | 2/2007 | Caporaso et al. |
| 7,186,991 B2 | 3/2007 | Kato et al. |
| 7,193,227 B2 | 3/2007 | Hiramoto et al. |
| 7,199,382 B2 | 4/2007 | Rigney et al. |
| 7,208,748 B2 | 4/2007 | Sliski et al. |
| 7,212,608 B2 | 5/2007 | Nagamine et al. |
| 7,212,609 B2 | 5/2007 | Nagamine et al. |
| 7,221,733 B1 | 5/2007 | Takai et al. |
| 7,227,161 B2 | 6/2007 | Matsuda et al. |
| 7,247,869 B2 | 7/2007 | Tadokoro et al. |
| 7,257,191 B2 | 8/2007 | Sommer |
| 7,259,529 B2 | 8/2007 | Tanaka |
| 7,262,424 B2 | 8/2007 | Moriyama et al. |
| 7,262,565 B2 | 8/2007 | Fujisawa |
| 7,274,018 B2 | 9/2007 | Adamec et al. |
| 7,280,633 B2 | 10/2007 | Cheng et al. |
| 7,295,649 B2 | 11/2007 | Johnsen |
| 7,297,967 B2 | 11/2007 | Yanagisawa et al. |
| 7,301,162 B2 | 11/2007 | Matsuda et al. |
| 7,307,264 B2 | 12/2007 | Brusasco et al. |
| 7,318,805 B2 | 1/2008 | Schweikard et al. |
| 7,319,231 B2 | 1/2008 | Moriyama et al. |
| 7,319,336 B2 | 1/2008 | Baur et al. |
| 7,331,713 B2 | 2/2008 | Moyers |
| 7,332,880 B2 | 2/2008 | Ina et al. |
| 7,345,291 B2 | 3/2008 | Kats |
| 7,345,292 B2 | 3/2008 | Moriyama et al. |
| 7,348,557 B2 | 3/2008 | Armit |
| 7,348,579 B2 | 3/2008 | Pedroni |
| 7,351,988 B2 | 4/2008 | Naumann et al. |

(56) References Cited

U.S. PATENT DOCUMENTS

| | | |
|---|---|---|
| 7,355,189 B2 | 4/2008 | Yanagisawa et al. |
| 7,368,740 B2 | 5/2008 | Beloussov et al. |
| 7,372,053 B2 | 5/2008 | Yamashita et al. |
| 7,378,672 B2 | 5/2008 | Harada |
| 7,381,979 B2 | 6/2008 | Yamashita et al. |
| 7,397,054 B2 | 7/2008 | Natori et al. |
| 7,397,901 B1 | 7/2008 | Johnsen |
| 7,398,309 B2 | 7/2008 | Baumann et al. |
| 7,402,822 B2 | 7/2008 | Guertin et al. |
| 7,402,823 B2 | 7/2008 | Guertin et al. |
| 7,402,824 B2 | 7/2008 | Guertin et al. |
| 7,402,963 B2 | 7/2008 | Sliski |
| 7,405,407 B2 | 7/2008 | Hiramoto et al. |
| 7,425,717 B2 | 9/2008 | Matsuda et al. |
| 7,432,516 B2 | 10/2008 | Peggs et al. |
| 7,439,528 B2 | 10/2008 | Nishiuchi et al. |
| 7,446,328 B2 | 11/2008 | Rigney et al. |
| 7,446,490 B2 | 11/2008 | Jongen et al. |
| 7,449,701 B2 | 11/2008 | Fujimaki et al. |
| 7,453,076 B2 | 11/2008 | Welch et al. |
| 7,465,944 B2 | 12/2008 | Ueno et al. |
| 7,466,085 B2 | 12/2008 | Nutt |
| 7,468,506 B2 | 12/2008 | Rogers et al. |
| 7,473,913 B2 | 1/2009 | Hermann et al. |
| 7,476,867 B2 | 1/2009 | Fritsch et al. |
| 7,476,883 B2 | 1/2009 | Nutt |
| 7,482,606 B2 | 1/2009 | Groezinger et al. |
| 7,492,556 B2 | 2/2009 | Atkins et al. |
| 7,507,975 B2 | 3/2009 | Mohr |
| 7,525,104 B2 | 4/2009 | Harada |
| 7,541,905 B2 | 6/2009 | Antaya |
| 7,547,901 B2 | 6/2009 | Guertin et al. |
| 7,554,096 B2 | 6/2009 | Ward et al. |
| 7,554,097 B2 | 6/2009 | Ward et al. |
| 7,555,103 B2 | 6/2009 | Johnsen |
| 7,557,358 B2 | 7/2009 | Ward et al. |
| 7,557,359 B2 | 7/2009 | Ward et al. |
| 7,557,360 B2 | 7/2009 | Ward et al. |
| 7,557,361 B2 | 7/2009 | Ward et al. |
| 7,560,715 B2 | 7/2009 | Pedroni |
| 7,560,717 B2 | 7/2009 | Matsuda et al. |
| 7,567,694 B2 | 7/2009 | Lu et al. |
| 7,574,251 B2 | 8/2009 | Lu et al. |
| 7,576,499 B2 | 8/2009 | Caporaso et al. |
| 7,579,603 B2 | 8/2009 | Birgy et al. |
| 7,579,610 B2 | 8/2009 | Grozinger et al. |
| 7,582,866 B2 | 9/2009 | Furuhashi et al. |
| 7,582,885 B2 | 9/2009 | Katagiri et al. |
| 7,582,886 B2 | 9/2009 | Trbojevic |
| 7,586,112 B2 | 9/2009 | Chiba et al. |
| 7,598,497 B2 | 10/2009 | Yamamoto et al. |
| 7,609,009 B2 | 10/2009 | Tanaka et al. |
| 7,609,809 B2 | 10/2009 | Kapatoes et al. |
| 7,609,811 B1 | 10/2009 | Siljamaki et al. |
| 7,615,942 B2 | 11/2009 | Sanders et al. |
| 7,626,347 B2 | 12/2009 | Sliski |
| 7,629,598 B2 | 12/2009 | Harada |
| 7,639,853 B2 | 12/2009 | Olivera et al. |
| 7,639,854 B2 | 12/2009 | Schnarr et al. |
| 7,643,661 B2 | 1/2010 | Ruchala et al. |
| 7,656,258 B1 | 2/2010 | Antaya et al. |
| 7,659,521 B2 | 2/2010 | Pedroni |
| 7,659,528 B2 | 2/2010 | Uematsu |
| 7,668,291 B2 | 2/2010 | Nord et al. |
| 7,672,429 B2 | 3/2010 | Urano et al. |
| 7,679,073 B2 | 3/2010 | Urano et al. |
| 7,682,078 B2 | 3/2010 | Rietzel |
| 7,692,166 B2 | 4/2010 | Muraki et al. |
| 7,692,168 B2 | 4/2010 | Moriyama et al. |
| 7,696,499 B2 | 4/2010 | Miller et al. |
| 7,696,847 B2 | 4/2010 | Antaya |
| 7,701,677 B2 | 4/2010 | Schultz et al. |
| 7,709,818 B2 | 5/2010 | Matsuda et al. |
| 7,710,051 B2 | 5/2010 | Caporaso et al. |
| 7,718,982 B2 | 5/2010 | Sliski |
| 7,728,311 B2 | 6/2010 | Gall |
| 7,746,978 B2 | 6/2010 | Cheng et al. |
| 7,755,305 B2 | 7/2010 | Umezawa et al. |
| 7,759,642 B2 | 7/2010 | Nir |
| 7,763,867 B2 | 7/2010 | Birgy et al. |
| 7,767,988 B2 | 8/2010 | Kaiser et al. |
| 7,770,231 B2 | 8/2010 | Prater et al. |
| 7,772,577 B2 | 8/2010 | Saito et al. |
| 7,773,723 B2 | 8/2010 | Nord et al. |
| 7,773,788 B2 | 8/2010 | Lu et al. |
| 7,778,488 B2 | 8/2010 | Nord et al. |
| 7,783,010 B2 | 8/2010 | Clayton |
| 7,784,127 B2 | 8/2010 | Kuro et al. |
| 7,786,451 B2 | 8/2010 | Ward et al. |
| 7,786,452 B2 | 8/2010 | Ward et al. |
| 7,789,560 B2 | 9/2010 | Moyers |
| 7,791,051 B2 | 9/2010 | Beloussov et al. |
| 7,796,731 B2 | 9/2010 | Nord et al. |
| 7,801,269 B2 | 9/2010 | Cravens et al. |
| 7,801,270 B2 | 9/2010 | Nord et al. |
| 7,801,988 B2 | 9/2010 | Baumann et al. |
| 7,807,982 B2 | 10/2010 | Nishiuchi et al. |
| 7,809,107 B2 | 10/2010 | Nord et al. |
| 7,812,319 B2 | 10/2010 | Diehl et al. |
| 7,812,326 B2 | 10/2010 | Grozinger et al. |
| 7,816,657 B2 | 10/2010 | Hansmann et al. |
| 7,817,778 B2 | 10/2010 | Nord et al. |
| 7,817,836 B2 | 10/2010 | Chao et al. |
| 7,834,334 B2 | 11/2010 | Grozinger et al. |
| 7,834,336 B2 | 11/2010 | Boeh et al. |
| 7,835,494 B2 | 11/2010 | Nord et al. |
| 7,835,502 B2 | 11/2010 | Spence et al. |
| 7,839,972 B2 | 11/2010 | Ruchala et al. |
| 7,839,973 B2 | 11/2010 | Nord et al. |
| 7,848,488 B2 | 12/2010 | Mansfield |
| 7,857,756 B2 | 12/2010 | Warren et al. |
| 7,860,216 B2 | 12/2010 | Jongen et al. |
| 7,860,550 B2 | 12/2010 | Saracen et al. |
| 7,868,301 B2 | 1/2011 | Diehl |
| 7,875,861 B2 | 1/2011 | Huttenberger et al. |
| 7,875,868 B2 | 1/2011 | Moriyama et al. |
| 7,881,431 B2 | 2/2011 | Aoi et al. |
| 7,894,574 B1 | 2/2011 | Nord et al. |
| 7,906,769 B2 | 3/2011 | Blasche et al. |
| 7,914,734 B2 | 3/2011 | Livingston |
| 7,919,765 B2 | 4/2011 | Timmer |
| 7,920,040 B2 | 4/2011 | Antaya et al. |
| 7,920,675 B2 | 4/2011 | Lomax et al. |
| 7,928,415 B2 | 4/2011 | Bert et al. |
| 7,934,869 B2 | 5/2011 | Ivanov et al. |
| 7,940,881 B2 | 5/2011 | Jongen et al. |
| 7,943,913 B2 | 5/2011 | Balakin |
| 7,947,969 B2 | 5/2011 | Pu |
| 7,949,096 B2 | 5/2011 | Cheng et al. |
| 7,950,587 B2 | 5/2011 | Henson et al. |
| 7,960,710 B2 | 6/2011 | Kruip et al. |
| 7,961,844 B2 | 6/2011 | Takeda et al. |
| 7,977,648 B2 | 7/2011 | Westerly et al. |
| 7,977,656 B2 | 7/2011 | Fujimaki et al. |
| 7,982,198 B2 | 7/2011 | Nishiuchi et al. |
| 7,982,416 B2 | 7/2011 | Tanaka et al. |
| 7,984,715 B2 | 7/2011 | Moyers |
| 7,986,768 B2 | 7/2011 | Nord et al. |
| 7,987,053 B2 | 7/2011 | Schaffner |
| 7,989,785 B2 | 8/2011 | Emhofer et al. |
| 7,990,524 B2 | 8/2011 | Jureller et al. |
| 7,997,553 B2 | 8/2011 | Sloan et al. |
| 8,002,466 B2 | 8/2011 | Von Neubeck et al. |
| 8,003,964 B2 | 8/2011 | Stark et al. |
| 8,009,803 B2 | 8/2011 | Nord et al. |
| 8,009,804 B2 | 8/2011 | Siljamaki et al. |
| 8,039,822 B2 | 10/2011 | Rietzel |
| 8,041,006 B2 | 10/2011 | Boyden et al. |
| 8,044,364 B2 | 10/2011 | Yamamoto |
| 8,049,187 B2 | 11/2011 | Tachikawa |
| 8,053,508 B2 | 11/2011 | Korkut et al. |
| 8,053,739 B2 | 11/2011 | Rietzel |
| 8,053,745 B2 | 11/2011 | Moore |
| 8,053,746 B2 | 11/2011 | Timmer et al. |

(56) References Cited

U.S. PATENT DOCUMENTS

| | | |
|---|---|---|
| 8,067,748 B2 | 11/2011 | Balakin |
| 8,069,675 B2 | 12/2011 | Radovinsky et al. |
| 8,071,966 B2 | 12/2011 | Kaiser et al. |
| 8,080,801 B2 | 12/2011 | Safai |
| 8,085,899 B2 | 12/2011 | Nord et al. |
| 8,089,054 B2 | 1/2012 | Balakin |
| 8,093,564 B2 | 1/2012 | Balakin |
| 8,093,568 B2 | 1/2012 | Mackie et al. |
| 8,111,125 B2 | 2/2012 | Antaya et al. |
| 8,129,699 B2 | 3/2012 | Balakin |
| 8,144,832 B2 | 3/2012 | Balakin |
| 8,173,981 B2 | 5/2012 | Trbojevic |
| 8,188,688 B2 | 5/2012 | Balakin |
| 8,198,607 B2 | 6/2012 | Balakin |
| 8,222,613 B2 | 7/2012 | Tajiri et al. |
| 8,227,768 B2 | 7/2012 | Smick et al. |
| 8,232,536 B2 | 7/2012 | Harada |
| 8,278,634 B2 | 10/2012 | Vanderberg et al. |
| 8,288,742 B2 | 10/2012 | Balakin |
| 8,291,717 B2 | 10/2012 | Radovinsky et al. |
| 8,294,127 B2 | 10/2012 | Tachibana |
| 8,304,725 B2 | 11/2012 | Komuro et al. |
| 8,304,750 B2 | 11/2012 | Preikszas et al. |
| 8,309,941 B2 | 11/2012 | Balakin |
| 8,330,132 B2 | 12/2012 | Guertin et al. |
| 8,334,520 B2 | 12/2012 | Otaka et al. |
| 8,335,397 B2 | 12/2012 | Takane et al. |
| 8,344,340 B2 | 1/2013 | Gall |
| 8,350,214 B2 | 1/2013 | Otaki et al. |
| 8,368,038 B2 | 2/2013 | Balakin |
| 8,368,043 B2 | 2/2013 | Havelange et al. |
| 8,373,143 B2 | 2/2013 | Balakin |
| 8,373,145 B2 * | 2/2013 | Balakin ............... 250/492.3 |
| 8,378,299 B2 | 2/2013 | Frosien |
| 8,378,321 B2 | 2/2013 | Balakin |
| 8,382,943 B2 | 2/2013 | Clark |
| 8,389,949 B2 | 3/2013 | Harada et al. |
| 8,399,866 B2 | 3/2013 | Balakin |
| 8,405,042 B2 | 3/2013 | Honda et al. |
| 8,405,056 B2 | 3/2013 | Amaldi et al. |
| 8,415,643 B2 | 4/2013 | Balakin |
| 8,416,918 B2 | 4/2013 | Nord et al. |
| 8,421,041 B2 | 4/2013 | Balakin |
| 8,426,833 B2 | 4/2013 | Trbojevic |
| 8,436,323 B2 | 5/2013 | Iseki et al. |
| 8,440,987 B2 | 5/2013 | Stephani et al. |
| 8,445,872 B2 | 5/2013 | Behrens et al. |
| 8,466,441 B2 | 6/2013 | Iwata et al. |
| 8,472,583 B2 | 6/2013 | Star-Lack et al. |
| 8,483,357 B2 | 7/2013 | Siljamaki et al. |
| 8,487,278 B2 | 7/2013 | Balakin |
| 8,502,173 B2 | 8/2013 | Vanderberg et al. |
| 8,552,406 B2 | 10/2013 | Phaneuf et al. |
| 8,552,408 B2 | 10/2013 | Hanawa et al. |
| 8,569,717 B2 | 10/2013 | Balakin |
| 8,581,215 B2 | 11/2013 | Balakin |
| 8,581,523 B2 | 11/2013 | Gall et al. |
| 8,581,525 B2 | 11/2013 | Antaya et al. |
| 8,653,314 B2 | 2/2014 | Pelati et al. |
| 8,653,473 B2 | 2/2014 | Yajima |
| 8,791,656 B1 | 7/2014 | Zwart et al. |
| 8,927,950 B2 | 1/2015 | Gall et al. |
| 2002/0172317 A1 | 11/2002 | Maksimchuk et al. |
| 2003/0048080 A1 | 3/2003 | Amemiya et al. |
| 2003/0125622 A1 | 7/2003 | Schweikard et al. |
| 2003/0136924 A1 | 7/2003 | Kraft et al. |
| 2003/0152197 A1 | 8/2003 | Moyers |
| 2003/0163015 A1 | 8/2003 | Yanagisawa et al. |
| 2003/0183779 A1 | 10/2003 | Norimine et al. |
| 2003/0234369 A1 | 12/2003 | Glukhoy |
| 2004/0000650 A1 | 1/2004 | Yanagisawa et al. |
| 2004/0017888 A1 | 1/2004 | Seppi et al. |
| 2004/0056212 A1 | 3/2004 | Yanagisawa et al. |
| 2004/0061077 A1 | 4/2004 | Muramatsu et al. |
| 2004/0061078 A1 | 4/2004 | Muramatsu et al. |
| 2004/0085023 A1 | 5/2004 | Chistyakov |
| 2004/0098445 A1 | 5/2004 | Baumann et al. |
| 2004/0111134 A1 | 6/2004 | Muramatsu et al. |
| 2004/0118081 A1 | 6/2004 | Reimoser et al. |
| 2004/0149934 A1 | 8/2004 | Yanagisawa et al. |
| 2004/0159795 A1 | 8/2004 | Kaercher et al. |
| 2004/0173763 A1 | 9/2004 | Moriyama et al. |
| 2004/0174958 A1 | 9/2004 | Moriyama et al. |
| 2004/0183033 A1 | 9/2004 | Moriyama et al. |
| 2004/0183035 A1 | 9/2004 | Yanagisawa et al. |
| 2004/0200982 A1 | 10/2004 | Moriyama et al. |
| 2004/0200983 A1 | 10/2004 | Fujimaki et al. |
| 2004/0213381 A1 | 10/2004 | Harada |
| 2004/0227104 A1 | 11/2004 | Matsuda et al. |
| 2004/0232356 A1 | 11/2004 | Norimine et al. |
| 2004/0240626 A1 | 12/2004 | Moyers |
| 2005/0058245 A1 | 3/2005 | Ein-Gal |
| 2005/0089141 A1 | 4/2005 | Brown |
| 2005/0161618 A1 | 7/2005 | Eros |
| 2005/0184686 A1 | 8/2005 | Caporasco et al. |
| 2005/0228255 A1 | 10/2005 | Saracen et al. |
| 2005/0234327 A1 | 10/2005 | Saracen et al. |
| 2005/0247890 A1 | 11/2005 | Norimine et al. |
| 2006/0017015 A1 | 1/2006 | Sliski et al. |
| 2006/0067468 A1 | 3/2006 | Rietzel |
| 2006/0126792 A1 | 6/2006 | Li |
| 2006/0145088 A1 | 7/2006 | Ma |
| 2006/0175991 A1 | 8/2006 | Fujisawa |
| 2006/0284562 A1 | 12/2006 | Hruby et al. |
| 2007/0001128 A1 | 1/2007 | Sliski et al. |
| 2007/0013273 A1 | 1/2007 | Albert et al. |
| 2007/0014654 A1 | 1/2007 | Haverfield et al. |
| 2007/0023699 A1 | 2/2007 | Yamashita et al. |
| 2007/0029510 A1 | 2/2007 | Hermann et al. |
| 2007/0051904 A1 | 3/2007 | Kaiser et al. |
| 2007/0092812 A1 | 4/2007 | Caporasco et al. |
| 2007/0114945 A1 | 5/2007 | Mattaboni et al. |
| 2007/0145916 A1 | 6/2007 | Caporasco et al. |
| 2007/0171015 A1 | 7/2007 | Antaya |
| 2007/0181519 A1 | 8/2007 | Khoshnevis |
| 2007/0284548 A1 | 12/2007 | Kaiser et al. |
| 2008/0093567 A1 | 4/2008 | Gall |
| 2008/0218102 A1 | 9/2008 | Sliski |
| 2009/0096179 A1 | 4/2009 | Stark et al. |
| 2009/0140671 A1 | 6/2009 | O'Neal et al. |
| 2009/0140672 A1 | 6/2009 | Gall et al. |
| 2009/0200483 A1 | 8/2009 | Gall et al. |
| 2010/0045213 A1 | 2/2010 | Sliski et al. |
| 2010/0230617 A1 | 9/2010 | Gall |
| 2010/0308235 A1 | 12/2010 | Sliski |
| 2011/0299919 A1 | 12/2011 | Stark |
| 2013/0053616 A1 | 2/2013 | Gall |
| 2013/0127375 A1 | 5/2013 | Sliski |
| 2013/0131424 A1 | 5/2013 | Sliski |
| 2013/0237425 A1 | 9/2013 | Leigh et al. |
| 2013/0249443 A1 | 9/2013 | Antaya et al. |
| 2014/0028220 A1 | 1/2014 | Bromberg et al. |
| 2014/0042934 A1 | 2/2014 | Hiroshi |
| 2014/0091734 A1 | 4/2014 | Gall et al. |
| 2014/0094371 A1 | 4/2014 | Zwart et al. |
| 2014/0094637 A1 * | 4/2014 | Zwart et al. ............... 600/1 |
| 2014/0094638 A1 | 4/2014 | Gall et al. |
| 2014/0094639 A1 * | 4/2014 | Zwart et al. ............... 600/1 |
| 2014/0094640 A1 | 4/2014 | Gall et al. |
| 2014/0094641 A1 | 4/2014 | Gall et al. |
| 2014/0094643 A1 | 4/2014 | Gall et al. |
| 2014/0097920 A1 | 4/2014 | Goldie et al. |
| 2014/0371511 A1 | 12/2014 | Zwart et al. |

FOREIGN PATENT DOCUMENTS

| | | |
|---|---|---|
| CN | 1537657 A | 10/2004 |
| CN | 1816243 A | 8/2006 |
| CN | 101932361 | 12/2010 |
| CN | 101933405 | 12/2010 |
| CN | 101933406 | 12/2010 |
| CN | 101061759 | 5/2011 |
| DE | 2753397 | 6/1978 |
| DE | 31 48 100 | 6/1983 |

(56) References Cited

FOREIGN PATENT DOCUMENTS

| | | |
|---|---|---|
| DE | 35 30 446 | 8/1984 |
| DE | 41 01 094 C1 | 5/1992 |
| DE | 4411171 | 10/1995 |
| EP | 0 194 728 | 9/1986 |
| EP | 0 277 521 | 8/1988 |
| EP | 0 208 163 | 1/1989 |
| EP | 0 222 786 | 7/1990 |
| EP | 0 221 987 | 1/1991 |
| EP | 0 499 253 | 8/1992 |
| EP | 0 306 966 | 4/1995 |
| EP | 0 388 123 | 5/1995 |
| EP | 0 465 597 | 5/1997 |
| EP | 0 911 064 | 6/1998 |
| EP | 0 864 337 | 9/1998 |
| EP | 0 776 595 | 12/1998 |
| EP | 1 069 809 | 1/2001 |
| EP | 1 153 398 | 4/2001 |
| EP | 1 294 445 | 3/2003 |
| EP | 1 348 465 | 10/2003 |
| EP | 1 358 908 | 11/2003 |
| EP | 1 371 390 | 12/2003 |
| EP | 1 402 923 | 3/2004 |
| EP | 1 430 932 | 6/2004 |
| EP | 1 454 653 | 9/2004 |
| EP | 1 454 654 | 9/2004 |
| EP | 1 454 655 | 9/2004 |
| EP | 1 454 656 | 9/2004 |
| EP | 1 454 657 | 9/2004 |
| EP | 1 477 206 | 11/2004 |
| EP | 1 738 798 | 1/2007 |
| EP | 1 826 778 | 8/2007 |
| EP | 1826778 A2 | 8/2007 |
| EP | 1 949 404 | 7/2008 |
| EP | 2183753 | 7/2008 |
| EP | 2394498 | 2/2010 |
| EP | 2232961 | 9/2010 |
| EP | 2232962 | 9/2010 |
| EP | 2227295 | 5/2011 |
| EP | 1 605 742 | 6/2011 |
| EP | 2363170 | 9/2011 |
| EP | 2363171 | 9/2011 |
| FR | 2 560 421 | 8/1985 |
| FR | 2911843 | 8/2008 |
| GB | 0 957 342 | 5/1964 |
| GB | 1360085 | 7/1974 |
| GB | 1485329 | 9/1977 |
| GB | 2 015 821 | 9/1979 |
| GB | 1583400 | 1/1981 |
| GB | 2 361 523 | 10/2001 |
| JP | 43-23267 | 10/1968 |
| JP | U48-108098 | 12/1973 |
| JP | 57-162527 | 10/1982 |
| JP | 58-141000 | 8/1983 |
| JP | 61-80800 | 4/1986 |
| JP | 61-225798 | 10/1986 |
| JP | 62-150804 | 7/1987 |
| JP | 62-186500 | 8/1987 |
| JP | 10-071213 | 3/1988 |
| JP | 63-149344 | 6/1988 |
| JP | 63-218200 | 9/1988 |
| JP | 63-226899 | 9/1988 |
| JP | 64-89621 | 4/1989 |
| JP | 01-276797 | 11/1989 |
| JP | 01-302700 | 12/1989 |
| JP | 4-94198 | 3/1992 |
| JP | 04-128717 | 4/1992 |
| JP | 04-129768 | 4/1992 |
| JP | 04-273409 | 9/1992 |
| JP | 04-337300 | 11/1992 |
| JP | 05-341352 | 12/1993 |
| JP | 06-233831 | 8/1994 |
| JP | 06-036893 | 10/1994 |
| JP | 07-260939 | 10/1995 |
| JP | 07-263196 | 10/1995 |
| JP | 08-173890 | 7/1996 |
| JP | 08-264298 | 10/1996 |
| JP | 09-162585 | 6/1997 |
| JP | 11-47287 | 2/1999 |
| JP | 11-102800 | 4/1999 |
| JP | 11-243295 | 9/1999 |
| JP | 2000-243309 | 9/2000 |
| JP | 2000-294399 | 10/2000 |
| JP | 2001-6900 | 1/2001 |
| JP | 2001-009050 | 1/2001 |
| JP | 2001-129103 | 5/2001 |
| JP | 2001-346893 | 12/2001 |
| JP | 2002-164686 | 6/2002 |
| JP | A2003-504628 | 2/2003 |
| JP | 2003-517755 | 5/2003 |
| JP | 2004-031115 A | 1/2004 |
| JP | 2005-526578 | 9/2005 |
| JP | 2006-032282 | 2/2006 |
| JP | 05-046928 | 3/2008 |
| JP | 2008-507826 | 3/2008 |
| JP | 2009-515671 | 4/2009 |
| JP | 2009-516905 | 4/2009 |
| JP | 2010-536130 | 11/2010 |
| JP | 2011-505191 | 2/2011 |
| JP | 2011-505670 | 2/2011 |
| JP | 2011-507151 | 3/2011 |
| SU | 300137 | 11/1969 |
| SU | 569 635 | 8/1977 |
| TW | 200930160 | 7/2009 |
| TW | 200934682 | 8/2009 |
| TW | 200939908 | 9/2009 |
| TW | 200940120 | 10/2009 |
| TW | 201424466 | 6/2014 |
| TW | 201429514 | 8/2014 |
| TW | 201433331 | 9/2014 |
| TW | 201434508 | 9/2014 |
| WO | WO 86/07229 | 12/1986 |
| WO | WO 90/12413 | 10/1990 |
| WO | WO 92/03028 | 2/1992 |
| WO | WO 93/02536 | 2/1993 |
| WO | WO 98/17342 | 4/1998 |
| WO | WO 99/39385 | 8/1999 |
| WO | WO 00/40064 | 7/2000 |
| WO | WO 00/49624 | 8/2000 |
| WO | WO 01/26230 | 4/2001 |
| WO | WO 01/26569 | 4/2001 |
| WO | WO 02/07817 | 1/2002 |
| WO | WO 03/039212 | 5/2003 |
| WO | WO 03/092812 | 11/2003 |
| WO | WO 2004/026401 | 4/2004 |
| WO | WO 2004/101070 | 11/2004 |
| WO | WO 2006-012467 | 2/2006 |
| WO | WO 2007/061937 | 5/2007 |
| WO | WO 2007/084701 | 7/2007 |
| WO | WO 2007/130164 | 11/2007 |
| WO | WO 2007/145906 | 12/2007 |
| WO | WO 2008/030911 | 3/2008 |
| WO | WO 2008/081480 | 10/2008 |
| WO | WO 2009/048745 | 4/2009 |
| WO | WO 2009/070173 | 6/2009 |
| WO | WO 2009/070588 | 6/2009 |
| WO | WO 2009/073480 | 6/2009 |
| WO | WO 2009/080080 | 7/2009 |
| WO | WO 2010/089574 | 8/2010 |
| WO | WO 2013/098089 | 7/2013 |
| WO | WO 2013/142409 | 9/2013 |
| WO | WO2014/018706 | 1/2014 |
| WO | WO2014/018876 | 1/2014 |
| WO | WO 2014/052708 | 4/2014 |
| WO | WO 2014/052716 | 4/2014 |
| WO | WO 2014/052719 | 4/2014 |
| WO | WO 2014/052722 | 4/2014 |

OTHER PUBLICATIONS

International Search Report and Written Opinion mailed Jun. 10, 2014 from PCT application No. PCT/US2013/062102 (12 pages).

Ormrod, J.H., et al., "The Chalk-River Superconducting Cyclotron", Proceedings of 8th International Conference on Cyclotrons and their applications '79, 1979 (6 pages).

(56) References Cited

OTHER PUBLICATIONS

Ormrod, J.H., et al, "Status of the Chalk-River Superconducting Heavy-Ion Cyclotron", Proceedings of 9th International Conference on Cyclotrons and their Applications '81, 1981 (9 pages).
Dey, M.K., et al., "Coil Centering for the Kolkata Superconducting Cyclotron Magnet", Cyclotrons and their applications, Proceedings, 18th International Conference, Cyclotrons 2007, Giardini Naxo, Italy, Oct. 1-5, 2007 (3 pages).
Prosecution History of U.S. Appl. No. 14/039,342 (downloaded Jul. 21, 2014).
U.S. Appl. No. 61/676,377, filed Jul. 27, 2012, including the USPTO electronic file.
U.S. Appl. No. 13/949,459, filed Jul. 24, 2013, including the USPTO electronic file.
U.S. Appl. No. 13/830,792, filed Mar. 14, 2013, including the USPTO electronic file.
"Beam Delivery and Properties," *Journal of the ICRU*, 2007, 7(2):20 pages.
"510(k) Summary: Ion Beam Applications S.A.", FDA, Jul. 12, 2001, 5 pages.
"510(k) Summary: Optivus Proton Beam Therapy System", Jul. 21, 2000, 5 pages.
"An Accelerated Collaboration Meets with Beaming Success," Lawrence Livermore National Laboratory, Apr. 12, 2006, S&TR, Livermore, California, pp. 1-3, http://www.llnl.gov/str/April06/Caporaso.html.
"CPAC Highlights Its Proton Therapy Program at ESTRO Annual Meeting", TomoTherapy Incorporated, Sep. 18, 2008, Madison, Wisconsin, pp. 1-2.
"Indiana's mega-million proton therapy cancer center welcomes its first patients" [online] Press release, Health & Medicine Week, 2004, retrieved from NewsRx.com, Mar. 1, 2004, pp. 119-120.
"LLNL, UC Davis Team Up to Fight Cancer," Lawrence Livermore National Laboratory, Apr. 28, 2006, SF-06-04-02, Livermore, California, pp. 1-4.
"Patent Assignee Search Paul Scherrer Institute," Library Services at Fish & Richardson P.C., Mar. 20, 2007, 40 pages.
"Patent Prior Art Search for 'Proton Therapy System'," Library Services at Fish & Richardson P.C., Mar. 20, 2007, 46 pages.
"Superconducting Cyclotron Contract" awarded by Paul Scherrer Institute (PSI), Villigen, Switzerland, http://www.accel.de/News/superconducting_cyclotron_contract.htm, Jan. 2009, 1 page.
"The Davis 76-Inch Isochronous Cyclotron", Beam On: Crocker Nuclear Laboratory, University of California, 2009, 1 page.
"The K100 Neutron-therapy Cyclotron," National Superconducting Cyclotron Laboratory at Michigan State University (NSCL), retrieved from: http://www.nscl.msu.edu/tech/accelerators/k100, Feb. 2005, 1 page.
"The K250 Proton therapy Cyclotron," National Superconducting Cyclotron Laboratory at Michigan State University (NSCL), retrieved from: http://www.nscl.msu.edu/tech/accelerators/k250.html , Feb. 2005, 2 pages.
"The K250 Proton-therapy Cyclotron Photo Illustration," National Superconducting Cyclotron Laboratory at Michigan State University (NSCL), retrieved from: http://www.nscl.msu.edu/media/image/experimental-equipment-technology/250.html, Feb. 2005, 1 page.
18$^{th}$ Japan Conference on Radiation and Radioisotopes [Japanese], Nov. 25-27, 1987, 9 pages.
Abrosimov et al., "1000MeV Proton Beam Therapy facility at Petersburg Nuclear Physics Institute Synchrocyclotron," Medical Radiology (Moscow) 32, 10 (1987) revised in Journal of Physics, Conference Series 41, 2006, pp. 424-432, Institute of Physics Publishing Limited.
Abrosimov et al., "Neutron Time-of-flight Spectrometer Gneis at the Gatchina 1 GeV Proton Syncrhocyclotron", Mar. 9, 1985 and revised form Jul. 31, 1985, Lemingrad Nuclear Physics Institute, Gatchina, 188350, USSR (15 pages).
Adachi et al., "A 150MeV FFAG Synchrotron with "Return-Yoke Free" Magent," *Proceedings of the 2001 Particle Accelerator Conference*, Chicago, 2001, 3 pages.

Ageyev et al., "The IHEP Accelerating and Storage Complex (UNK) Status Report," *11th International Conference on High-Energy Accelerators*, 1980, pp. 60-70.
Agosteo et al., "Maze Design of a gantry room for proton therapy," *Nuclear Instruments & Methods in Physics Research*, 1996, Section A, 382, pp. 573-582.
Alexeev et al., "R4 Design of Superconducting Magents for Proton Synchrotrons," *Proceedings of the Fifth International Cryogenic Engineering Conference*, 1974, pp. 531-533.
Allardyce et al., "Performance and Prospects of the Reconstructed CERN 600 MeV Synchrocyclotron," *IEEE Transactions on Nuclear Science USA*, Jun. 1977, ns-24:(3)1631-1633.
Alonso, "Magnetically Scanned Ion Beams for Radiation Therapy," Accelerator & Fusion Research Division, Lawrence Berkeley Laboratory, Berkeley, CA, Oct. 1988, 13 pages.
Amaldi et al., "The Italian project for a hadrontherapy centre" *Nuclear Instruments and Methods in Physics Research A*, 1995, 360, pp. 297-301.
Amaldi, "Overview of the world landscape of Hadrontherapy and the projects of the TERA foundation," Physica Medica, An International journal Devoted to the Applications of Physics to Medicine and Biology, Jul. 1998, vol. XIV, Supplement 1, 6th Workshop on Heavy Charged Particles in Biology and Medicine, Instituto Scientific Europeo (ISE), Sep. 29-Oct. 1, 1977, Baveno, pp. 76-85.
Anferov et al., "Status of the Midwest Proton Radiotherapy Institute," Proceedings of the 2003 Particle Accelerator Conference, 2003, pp. 699-701.
Anferov et al., "The Indiana University Midwest Proton Radiation Institute," Proceedings of the 2001 Particle Accelerator Conference, 2001, Chicago, pp. 645-647.
Appun, "Various problems of magnet fabrication for high-energy accelerators," *Journal for All Engineers Interested in the Nuclear Field*, 1967, pp. 10-16 (1967) [Lang.: German], English bibliographic information (http://www.osti.gov/energycitations/product.biblio.jsp?osti_id=4442292).
Arduini et al. "Physical specifications of clinical proton beams from a synchrotron," *Med. Phys*, Jun. 1996, 23 (6): 939-951.
Badano et al., "Proton-Ion Medical Machine Study (PIMMS) Part I," PIMMS, Jan. 1999, 238 pages.
Beeckman et al., "Preliminary design of a reduced cost proton therapy facility using a compact, high field isochronous cyclotron," *Nuclear Instruments and Methods in Physics Research B56/57*, 1991, pp. 1201-1204.
Bellomo et al., "The Superconducting Cyclotron Program at Michigan State University," *Bulletin of the American Physical Society*, Sep. 1980, 25(7):767.
Benedikt and Carli, "Matching to Gantries for Medical Synchrotrons" *IEEE Proceedings of the 1997 Particle Accelerator Conference*, 1997, pp. 1379-1381.
Bieth et al., "A Very Compact Protontherapy Facility Based on an Extensive Use of High Temperature Superconductors (HTS)" *Cyclotrons and their Applications 1998*, Proceedings of the Fifteenth International Conference on Cyclotrons and their Applications, Caen, Jun. 14-19, 1998, pp. 669-672.
Bigham, "Magnetic Trim Rods for Superconducting Cyclotrons," Nuclear Instruments and Methods (North-Holland Publishing Co.), 1975, 141:223-228.
Bimbot, "First Studies of the External Beam from the Orsay S.C. 200 MeV," Institut de Physique Nucleaire, BP 1, Orsay, France, *IEEE*, 1979, pp. 1923-1926.
Blackmore et al., "Operation of the Triumf Proton Therapy Facility," *IEEE Proceedings of the 1997 Particle Accelerator Conference*, May 12-16, 19973:3831-3833.
Bloch, "The Midwest Proton Therapy Center," Application of Accelerators in Research and Industry, Proceedings of the Fourteenth Int'l. Conf., Part Two, Nov. 1996, pp. 1253-1255.
Blosser et al., "Problems and Accomplishments of Superconducting Cyclotrons," Proceedings of the 14$^{th}$ International Conference, Cyclotrons and Their Applications, Oct. 1995, pp. 674-684.
Blosser et al., "Superconducting Cyclotrons", Seventh International Conference on Cyclotrons and their Applications, Aug. 19-22, 1975, pp. 584-594.

(56) References Cited

OTHER PUBLICATIONS

Blosser et al., "Progress toward an experiment to study the effect of RF grounding in an internal ion source on axial oscillations of the beam in a cyclotron," National Superconducting Cyclotron Laboratory, Michigan State University, Report MSUCL-760, CP600, Cyclotrons and their Applications 2011, Sixteenth International Conference, 2001, pp. 274-276.
Blosser et al., "A Compact Superconducting Cyclotron for the Production of High Intensity Protons," Proceedings of the 1997 Particle Accelerator Conference, May 12-16, 1997, 1:1054-1056.
Blosser et al., "Advances in Superconducting Cyclotrons at Michigan State University," Proceedings of the 11$^{th}$ International Conference on Cyclotrons and their Applications, Oct. 1986, pp. 157-167, Tokyo.
Blosser et al., "Characteristics of a 400 (Q2/A) MeV Super-Conducting Heavy-Ion Cyclotron," Bulletin of the American Physical Society, Oct. 1974, p. 1026.
Blosser et al., "Medical Accelerator Projects at Michigan State Univ." IEEE Proceedings of the 1989 Particle Accelerator Conference, Mar. 20-23, 1989, 2:742-746.
Blosser et al., "Superconducting Cyclotron for Medical Application", *IEEE Transactions on Magnetics*, Mar. 1989, 25(2): 1746-1754.
Blosser, "Application of Superconductivity in Cyclotron Construction," *Ninth International Conference on Cyclotrons and their Applications*, Sep. 1981, pp. 147-157.
Blosser, "Applications of Superconducting Cyclotrons," Twelfth International Conference on Cyclotrons and Their Applications, May 8-12, 1989, pp. 137-144.
Blosser, "Future Cyclotrons," AIP, *The Sixth International Cyclotron Conference*, 1972, pp. 16-32.
Blosser, "Medical Cyclotrons," *Physics Today*, Special Issue Physical Review Centenary, Oct. 1993, pp. 70-73.
Blosser, "Preliminary Design Study Exploring Building Features Required for a Proton Therapy Facility for the Ontario Cancer Institute", Mar. 1991, MSUCL-760a, 53 pages.
Blosser, "Progress on the Coupled Superconducting Cyclotron Project," *Bulletin of the American Physical Society*, Apr. 1981, 26(4):558.
Blosser, "Synchrocyclotron Improvement Programs," *IEEE Transactions on Nuclear Science USA*, Jun. 1969, 16(3):Part I, pp. 405-414.
Blosser, "The Michigan State University Superconducting Cyclotron Program," *Nuclear Science*, Apr. 1979, NS-26(2):2040-2047.
Blosser, H., Present and Future Superconducting Cyclotrons, *Bulletin of the American Physical Society*, Feb. 1987, 32(2):171 Particle Accelerator Conference, Washington, D.C.
Blosser, H.G., "Superconducting Cyclotrons at Michigan State University", Nuclear Instruments & Methods in Physics Research, 1987,vol. B 24/25, part II, pp. 752-756.
Botha et al., "A New Multidisciplinary Separated-Sector Cyclotron Facility," *IEEE Transactions on Nuclear Science*, 1977, NS-24(3):1118-1120.
Chichili et al., "Fabrication of Nb3Sn Shell-Type Coils with Pre-Preg Ceramic Insulation," American Institute of Physics Conference Proceedings, AIP USA, No. 711, (XP-002436709, ISSN: 0094-243X), 2004, pp. 450-457.
Chong et al., Radiology Clinic North American 7, 3319, 1969, 27 pages.
Chu et al., "Performance Specifications for Proton Medical Facility," Lawrence Berkeley Laboratory, University of California, Mar. 1993, 128 pages.
Chu et al., "Instrumentation for Treatment of Cancer Using Proton and Light-ion Beams," Review of Scientific Instruments, Aug. 1993, 64 (8):2055-2122.
Chu, "Instrumentation in Medical Systems," Accelerator and Fusion Research Division, Lawrence Berkeley Laboratory, University of California, Berkeley, CA, May 1995, 9 pages.
Cole et al., "Design and Application of a Proton Therapy Accelerator," Fermi National Accelerator Laboratory, *IEEE*, 1985, 5 pages.

Collins, et al., "The Indiana University Proton Therapy System," Proceedings of EPAC 2006, Edinburgh, Scotland, 2006, 3 pages.
Conradi et al., "Proposed New Facilities for Proton Therapy at iThemba Labs," *Proceedings of EPAC*, 2002, pp. 560-562.
C/E Source of Ions for Use in Sychro-Cyclotrons Search, Jan. 31, 2005, 9 pages.
Source Search "Cites of U.S. and Foreign Patents/Published applications in the name of Mitsubishi Denki Kabushiki Kaisha and Containing the Keywords (Proton and Synchrocyclotron)," Jan. 2005, 8 pages.
Cosgrove et al., "Microdosimetric Studies on the Orsay Proton Synchrocyclotron at 73 and 200 MeV," *Radiation Protection Dosimetry*, 1997, 70(1-4):493-496.
Coupland, "High-field (5 T) pulsed superconducting dipole magnet," *Proceedings of the Institution of Electrical Engineers*, Jul. 1974, 121(7):771-778.
Coutrakon et al. "Proton Synchrotrons for Cancer Therapy," Application of Accelerators in Research and Industry—Sixteenth International Conf., American Institute of Physics, Nov. 1-5, 2000, vol. 576, pp. 861-864.
Coutrakon et al., "A prototype beam delivery system for the proton medical accelerator at Loma Linda," *Medical Physics*, Nov./Dec. 1991, 18(6):1093-1099.
Cuttone, "Applications of a Particle Accelerators in Medical Physics," Istituto Nazionale di Fisica Nucleare-Laboratori Nazionali del Sud, V.S. Sofia, 44 Cantania, Italy, Jan. 2010, 17 pages.
Dahl P, "Superconducting Magnet System," American Institute of Physics, AIP Conference Proceedings, 1987-1988, 2: 1329-1376.
Dialog Search, Jan. 31, 2005, 17 pages.
Dugan et al., "Tevatron Status" IEEE, Particle Accelerator Conference, Accelerator Science & Technology, 1989, pp. 426-430.
Eickhoff et al., "The Proposed Accelerator Facility for Light Ion Cancer Therapy in Heidelberg," Proceedings of the 1999 Particle Accelerator Conference, New York, 1999, pp. 2513-2515.
Enchevich et al., "Minimizing Phase Losses in the 680 MeV Synchrocyclotron by Correcting the Accelerating Voltage Amplitude," *Atomnaya Energiya*, 1969, 26:(3):315-316.
Endo et al., "Compact Proton and Carbon Ion Synchrotrons for Radiation Therapy," Proceedings of EPAC 2002, Paris France, 2002, pp. 2733-2735.
Flanz et al., "Treating Patients with the NPTC Accelerator Based Proton Treatment Facility," Proceedings of the 2003 Particle Accelerator Conference, 2003, pp. 690-693.
Flanz et al., "Large Medical Gantries," Particle Accelerator Conference, Massachusetts General Hospital, 1995, pp. 1-5.
Flanz et al., "Operation of a Cyclotron Based Proton Therapy Facility", Massachusetts General Hospital, Boston, MA 02114, pp. 1-4, retrieved from Internet in 2009.
Flanz et al., "The Northeast Proton Therapy Center at Massachusetts General Hospital," Fifth Workshop on Heavy Charge Particles in Biology and Medicine, GSI, Darmstadt, Aug. 1995, 11 pages.
Flood and Frazier, "The Wide-Band Driven RF System for the Berkeley 88-Inch Cyclotron," American Institute of Physics, Conference Proceedings., No. 9, 1972, 459-466.
Foster and Kashikhin, "Superconducting Superferric Dipole Magent with Cold Iron Core for the VLHC," *IEEE Transactions on Applied Superconductivity*, Mar. 2002, 12(1):111-115.
Friesel et al., "Design and Construction Progress on the IUCF Midwest Proton Radiation Institute," Proceedings of EPAC 2002, 2002, pp. 2736-2738.
Fukumoto et al., "A Proton Therapy Facility Plan" Cyclotrons and their Applications, Proceedings of the 13th International Conference, Vancouver, Canada, Jul. 6-10, 1992, pp. 258-261.
Fukumoto, "Cyclotron Versus Synchrotron for Proton Beam Therapy," KEK Prepr., No. 95-122, Oct. 1995, pp. 533-536.
Goto et al., "Progress on the Sector Magnets for the Riken SRC," American Institute of Physics, CP600, Cyclotrons and Their Applications 2001, Sixteenth International Conference, 2001, pp. 319-323.
Graffman et al., "Design Studies for a 200 MeV Proton Clinic for Radiotherapy," AIP Conference Proceedings: Cyclotrons—1972, 1972, No. 9, pp. 603-615.
Graffman et al., *Acta Radiol. Therapy Phys. Biol.* 1970, 9, 1 (1970).

(56) References Cited

OTHER PUBLICATIONS

Graffman, et. al. "Proton radiotherapy with the Uppsala cyclotron. Experience and plans" *Strahlentherapie*, 1985, 161(12):764-770.
Hede, "Research Groups Promoting Proton Therapy "Lite,""" Journal of the National Cancer Institute, Dec. 6, 2006, 98(23):1682-1684.
Heinz, "Superconducting Pulsed Magnetic Systems for High-Energy Synchrotrons," *Proceedings of the Fourth International Cryogenic Engineering Conference*, May 24-26, 1972, pp. 55-63.
Hentschel et al., "Plans for the German National Neutron Therapy Centre with a Hospital-Based 70 MeV Proton Cyclotron at University Hospital Essen/Germany," Cyclotrons and their Applications, Proceedings of the Fifteenth International Conference on Cyclotrons and their Applications, Caen, Franco, Jun. 14-19, 1998, pp. 21-23.
Hepburn et al., "Superconducting Cyclotron Neutron Source for Therapy," *International Journal of Radiation Oncology Biology Physics*, vol. 3 complete, 1977, pp. 387-391.
Hirabayashi, "Development of Superconducting Magnets for Beam Lines and Accelerator at KEK," *IEEE Transaction on Magnetics*, Jan. 1981, Mag-17(1):728-731.
Ishibashi and McInturff, "Winding Design Study of Superconducting 10 T Dipoles for a Synchrotron," *IEEE Transactions on Magnetics*, May 1983, MAG-19(3):1364-1367.
Ishibashi and McInturff, "Stress Analysis of Superconducting 10T Magnets for Synchrotron," Proceedings of the Ninth International Cryogenic Engineering Conference, May 11-14, 1982, pp. 513-516.
Jahnke et al., "First Superconducting Prototype Magnets for a Compact Synchrotron Radiation Source in Operation," *IEEE Transactions on Magnetics*, Mar. 1988, 24(2):1230-1232.
Jones and Dershem, "Synchrotron Radiation from Proton in a 20 TEV, 10 TESLA Superconducting Super Collide,r" *Proceedings of the 12th International Conference on High-Energy Accelerator*, Aug. 11-16, 1983, pp. 138-140.
Jones and Mills, "The South African National Accelerator Centre: Particle Therapy and Isotope Production Programmes," *Radiation Physics and Chemistry*, Apr.-Jun. 1998, 51(4-6):571-578.
Jones et al., "Status Report of the NAC Particle Therapy Programme," *Stralentherapie und Onkologie*, vol. 175, Suppl. II, Jun. 1999, pp. 30-32.
Jones, "Progress with the 200 MeV Cyclotron Facility at the National Accelerator Centre," Commission of the European Communities Radiation Protection Proceedings, Fifth Symposium on Neutron Dosimetry, Sep. 17-21, 1984, vol. II, pp. 989-998.
Jones, "Present Status and Future Trends of Heavy Particle Radiotherapy," Cyclotrons and their Applications 1998, Proceedings of the Fifteenth International Conference on Cyclotrons and their Applications, Jun. 14-19, 1998, pp. 13-20.
Jongen et al., "Development of a Low-cost Compact Cyclotron System for Proton Therapy," *National Institute of Radiol. Sci*, 1991, No. 81, pp. 189-200.
Jongen et al., "Progress report on the IBA-SHI small cyclotron for cancer therapy" *Nuclear Instruments and Methods in Physics Research*, Section B, vol. 79, issue 1-4, 1993, pp. 885-889.
Jongen et al., "The proton therapy system for the NPTC: Equipment Description and progress report," *Nuclear Instruments and methods in physics research*, 1996, Section B, 113(1): 522-525.
Jongen et al., "The proton therapy system for MGH's NPTC: equipment description and progress report," *Bulletin du Cancer/Radiotherapie, Proceedings of the meeting of the European Heavy Particle Therapy Group*, 1996, 83(Suppl. 1):219-222.
Kanai et al., "Three-dimensional Beam Scanning for Proton Therapy," Nuclear Instruments and Methods in Physic Research, Sep. 1, 1983, The Netherlands, 214(23):491-496.
Karlin et al., "Medical Radiology" (Moscow), 1983, 28, 13.
Karlin et al., "The State and Prospects in the Development of the Medical Proton Tract on the Synchrocyclotron in Gatchina," *Med. Radiol.*, Moscow, 28(3):28-32 (Mar. 1983)(German with English Abstract on end of p. 32).
Kats and Druzhinin, "Comparison of Methods for Irradiation Prone Patients," *Atomic Energy*, Feb. 2003, 94(2):120-123.
Kats and Onosovskii, "A Simple, Compact, Flat System for the Irradiation of a Lying Patient with a Proton Beam from Different Directions," *Instruments and Experimental Techniques*, 1996, 39(1): 132-134.
Kats and Onosovskii, "A Planar Magnetooptical System for the Irradiation of a Lying Patient with a Proton Beam from Various Directions," *Instruments and Experimental Techniques*, 1996, 39(1):127-131.
Khoroshkov et al.,"Moscow Hospital-Based Proton Therapy Facility Design," *Am. Journal Clinical Oncology: CCT*, Apr. 1994, 17(2):109-114.
Kim and Blosser, "Optimized Magnet for a 250 MeV Proton Radiotherapy Cyclotron," Cyclotrons and Their Applications 2001, May 2001, *Sixteenth International Conference*, pp. 345-347.
Kim and Yun, "A Light-Ion Superconducting Cyclotron System for Multi-Disciplinary Users," *Journal of the Korean Physical Society*, Sep. 2003, 43(3):325-331.
Kim et al., "Construction of 8T Magnet Test Stand for Cyclotron Studies," *IEEE Transactions on Applied Superconductivity*, Mar. 1993, 3(1):266-268.
Kim et al., "Design Study of a Superconducting Cyclotron for Heavy Ion Therapy," *Cyclotrons and Their Applications 2001, Sixteenth International Conference*, May 13-17 2001, pp. 324-326.
Kim et al., "Trim Coil System for the Riken Cyclotron Ring Cyclotron," *Proceedings of the 1997 Particle Accelerator Conference, IEEE*, Dec. 1981, vol. 3, pp. 214-235 Or 3422-3424, 1998.
Kim, "An Eight Tesla Superconducting Magnet for Cyclotron Studies," Ph.D. Dissertation, Michigan State University, Department of Physics and Astronomy, 1994, 138 pages.
Kimstrand, "Beam Modelling for Treatment Planning of Scanned Proton Beams," Digital Comprehensive Summaries of Uppsala dissertations from the Faculty of Medicine 330, Uppsala Universitet, 2008, 58 pages.
Kishida and Yano, "Beam Transport System for the Riken SSC (II)," *Scientific Papers of the Institute of Physical and Chemical Research*, Dec. 1981, 75(4):214-235.
Koehler et al., "Range Modulators for Protons and Heavy Ions," *Nuclear Instruments and Methods*, 1975, vol. 131, pp. 437-440.
Koto and Tsujii. "Future of Particle Therapy," *Japanese Journal of Cancer Clinics*, 2001, 47(1):95-98 [Lang.: Japanese], English abstract (http://sciencelinks.jp/j-east/article/200206/000020020601A0511453.php).
Kraft et al., "Hadrontherapy in Oncology," U. Amaldi and Larrsson, editors Elsevier Science, 1994, 390 pages.
Krevet et al., "Design of a Strongly Curved Superconducting Bending Magnet for a Compact Synchrotron Light Source," *Advances in Cryogenic Engineering*, 1988, vol. 33, pp. 25-32.
Laisne et al., "The Orsay 200 MeV Synchrocyclotron," *IEEE Transactions on Nuclear Science*, Apr. 1979, NS-26(2):1919-1922.
Larsson et al., *Nature*,1958, 182:1222.
Larsson, "Biomedical Program for the Converted 200-MeV Synchrocyclotron at the Gustaf Werner Institute," *Radiation Research*, 1985, 104:S310-S318.
Lawrence et al., "Heavy particles in acromegaly and Cushing's Disease," in Endocrine and Norendocrine Hormone Producing Tumors (Year Book Medical Chicago, 1973, pp. 29-61.
Lawrence et al., "Successful Treatment of Acromegaly: Metabolic and Clinical Studies in 145 Patients," *The Journal of Clinical Endrocrinology and Metabolism*, Aug. 1970, 31(2), 21 pages.
Lawrence et al., "Treatment of Pituitary Tumors," (Excerpta medica, Amsterdam/American Elsevier, New York, 1973, pp. 253-262.
Lawrence, *Cancer*, 1957, 10:795.
Lecroy et al., "Viewing Probe for High Voltage Pulses," *Review of Scientific Instruments USA*, Dec. 1960, 31(12):1354.
Lin et al., "Principles and 10 Year Experience of the Beam Monitor System at the PSI Scanned Proton Therapy Facility", Center for Proton Radiation Therapy, Paul Scherrer Institute, CH-5232, Villigen PSI, Switzerland, 2007, 21 pages.
Linfoot et al., "Acromegaly," in Hormonal Proteins and Peptides, edited by C.H. Li, 1975, pp. 191-246.
Literature Author and Keyword Search, Feb. 14, 2005, 44 pages.
Literature Keyword Search, Jan. 24, 2005, 98 pages.

(56) References Cited

OTHER PUBLICATIONS

Literature Search and Keyword Search for Synchrocyclotron, Jan. 25, 2005, 68 pages.
Literature Search by Company Name/Component Source, Jan. 24, 2005, 111 pages.
Literature Search, Jan. 26, 2005, 37 pages.
Livingston et al., "A capillary ion source for the cyclotron," *Review Science Instruments*, Feb. 1939, 10:63.
Mandrillon, "High Energy Medical Accelerators," *EPAC 90, 2nd European Particle Accelerator Conference*, Jun. 12-16, 1990, 2:54-58.
Marchand et al., "IBA Proton Pencil Beam Scanning: an Innovative Solution for Cancer Treatment," Proceedings of EPAC 2000, Vienna, Austria, 3 pages.
Marti et al., "High Intensity Operation of a Superconducting Cyclotron," *Proceedings of the 14the International Conference, Cyclotrons and Their Applications*, Oct. 1995, pp. 45-48 (Oct. 1995).
Martin, "Operational Experience with Superconducting Synchrotron Magnets" *Proceedings of the 1987 IEEE Particle Accelerator Conference*, Mar. 16-19, 1987, vol. 3 of 3:1379-1382.
Meote et al., "ETOILE Hadrontherapy Project, Review of Design Studies" *Proceedings of EPAC 2002*, 2002, pp. 2745-2747.
Miyamoto et al., "Development of the Proton Therapy System," *The Hitachi Hyoron*, 79(10):775-779 (1997) [Lang: Japanese], English abstract (http://www.hitachi.com/rev/1998/revfeb98/rev4706.htm).
Montelius et al., "The Narrow Proton Beam Therapy Unit at the Svedberg Laboratory in Uppsala," *ACTA Oncologica*, 1991, 30:739-745.
Moser et al., "Nonlinear Beam Optics with Real Fields in Compact Storage Rings," Nuclear Instruments & Methods in Physics Research/Section B, B30, Feb. 1988, No. 1, pp. 105-109.
Moyers et al., "A Continuously Variable Thickness Scatterer for Proton Beams Using Self-compensating Dual Linear Wedges" Lorna Linda University Medical Center, Dept. of Radiation Medicine, Lorna Linda, CA, Nov. 2, 1992, 21 pages.
*National Cancer Institute Funding* (Senate-Sep. 21, 1992) (www.thomas.loc.gov/cgi-bin/query/z?r102:S21SE2-712 (2 pages).
Nicholson, "Applications of Proton Beam Therapy," *Journal of the American Society of Radiologic Technologists*, May/Jun. 1996, 67(5): 439-441.
Nolen et al., "The Integrated Cryogenic—Superconducting Beam Transport System Planned for MSU," *Proceedings of the 12$^{th}$ International Conference on High-Energy Accelerators*, Aug. 1983, pp. 549-551.
Norimine et al., "A Design of a Rotating Gantry with Easy Steering for Proton Therapy," *Proceedings of EPAC 2002*, 2002, pp. 2751-2753.
Ogino, Takashi, "Heavy Charged Particle Radiotherapy-Proton Beam", Division of Radiation Oncology, National Cancer Hospital East, Kashiwa, Japan, Dec. 2003, 7 pages.
Okumura et al., "Overview and Future Prospect of Proton Radiotherapy," *Japanese Journal of Cancer Clinics*, 1997, 43(2):209-214 [Lang.: Japanese].
Okumura et al., "Proton Radiotherapy" *Japanese Journal of Cancer and Chemotherapy*, 1993, 10. 20(14):2149-2155[Lang.: Japanese].
Outstanding from Search Reports, "Accelerator of Polarized Portons at Fermilab," 2005, 20 pages.
Paganetti et al., "Proton Beam Radiotherapy—The State of the Art," Springer Verlag, Heidelberg, ISBN 3-540-00321-5, Oct. 2005,36 pages.
Palmer and Tollestrup, "Superconducting Magnet Technology for Accelerators," *Annual Review of Nuclear and Particle Science*, 1984, vol. 34, pp. 247-284.
Patent Assignee and Keyword Searches for Synchrocyclotron, Jan. 25, 2005, 78 pages.
Pavlovic, "Beam-optics study of the gantry beam delivery system for light-ion cancer therapy," *Nuclear Instruments and Methods in Physics Research*, Section A, Nov. 1997, 399(2):439-454(16).

Pedroni and Enge, "Beam optics design of compact gantry for proton therapy" *Medical & Biological Engineering & Computing*, May 1995, 33(3):271-277.
Pedroni and Jermann, "SGSMP: Bulletin Mar. 2002 Proscan Project, Progress Report on the Proscan Project of PSI" [online] retrieved from www.sgsmp.ch/protA23.htm, Mar. 2002, 5 pages.
Pedroni et al., "A Novel Gantry for Proton Therapy at the Paul Scherrer Institute," *Cycloctrons and Their Applications 2001: Sixteenth International Conference. AIP Conference Proceedings*, 2001, 600:13-17.
Pedroni et al., "The 200-MeV proton therapy project at the Paul Scherrer Institute: Conceptual design and practical realization," *Medical Physics*, Jan. 1995, 22(1):37-53.
Pedroni, "Accelerators for Charged Particle Therapy: Performance Criteria from the User Point of View," *Cyclotrons and their Applications, Proceedings of the 13th International Conference*, Jul. 6-10, 1992, pp. 226-233.
Pedroni, "Latest Developments in Proton Therapy" *Proceedings of EPAC 2000*, pp. 240-244, 2000.
Pedroni, "Status of Proton Therapy: results and future trends," Paul Scherrer Institute, Division of Radiation Medicine, 1994, 5 pages.
Peggs et al., "A Survey of Hadron Therapy Accelerator Technologies," Particle Accelerator Conference, Jun. 25-29, 2007, 7 pages.
Potts et al., "MPWP6-Therapy III: Treatment Aids and Techniques" *Medical Physics*, Sep./Oct. 1988, 15(5):798.
Pourrahimi et al., "Powder Metallurgy Processed Nb3Sn(Ta) Wire for High Field NMR magnets," *IEEE Transactions on Applied Superconductivity*, Jun. 1995, 5(2):1603-1606.
Prieels et al., "The IBA State-of-the-Art Proton Therapy System, Performances and Recent Results," *Application of Accelerators in Research and industry—Sixteenth Int'l. Conf., American Institute of Physics*, Nov. 1-5, 2000, 576:857-860.
Rabin et al., "Compact Designs for Comprehensive Proton Beam Clinical Facilities," *Nuclear Instruments & Methods in Physics Research*, Apr. 1989, Section B, vol. 40-41, Part II, pp. 1335-1339.
*Research & Development Magazine*, "Proton Therapy Center Nearing Completion," Aug. 1999, 41(9):2 pages, (www.rdmag.com).
Resmini, "Design Characteristics of the K=800 Superconducting Cyclotron at M.S.U.," Cyclotron Laboratory, Michigan State University, East Lansing, Michigan 48824, IEEE Transaction on Nuclear Science, vol. NS-26, No. 2, Apr. 1979, 8 pages.
RetroSearch "Berkeley 88-Inch Cyclotron 'RF' or 'Frequency Control'," Jan. 21, 2005, 36 pages.
RetroSearch "Berkeley 88-Inch Cyclotron," Jan. 24, 2005, 170 pages.
RetroSearch "Bernard Gottschalk, Cyclotron, Beams, Compensated Upstream Modulator, Compensated Scatter," Jan. 21, 2005, 20 pages.
RetroSearch "Cyclotron with 'RF' or 'Frequency Control'," Jan. 21, 2005, 49 pages.
RetroSearch Gottschalk, Bernard, Harvard Cyclotron Wheel, Jan. 21, 2005, 20 pages.
RetroSearch "Loma Linda University Beam Compensation," Jan. 21, 2005, 60 pages.
RetroSearch "Loma Linda University, Beam Compensation Foil Wedge," Jan. 21, 2005, 15 pages.
Revised Patent Keyword Search, Jan. 25, 2005, 88 pages.
Rifuggiato et, al., "Status Report of the LNS Superconducting Cyclotron" *Nukleonika*, 2003, 48: S131-S134, Supplement 2.
Rode, "Tevatron Cryogenic System," *Proceedings of the 12th International Conference on High-energy Accelerators, Fermilab*, Aug. 11-16, 1983, pp. 529-535.
Salzburger et al., "Superconducting Synchrotron Magnets Supraleitende Synchrotronmagnete," Siemens A.G., Erlangen (West Germany). Abteilung Technische Physik, Report No. BMFT-FB-T-75-25, Oct. 1975, p. 147, Journal Announcement: GRAI7619; STAR1415, Subm-Sponsored by Bundesmin. Fuer Forsch. U. Technol. In German; English Summary.
Schillo et al., "Compact Superconducting 250 MeV Proton Cyclotron for the PSI Proscan Proton Therapy Project," *Cyclotrons and Their Applications 2001, Sixteenth International Conference*, 2001, pp. 37-39.

(56) References Cited

OTHER PUBLICATIONS

Schneider et al., "Nevis Synchrocyclotron Conversion Program—RF System," *IEEE Transactions on Nuclear Science USA*, Jun. 1969, ns 16(3): 430-433.
Schneider et al., "Superconducting Cyclotrons," IEEE Transactions on Magnetics, vol. MAG-11, No. 2, Mar. 1975, New York, pp. 443-446.
Schreuder et al., "The Non-orthogonal Fixed Beam Arrangement for the Second Proton Therapy Facility at the National Accelerator Centre," *Application of Accelerators in Research and Industry, American Institute of Physics, Proceedings of the Fifteenth International Conference*, Nov. 1998, Part Two, pp. 963-966.
Schreuder, "Recent Developments in Superconducting Cyclotrons," *Proceedings of the 1995 Particle Accelerator Conference*, May 1-5, 1995, vol. 1, pp. 317-321.
Schubert and Blosser, "Conceptual Design of a High Field Ultra-Compact Cyclotron for Nuclear Physics Research," *Proceedings of the 1997 Particle Accelerator Conference*, May 12-16, 1997, vol. 1, 3 pages 1060-1062.
Schubert, "Extending the Feasibility Boundary of the Isochronous Cyclotron," Dissertation submitted to Michigan State University, 1997, Abstract http://adsabs.harvard.edu/abs/1998PhDT . . . 147S.
Shelaev et al., "Design Features of a Model Superconducting Synchrotron of JINR," *Proceedings of the 12th International Conference on High-energy Accelerators*, Aug. 11-16, 1983, pp. 416-418.
Shintomi et. Al, "Technology and Materials for the Superconducting Super Collider (SSC) Project," [Lang.: Japanese], The Iron and Steel Institute of Japan 00211575, 78(8): 1305-1313, 1992, http://ci.nii.ac.jp/naid/110001493249/en/.
Sisterson, "World Wide Proton Therapy Experience in 1997," *The American Insitute of Physics, Applications of Accelerators in Research and Industry, Proceedings of the Fifteenth International Conference*, Part Two, Nov. 1998, pp. 959-962.
Sisterson, "Clinical use of proton and ion beams from a world-wide perspective," *Nuclear Instruments and Methods in Physics Research*, Section B, 1989, 40-41:1350-1353.
Slater et al., "Developing a Clinical Proton Accelerator Facility: Consortium-Assisted Technology Transfer," *Conference Record of the 1991 IEEE Particle Accelerator Conference: Accelerator Science and Technology*, vol. 1, May 6-9, 1991, pp. 532-536.
Slater et al., "Development of a Hospital-Based Proton Beam Treatment Center," *International Journal of Radiation Oncology Biology Physics*, Apr. 1988, 14(4):761-775.
Smith et al., "The Northeast Proton Therapy Center at Massachusetts General Hospital" *Journal of Brachytherapy International*, Jan. 1997, pp. 137-139.
Snyder and Marti, "Central region design studies for a proposed 250 MeV proton cyclotron," *Nuclear Instruments and Methods in Physics Research*, Section A, 1995, vol. 355, pp. 618-623.
Soga, "Progress of Particle Therapy in Japan," Application of Accelerators in Research and Industry, American Institute of Physics, Sixteenth International Conference, Nov. 2000, pp. 869-872.
Spiller et al., "The GSI Synchrotron Facility Proposal for Acceleration of High Intensity Ion and Proton Beams" *Proceedings of the 2003 Particle Accelerator Conference*, May 12-16, 2003, vol. 1, pp. 589-591.
Stanford et al., "Method of Temperature Control in Microwave Ferroelectric Measurements," Sperry Microwave Electronics Company, Clearwater, Florida, Sep. 19, 1960, 1 page.
Tadashi et al., "Large superconducting super collider (SSC) in the planning and materials technology," 78(8):1305-1313, The Iron and Steel Institute of Japan 00211575, Aug. 1992.
Takada, "Conceptual Design of a Proton Rotating Gantry for Cancer Therapy," *Japanese Journal of Medical Physics*, 1995, 15(4):270-284.
Takayama et al., "Compact Cyclotron for Proton Therapy," *Proceedings of the 8th Symposium on Accelerator Science and Technology*, Japan, Nov. 25-27, 1991, pp. 380-382.

Teng, "The Fermilab Tevatron," Coral Gables 1981, Proceedings, Gauge Theories, Massive Neutrinos, and Proton Decay, 1981, pp. 43-62.
The Journal of Practical Pharmacy, 1995, 46(1):97-103 [Japanese].
Tilly, et al., "Development and verification of the pulsed scanned proton beam at The Svedberg Laboratory in Uppsala", Physics in Medicine and Biology, Phys. Med. Biol. 52, pp. 2741-2454, 2007.
Tobias et al., *Cancer Research*,1958, 18, 121 (1958).
Tom, "The Use of Compact Cyclotrons for Producing Fast Neutrons for Therapy in a Rotatable Isocentric Gantry," *IEEE Transaction on Nuclear Science*, Apr. 1979, 26(2):2294-2298.
Toyoda, "Proton Therapy System", Sumitomo Heavy Industries, Ltd., 2000, 5 pages.
Trinks et. al., "The Tritron: A Superconducting Separated-Orbit Cyclotron," *Nuclear Instruments and Methods in Physics Research*, Section A, 1986, vol. 244, pp. 273-282.
Tsuji, "The Future and Progress of Proton Beam Radiotherapy," *Journal of Japanese Society for Therapeutic Radiology and Oncology*, 1994, 6(2):63-76.
UC Davis School of Medicine, "Unlikely Partners Turn Military Defense into Cancer Offense", Current Issue Summer 2008, Sacramento, California, pp. 1-2.
Umegaki et al., "Development of an Advanced Proton Beam Therapy System for Cancer Treatment" *Hitachi Hyoron*, 2003, 85(9):605-608 [Lang.: Japanese], English abstract, http://www.hitachi.com/ICSFiles/afieldfile/2004/06/01/r2003__04__104.pdf or http://www.hitachi.com/rev/archive/2003/2005649__12606.html (full text) [Hitachi, 52(4), Dec. 2003].
Umezawa et al., "Beam Commissioning of the new Proton Therapy System for University of Tsukuba," *Proceedings of the 2001 Particle Accelerator Conference*, vol. 1, Jun. 18-22, 2001, pp. 648-650.
van Steenbergen, "Superconducting Synchroton Development at BNL," *Proceedings of the 8th International Conference on High-Energy Accelerators CERN 1971*, 1971, pp. 196-198.
van Steenbergen, "The CMS, a Cold Magnet Synchrotron to Upgrade the Proton Energy Range of the BNL Facility," *IEEE Transactions on Nuclear Science*, Jun. 1971, 18(3):694-698.
Vandeplassche et al., "235 MeV Cyclotron for MGH's Northeast Proton Therapy Center (NPTC): Present Status," EPAC 96, *Fifth European Partical Accelerator Conference*, vol. 3, Jun. 10-14, 1996, pp. 2650-2652.
Vorobiev et al., "Concepts of a Compact Achromatic Proton Gantry with a Wide Scanning Field", Nuclear Instruments and Methods in Physics Research, Section A., 1998, 406(2):307-310.
Vrenken et al., "A Design of a Compact Gantry for Proton Therapy with 2D-Scanning," *Nuclear Instruments and Methods in Physics Research*, Section A, 1999, 426(2):618-624.
Wikipedia, "Cyclotron" http://en.wikipedia.org/wiki/Cyclotron (originally visited Oct. 6, 2005, revisited Jan. 28, 2009), 7 pages.
Wikipedia, "Synchrotron" http://en.wikipedia.org/wiki/Synchrotron (originally visited Oct. 6, 2005, revisited Jan. 28, 2009), 7 pages.
Worldwide Patent Assignee Search, Jan. 24, 2005, 224 pages.
Worldwide Patent Keyword Search, Jan. 24, 2005, 94 pages.
Wu, "Conceptual Design and Orbit Dynamics in a 250 MeV Superconducting Synchrocyclotron," Ph.D. Dissertation, Michigan State University, Department of Physics and Astronomy, 1990, 172 pages.
York et al., "Present Status and Future Possibilities at NSCL-MSU," EPAC 94, Fourth European Particle Accelerator Conference, pp. 554-556, Jun. 1994.
York et al., "The NSCL Coupled Cyclotron Project—Overview and Status," *Proceedings of the Fifteenth International Conference on Cyclotrons and their Applications*, Jun. 1998, pp. 687-691.
Yudelev et al., "Hospital Based Superconducting Cyclotron for Neutron Therapy: Medical Physics Perspective," *Cyclotrons and their applications 2001, 16th International Conference. American Institute of Physics Conference Proceedings*, vol. 600, May 13-17, 2001, pp. 40-43.

(56) References Cited

OTHER PUBLICATIONS

Zherbin et al., "Proton Beam Therapy at the Leningrad Synchrocyclotron (Clinicomethodological Aspects and Therapeutic Results)", Aug. 1987, 32(8):17-22, (German with English abstract on pp. 21-22).

International Preliminary Report on Patentability from PCT application PCT/US2013/062102 issued Apr. 9, 2015 (9 pages).

Elo, Don, et al., "Mechanical Design of Regenerative Deflector for the Berkeley 88-Inch Cyclotron", Proceedings of the International Conference on Isochronous Cyclotrons, Gatlinburg, Tennessee, Aug. 1966 (7 pages).

Rainwater, James, "Status of the Nevis Synchrocyclotron Modification", AIP Conference Proceedings No. 9, 1972 (14 pages).

Wu, Xiao Yu, "Conceptual Design and Orbit Dynamics in a 250 MeV Superconducting Synchrocyclotron", Michigan State University, 1990 (170 pages).

Cohen, R. et al., "Nevis Synchrocyclotron Conversion Project", IEEE Transactions on Nuclear Science, IEEE Service Center, New York, NY, US, vol. 16, No. 3, Jun. 1, 1969, pp. 421-425, XP011351570, ISSN: 0018-9499, DOI: 10.1109/TNS.1969. 4325264 abstract; figures 1-4a Chap. 1, p. 421-2; chap. 11 from p. 423, col. 2 to p. 425, col. 1. (5 pages).

International Preliminary Report on Patentability issued in PCT application No. PCT/US2013/062102 on Apr. 19, 2015 (10 pages).

US 8,581,524, 11/2013, O'Neal et al. (withdrawn)

* cited by examiner

MAGNETIC SHIMS TO ALTER MAGNETIC FIELDS

CROSS-REFERENCE TO RELATED APPLICATION

Priority is hereby claimed to U.S. Provisional Application No. 61/707,548, which was filed on Sep. 28, 2012. The contents of U.S. Provisional Application No. 61/707,548 are hereby incorporated by reference into this disclosure.

TECHNICAL FIELD

This disclosure relates generally to use of magnetic shims in a superconducting magnet of a particle therapy system.

BACKGROUND

Particle therapy systems use an accelerator to generate a particle beam for treating afflictions, such as tumors. The accelerator typically includes an electromagnet having a superconducting coil. The superconducting coil is maintained on a cryostat that is positioned between two magnetic structures called yokes. Precise positioning of the coil can be important. If the coil is improperly positioned, magnetic forces generated by the yokes can physically damage the coil and/or prevent the extraction of the particle beam. Physical movement of the particle accelerator can, however, affect the position of the coil.

SUMMARY

An example particle accelerator includes a coil to provide a magnetic field to a cavity; a cryostat comprising a chamber for holding the coil, where the coil is arranged in the chamber to define an interior region of the coil and an exterior region of the coil; magnetic structures adjacent to the cryostat, where the magnetic structures have one or more slots at least part-way therethrough; and one or more magnetic shims in one or more corresponding slots. The one or more magnetic shims are movable to adjust a position of the coil by changing a magnetic field produced by the magnetic structures. This example particle accelerator may include one or more of the following features, either alone or in combination.

The one or more magnetic shims may be controllable to move into or out of corresponding slots. The one or more magnetic shims may be computer controlled. The one or more magnetic shims may be controllable in response to rotation of the particle accelerator. The one or more magnetic shims may be controllable to adjust the position of the coil to compensate for motion of the coil caused by rotation of the particle accelerator. The one or more magnetic shims may include ferromagnetic material.

At least one of the magnetic shims may be within the interior region. All of the magnetic shims may be within the interior region, in which case no magnetic shims are in an exterior region.

An example proton therapy system includes the foregoing particle accelerator; and a gantry on which the particle accelerator is mounted. The gantry is rotatable relative to a patient position. Protons are output essentially directly from the particle accelerator to the patient position. In the example proton therapy system, the particle accelerator may be rotatable relative to a fixed position, and the proton therapy system may include a control system to control movement of the one or more magnetic shims based on a rotational position of the gantry.

An example electromagnet includes a superconducting coil arranged in a substantially circular configuration to generate a magnetic field; magnetic structures adjacent to the superconducting coil, where the magnetic structures have one or more slots at least part-way therethrough; and one or more magnetic shims in one or more corresponding slots, where the one or more magnetic shims are movable to adjust a position of the coil by changing a magnetic field produced by the magnetic structures. This example electromagnet may include one or more of the following features, either alone or in combination.

The superconducting coil may be configured to generate a magnetic field that is stronger in an interior of the circular configuration than in an exterior of the circular configuration. The one or more magnetic shims may be closer to the interior of the circular configuration than to the exterior of the circular configuration. At least part of the one or more magnetic shims may be within the interior of the circular configuration. All of the magnetic shims may be within the interior of the circular configuration (and none on an exterior thereof).

The one or more magnetic shims may be controllable to move into or out of corresponding slots. The one or more magnetic shims may be computer controlled. The one or more magnetic shims may be controllable in response to rotation of the electromagnet. The one or more magnetic shims may be controllable to adjust the position of the coil to compensate for motion of the coil caused by rotation of the electromagnet. The one or more magnetic shims may include one or more magnetic shims comprised of ferromagnetic material.

An example proton therapy system may include a particle accelerator comprising the foregoing electromagnet for outputting particles comprising protons; and a gantry on which the particle accelerator is mounted. The gantry may be rotatable relative to a patient position. Protons may be output essentially directly from the particle accelerator to the patient position. The particle accelerator may be rotatable relative to a fixed position. The proton therapy system may include a control system to control movement of the one or more magnetic shims based on a rotational position of the gantry.

An example method of adjusting a position of a superconducting coil in an electromagnet may include the following: determining a rotational position associated with the electromagnet; and, based on the rotational position, controlling a position of one or more magnetic shims in a magnetic structure proximate to the superconducting coil. This example method may include one or more of the following features, either alone or in combination.

The electromagnet may be part of a particle accelerator that is mounted on a gantry that is rotatable. The rotational position may be a position of the gantry. The superconducting coil may be arranged in a substantially circular configuration to generate a magnetic field. The magnetic field may be stronger in an interior of the circular configuration than in an exterior of the circular configuration. The one or more magnetic shims may be closer to the interior of the circular configuration than to the exterior of the circular configuration. At least part of the one or more magnetic shims may be within the interior of the circular configuration. All of the one or more magnetic shims may be within the interior of the circular configuration, and none on its exterior.

The one or more magnetic shims may be controllable to move into or out of corresponding slots in the magnetic structure. The position of the one or more magnetic shims may be controlled using a computer. The one or more magnetic shims may be controllable to adjust the position of the coil to compensate for motion of the coil caused by rotation of the electromagnet. The one or more magnetic shims may include one or more magnetic shims comprised of ferromagnetic material.

An example particle accelerator includes: a coil to provide a magnetic field to a cavity in which particles are accelerated; a cryostat comprising a chamber for holding the coil; magnetic structures adjacent to the cryostat, where the magnetic structures have one or more slots at least part-way therethrough; and one or more magnetic shims in one or more corresponding slots, where the one or more magnetic shims are movable to adjust a magnetic field in the cavity in order to affect a particle orbit within the cavity. The example particle accelerator may include one or more of the following features, either alone or in combination The particle accelerator may include an extraction channel, through which the particles pass for output from the particle accelerator, where the extraction channel has an entrance at the cavity. The one or more magnetic shims are controlled in the one or more corresponding slots so that an energy of particles entering the extraction channel from the cavity matches an energy required for the particles to traverse the extraction channel. The entrance to the extraction channel may not include an energy absorbing structure through which the particle beam passes prior to entry to the extraction channel. The magnetic structures may comprise pole pieces and the coil is a first coil. The particle accelerator may include a second coil that operates as an active return for magnetic field resulting from current through the first coil.

A proton therapy system may include the foregoing particle accelerator. The system may also include a gantry on which the particle accelerator is mounted, where the gantry is rotatable relative to a patient position. Protons may be output essentially directly from the particle accelerator to the patient position.

Two or more of the features described in this disclosure, including those described in this summary section, may be combined to form implementations not specifically described herein.

Control of the various systems described herein, or portions thereof, may be implemented via a computer program product that includes instructions that are stored on one or more non-transitory machine-readable storage media, and that are executable on one or more processing devices. The systems described herein, or portions thereof, may be implemented as an apparatus, method, or electronic system that may include one or more processing devices and memory to store executable instructions to implement control of the stated functions.

The details of one or more implementations are set forth in the accompanying drawings and the description below. Other features, objects, and advantages will be apparent from the description and drawings, and from the claims.

DESCRIPTION OF THE DRAWINGS

Like reference symbols in the various drawings indicate like elements.

DETAILED DESCRIPTION

Overview

Figure 1:
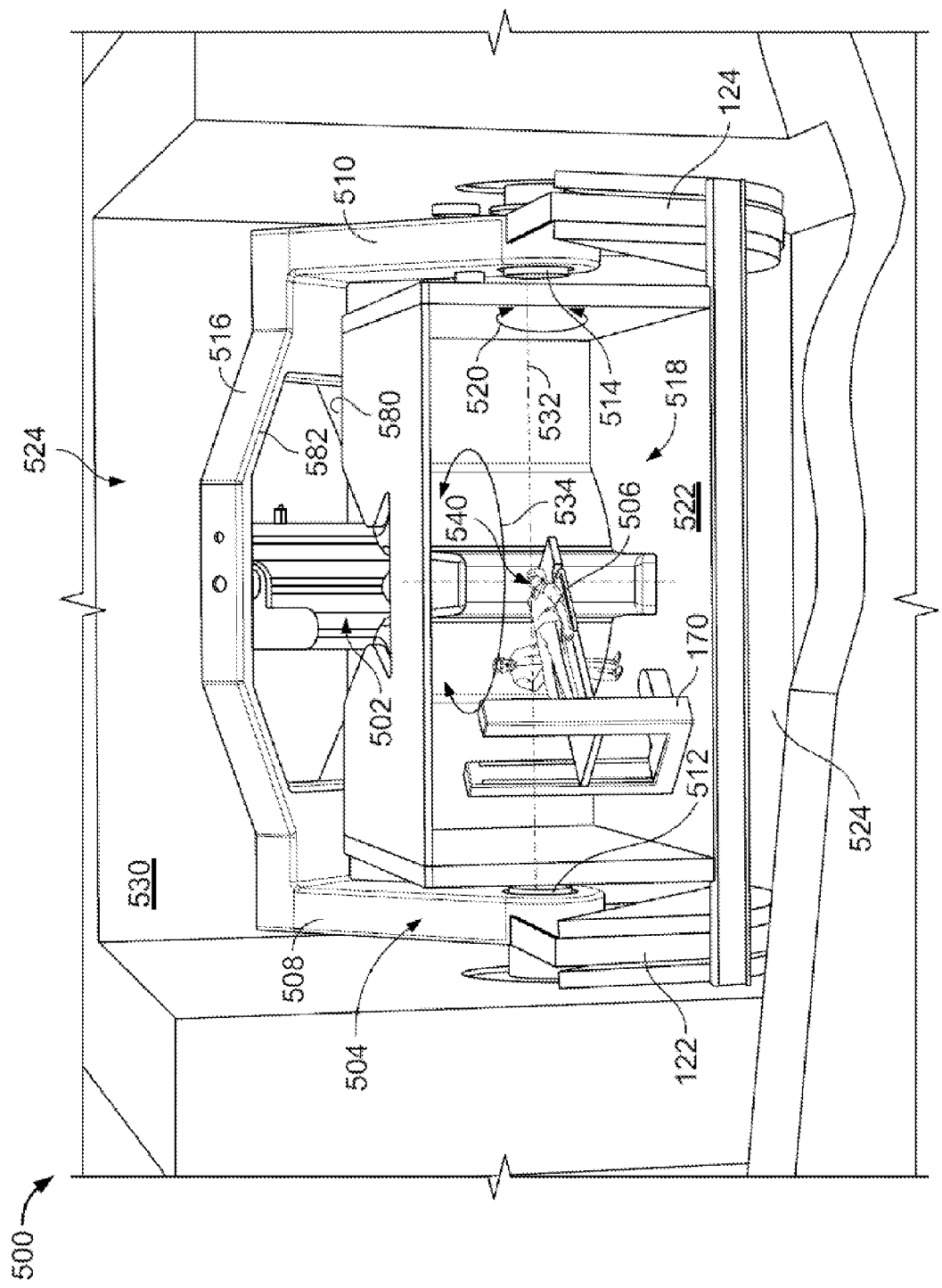
FIG. 1 is a perspective view of an example therapy system.
Figure 2:
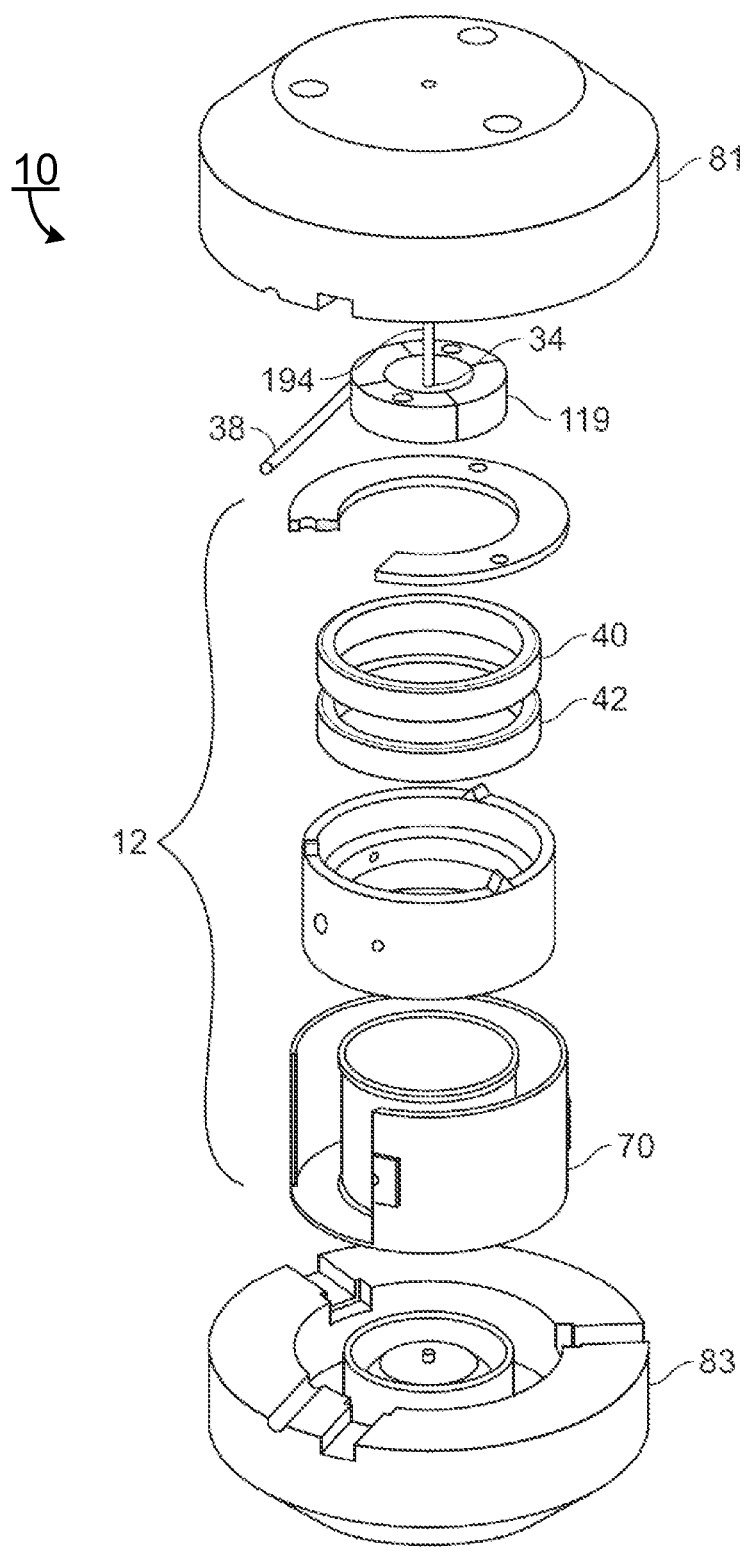
FIG. 2 is an exploded perspective view of components of an example synchrocyclotron.

Described herein is an example of a particle accelerator for use in an example system, such as a proton or ion therapy system. The system includes a particle accelerator—in this example, a synchrocyclotron—mounted on a gantry. The gantry enables the accelerator to be rotated around a patient position, as explained in more detail below. In some implementations, the gantry is steel and has two legs mounted for rotation on two respective bearings that lie on opposite sides of a patient. The particle accelerator is supported by a steel truss that is long enough to span a treatment area in which the patient lies and that is attached stably at both ends to the rotating legs of the gantry. As a result of rotation of the gantry around the patient, the particle accelerator also rotates.

A superconducting magnet is part of the particle accelerator. For example the particle accelerator (e.g., the synchrocyclotron) may include a cryostat that holds a superconducting coil for conducting a current that generates a magnetic field (B). In this example, the cryostat uses liquid helium (He) to maintain the coil at superconducting temperatures, e.g., 4° Kelvin (K). The superconducting coil is held in a coil chamber in the cryostat. The coil chamber is substantially circular, and the superconducting coil is thus held in a substantially circular configuration. As a result of this geometry, the magnetic field produced by the superconducting coil is greater in an interior region surrounded by the superconducting coil than in an exterior of that region.

Magnetic yokes are adjacent (e.g., around) the cryostat, and define a cavity in which particles are accelerated. The cryostat is attached to the magnetic yokes. While this attachment, and the attachment of the superconducting coil in the cryostat, restricts movement of the superconducting coil, coil movement is not entirely prevented. For example, in some implementations, as a result of gravitational pull during rotation, the superconducting coil is movable by small amounts (e.g., tenths of millimeters in some cases). This movement can affect the amount of energy in a particle beam that is received at an extraction channel and thereby affect the output of the particle accelerator. If the movement is great enough, physical damage to the coil supports can result, e.g., the coil supports may break.

In an example, the particle accelerator also includes a particle source (e.g., a Penning Ion Gauge—PIG source) to provide a plasma column to the cavity. Hydrogen gas is ionized to produce the plasma column. A voltage source provides a radio frequency (RF) voltage to the cavity to accelerate particles from the plasma column. In this example, the particle accelerator is a synchrocyclotron. Accordingly, the RF voltage is swept across a range of frequencies to account for relativistic effects on the particles (e.g., increasing particle mass). The magnetic field produced by the coil causes particles accelerated from the plasma column to accelerate orbitally within the cavity. A magnetic field regenerator is positioned in the cavity to adjust the existing magnetic field inside the cavity to thereby change locations of successive orbits of the particles accelerated from the plasma column so that, eventually, the particles output to an extraction channel contained in the yokes. The regenerator may increase the magnetic field at an area of the cavity, thereby causing each successive orbit of particles at that area to precess outward toward the entry point of the extraction channel, eventually reaching the extraction channel. The extraction channel receives particles accelerated from the plasma column and outputs the received particles from the cavity.

Movement of the superconducting coil can affect the locations of the orbits inside the cavity and thereby prevent a particle beam from exiting the accelerator. For example, movement in one direction can cause lower-energy orbits to impact the regenerator, while movement in another direction can cause higher-energy orbits to impact the regenerator (particle orbit energy is proportional to the radial distance from the originating plasma column). So, in a case where overly low-energy orbits impact the regenerator, the particle beam may collide with the inner edge of the extraction channel, as noted above. In a case where overly high-energy orbits impact the regenerator, the particle beam may collide with the outer edge of the extraction channel, as noted above. In some implementations, movement of the superconducting coil one the order of tenths (e.g., $2/10^{th}$) of a millimeter can effect operation of the particle accelerator in this manner.

As noted above, if there is enough movement, the coil can suffer physical damage during operation. For example, in some implementations, if the superconducting coil is off-centered by as little as two millimeters, forces that occur during operation of the electromagnet may damage the coil supports.

The example systems described herein use techniques to adjust the position of the superconducting coil within the cryostat chamber to correct for motion of the superconducting coil due to its rotation (e.g., due to the effect of gravity). A summary of these techniques is provided below, followed by a description of an example particle therapy system in which they may be implemented and more detailed descriptions of these various techniques.

In this regard, the yokes are made of a ferromagnetic material, such as steel. It is therefore possible to adjust the effective magnetic center of the yokes using one or more magnetic shims. Force resulting from magnetic interaction of the coil with the ferromagnetic yoke (or other ferromagnetic structure that replaces the yoke) can be used to move the superconducting coil from one position to another position relative to the yoke. For example, the magnetic material in one area of the coil magnetic field can be increased, resulting in force to move the superconducting coil in one direction, or the magnetic material in that area can be decreased, resulting in force to move the superconducting coil in another, different direction.

In example implementations, the effective magnetic center of the yoke is adjusted by moving a magnetic shim within a hole (or slot) in a magnetic yoke that is near to the superconducting coil. Any appropriate type of magnetic shim may be used to implement the techniques described herein; however, the implementations described herein use multiple ferromagnetic rod-shaped magnetic shims that are movable into, and out from, slots in the yokes. For example, screws may be used to control motion of the magnetic shims vis-à-vis the slots/holes.

In example implementations, each magnetic shim is made of ferromagnetic material. A proximity of each magnetic shim to a corresponding superconducting coil affects the amount of force applied to the superconducting coil by the resulting magnetic field. Moving a magnetic shim closer to the superconducting coil (e.g., further inside a slot in a yoke) increases the magnetic field force on the coil. Conversely, moving the magnetic shim away from the superconducting coil (e.g., upwards in, or outside of, the slot) decreases the magnetic field force on the coil. In other implementations, there may be opposite reactions to magnetic shim movement into, and out of, slot in the yokes.

Multiple magnetic shims may be used at varying locations relative to the superconducting coil in order to properly position the superconducting coil. For example, in some implementations, the positioning may be on the order of tenths-of-millimeters. In other implementations, the positioning may be more or less than in the tenths-of-millimeters range. The magnetic shims may be computer-controlled to vary their positions based, e.g., on a rotational position of the particle accelerator.

The foregoing example techniques for adjusting the position of a superconducting coil are not limited to use with a particle accelerator or to use with a particle therapy system. Rather, such techniques, or variations thereof, may be used with any appropriate electromagnet that includes a superconducting coil in any type of medical or non-medical application. An example of a particle therapy system in which the foregoing techniques may be used is provided below.

Example Particle Therapy System

Referring to FIG. 1, a charged particle radiation therapy system 500 includes a beam-producing particle accelerator 502 having a weight and size small enough to permit it to be mounted on a rotating gantry 504 with its output directed straight (that is, essentially directly) from the accelerator housing toward a patient 506.

In some implementations, the steel gantry has two legs 508, 510 mounted for rotation on two respective bearings 512, 514 that lie on opposite sides of the patient. The accelerator is supported by a steel truss 516 that is long enough to span a treatment area 518 in which the patient lies (e.g., twice as long as a tall person, to permit the person to be rotated fully within the space with any desired target area of the patient remaining in the line of the beam) and is attached stably at both ends to the rotating legs of the gantry.

In some examples, the rotation of the gantry is limited to a range 520 of less than 360 degrees, e.g., about 180 degrees, to permit a floor 522 to extend from a wall of the vault 524 that houses the therapy system into the patient treatment area. The limited rotation range of the gantry also reduces the required thickness of some of the walls, which provide radiation shielding of people outside the treatment area. A range of 180 degrees of gantry rotation is enough to cover all treatment approach angles, but providing a larger range of travel can be useful. For example the range of rotation may be between 180 and 330 degrees and still provide clearance for the therapy floor space.

The horizontal rotational axis 532 of the gantry is located nominally one meter above the floor where the patient and therapist interact with the therapy system. This floor is positioned about 3 meters above the bottom floor of the therapy system shielded vault. The accelerator can swing under the raised floor for delivery of treatment beams from below the rotational axis. The patient couch moves and rotates in a substantially horizontal plane parallel to the rotational axis of the gantry. The couch can rotate through a range 534 of about 270 degrees in the horizontal plane with this configuration. This combination of gantry and patient rotational ranges and degrees of freedom allow the therapist to select virtually any approach angle for the beam. If needed, the patient can be placed on the couch in the opposite orientation and then all possible angles can be used.

In some implementations, the accelerator uses a synchrocyclotron configuration having a very high magnetic field superconducting electromagnetic structure. Because the bend radius of a charged particle of a given kinetic energy is reduced in direct proportion to an increase in the magnetic field applied to it, the very high magnetic field superconducting magnetic structure permits the accelerator to be made smaller and lighter. The synchrocyclotron uses a magnetic field that is uniform in rotation angle and falls off in strength with increasing radius. Such a field shape can be achieved regardless of the magnitude of the magnetic field, so in theory there is no upper limit to the magnetic field strength (and therefore the resulting particle energy at a fixed radius) that can be used in a synchrocyclotron.

Superconducting materials lose their superconducting properties in the presence of very high magnetic fields. High performance superconducting wire windings are used to allow very high magnetic fields to be achieved.

Superconducting materials typically need to be cooled to low temperatures for their superconducting properties to be realized. In some examples described here, cryo-coolers are used to bring the superconducting coil windings to temperatures near absolute zero. Using cryo-coolers can reduce complexity and cost.

The synchrocyclotron is supported on the gantry so that the beam is generated directly in line with the patient. The gantry permits rotation of the cyclotron about a horizontal rotational axis that contains a point (isocenter 540) within, or near, the patient. The split truss that is parallel to the rotational axis, supports the cyclotron on both sides.

Because the rotational range of the gantry is limited, a patient support area can be accommodated in a wide area around the isocenter. Because the floor can be extended broadly around the isocenter, a patient support table can be positioned to move relative to and to rotate about a vertical axis 542 through the isocenter so that, by a combination of gantry rotation and table motion and rotation, any angle of beam direction into any part of the patient can be achieved. The two gantry arms are separated by more than twice the height of a tall patient, allowing the couch with patient to rotate and translate in a horizontal plane above the raised floor.

Limiting the gantry rotation angle allows for a reduction in the thickness of at least one of the walls surrounding the treatment room. Thick walls, typically constructed of concrete, provide radiation protection to individuals outside the treatment room. A wall downstream of a stopping proton beam may be about twice as thick as a wall at the opposite end of the room to provide an equivalent level of protection. Limiting the range of gantry rotation enables the treatment room to be sited below earth grade on three sides, while allowing an occupied area adjacent to the thinnest wall reducing the cost of constructing the treatment room.

In the example implementation shown in FIG. 1, the superconducting synchrocyclotron 502 operates with a peak magnetic field in a pole gap of the synchrocyclotron of 8.8 Tesla. The synchrocyclotron produces a beam of protons having an energy of 250 MeV. In other implementations the field strength could be in the range of 6 to 20 Tesla or 4 to 20 Tesla and the proton energy could be in the range of 150 to 300 MeV The radiation therapy system described in this example is used for proton radiation therapy, but the same principles and details can be applied in analogous systems for use in heavy ion (ion) treatment systems.

As shown in FIGS. 2, 3, 4, 5, and 6, an example synchrocyclotron 10 (e.g., 502 in FIG. 1) includes a magnet system 12 that contains an particle source 90, a radiofrequency drive system 91, and a beam extraction system 38. The magnetic field established by the magnet system has a shape appropriate to maintain focus of a contained proton beam using a combination of a split pair of annular superconducting coils 40, 42 and a pair of shaped ferromagnetic (e.g., low carbon steel) pole faces 44, 46.

Figures 7, 8:
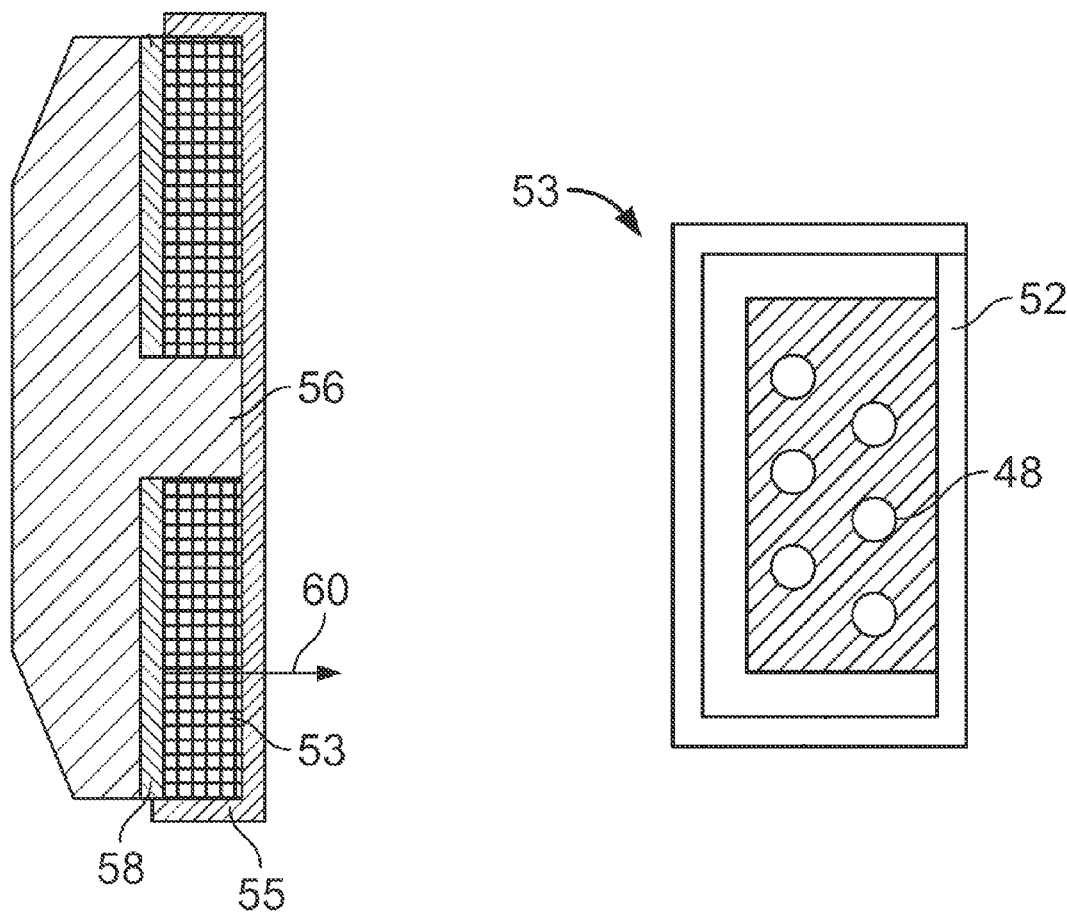
FIG. 7 is a cross-sectional view of a portion of an example reverse bobbin and windings.
FIG. 8 is a cross sectional view of an example cable-in-channel composite conductor.

The two superconducting magnet coils are centered on a common axis 47 and are spaced apart along the axis. As shown in FIGS. 7 and 8, the coils are formed by of $Nb_3Sn$-based superconducting 0.8 mm diameter strands 48 (that initially comprise a niobium-tin core surrounded by a copper sheath) deployed in a twisted cable-in-channel conductor geometry. After seven individual strands are cabled together, they are heated to cause a reaction that forms the final (brittle) superconducting material of the wire. After the material has been reacted, the wires are soldered into the copper channel (outer dimensions 3.18×2.54 mm and inner dimensions 2.08× 2.08 mm) and covered with insulation 52 (in this example, a woven fiberglass material). The copper channel containing the wires 53 is then wound in a coil having a rectangular cross-section of 8.55 cm×19.02 cm, having 26 layers and 49 turns per layer. The wound coil is then vacuum impregnated with an epoxy compound. The finished coils are mounted on an annular stainless steel reverse bobbin 56. Heater blankets 55 are placed at intervals in the layers of the windings to protect the assembly in the event of a magnet quench.

The entire coil can then be covered with copper sheets to provide thermal conductivity and mechanical stability and then contained in an additional layer of epoxy. The precompression of the coil can be provided by heating the stainless steel reverse bobbin and fitting the coils within the reverse bobbin. The reverse bobbin inner diameter is chosen so that when the entire mass is cooled to 4 K, the reverse bobbin stays in contact with the coil and provides some compression. Heating the stainless steel reverse bobbin to approximately 50 degrees C. and fitting coils at a temperature of 100 degrees Kelvin can achieve this.

Figure 5:
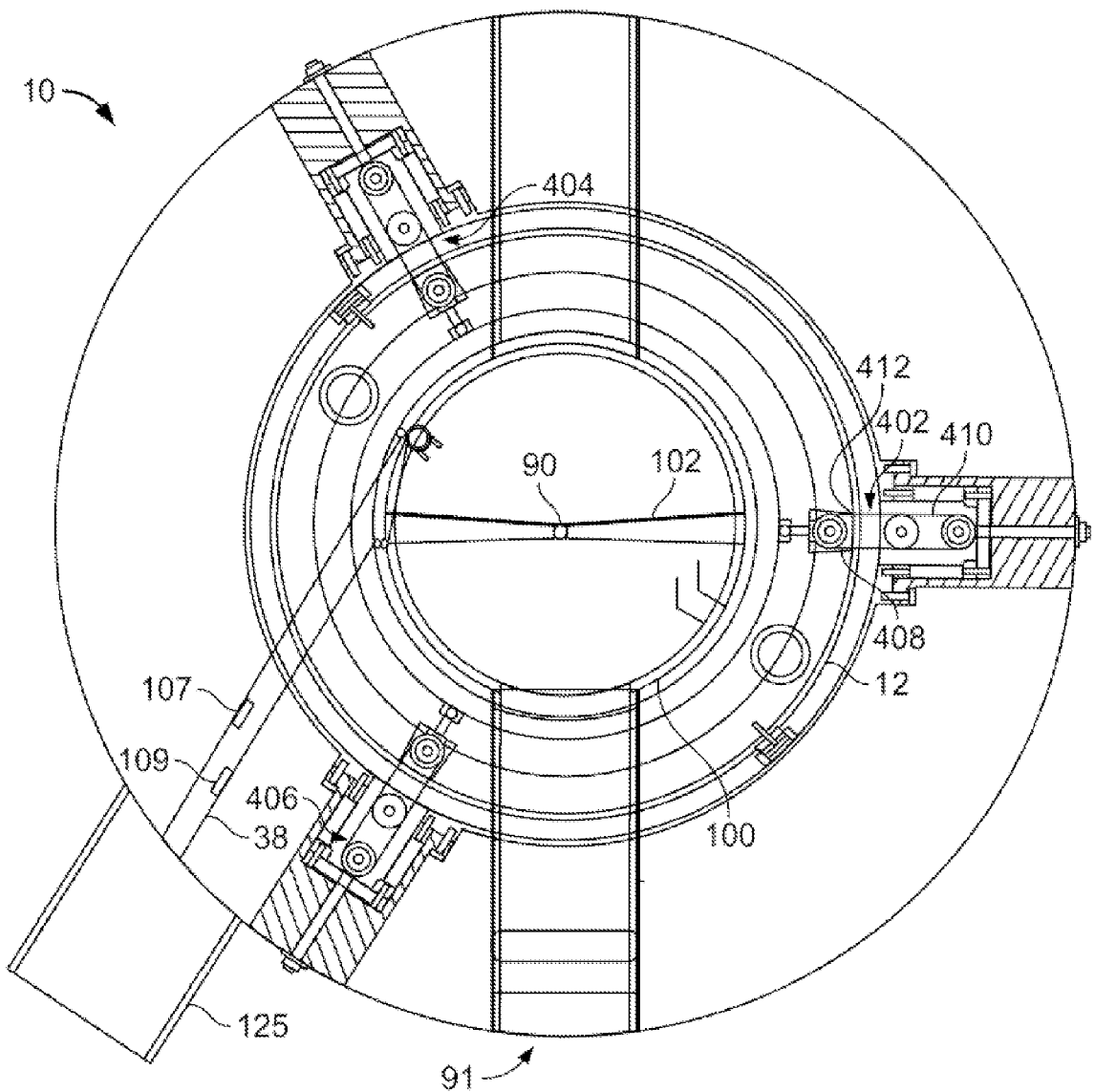
Figure 6:
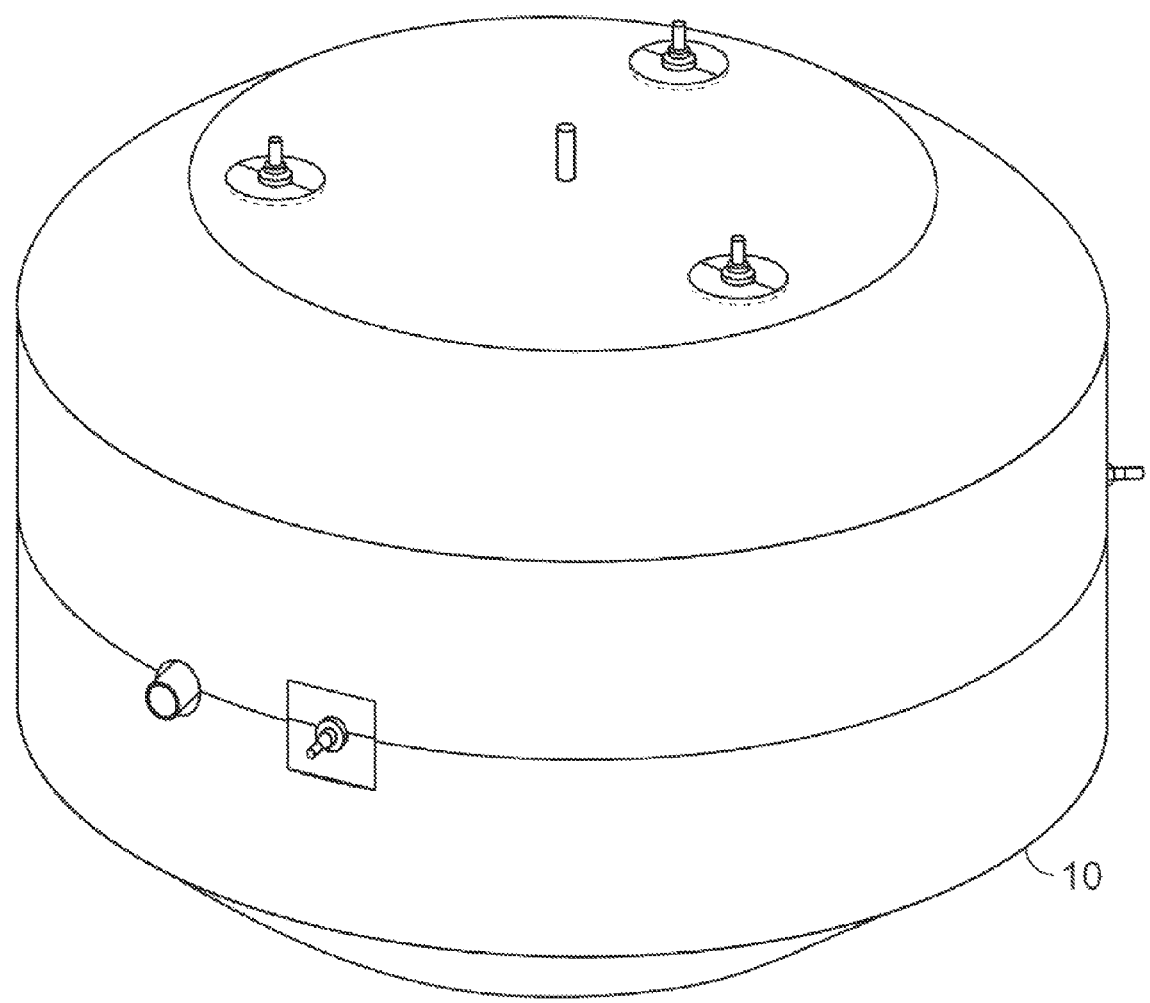
FIG. 6 is a perspective view of an example synchrocyclotron.

The geometry of the coil is maintained by mounting the coils in a reverse rectangular bobbin 56 to exert a restorative force 60 that works against the distorting force produced when the coils are energized. As shown in FIG. 5, the coil position is maintained relative to the magnet yoke and cryostat using a set of warm-to-cold support straps 402, 404, 406. Supporting the cold mass with thin straps reduces the heat leakage imparted to the cold mass by the rigid support system. The straps are arranged to withstand the varying gravitational force on the coil as the magnet rotates on board the gantry. They withstand the combined effects of gravity and the large de-centering force realized by the coil when it is perturbed from a perfectly symmetric position relative to the magnet yoke. Additionally the links act to reduce dynamic forces imparted on the coil as the gantry accelerates and decelerates when its position is changed. Each warm-to-cold support includes one S2 fiberglass link and one carbon fiber link. The carbon fiber link is supported across pins between the warm yoke and an intermediate temperature (50-70 K), and the S2 fiberglass link 408 is supported across the intermediate temperature pin and a pin attached to the cold mass. Each link is 5 cm long (pin center to pin center) and is 17 mm wide. The link thickness is 9 mm. Each pin is made of high strength stainless steel and is 40 mm in diameter.

Figure 3:
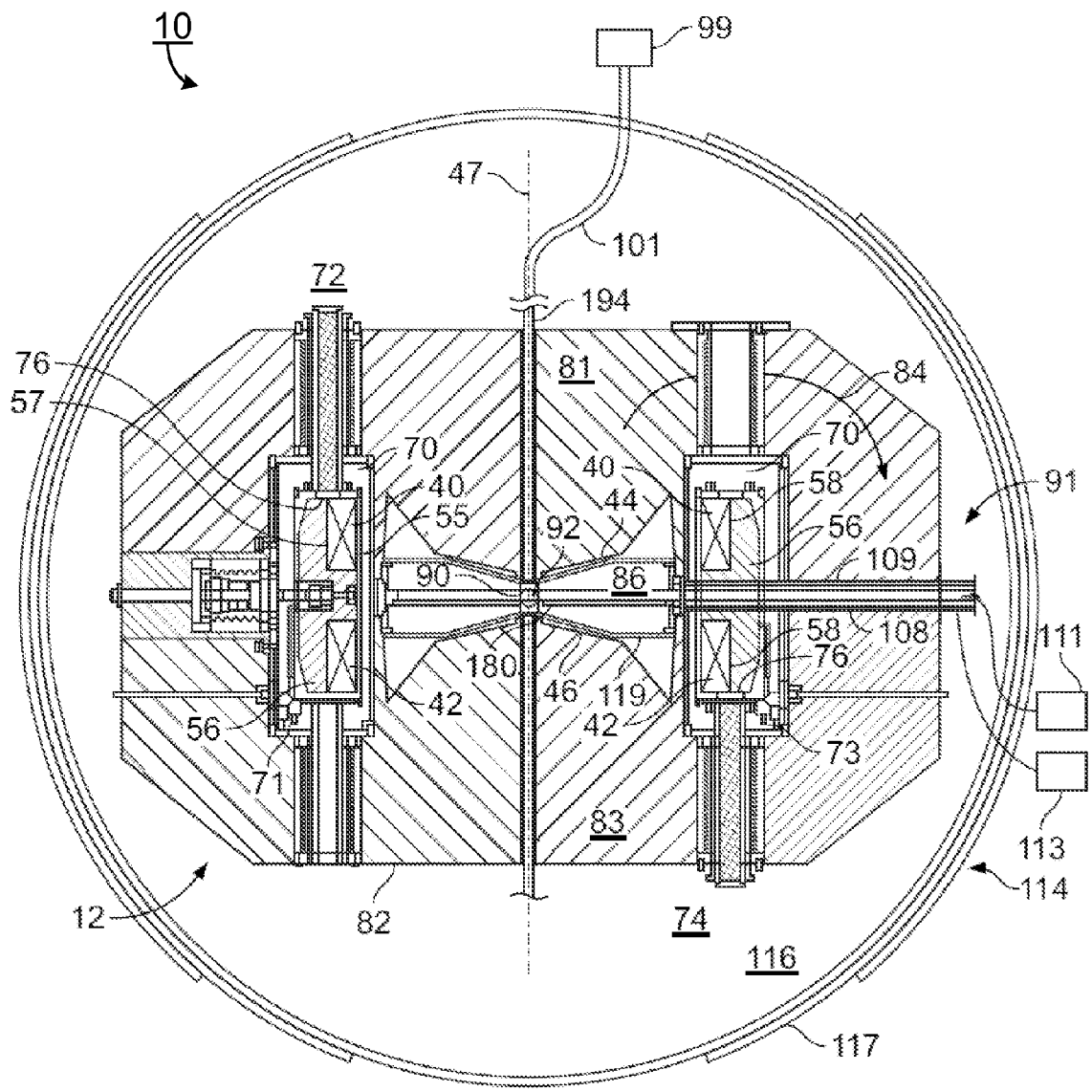
FIGS. 3, 4, and 5 are cross-sectional views of an example synchrocyclotron.
Figure 4:
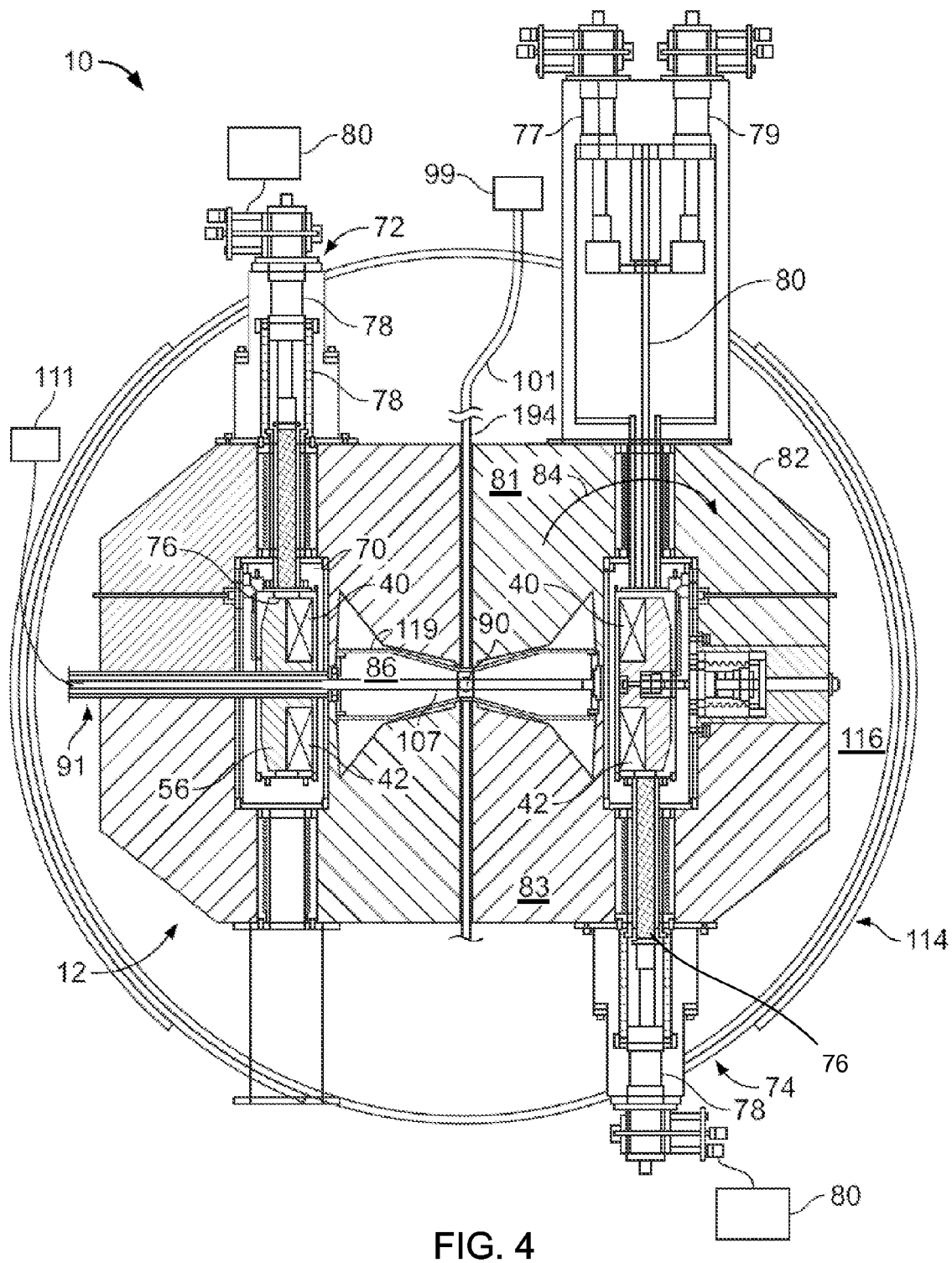

Referring to FIG. 3, the field strength profile as a function of radius is determined largely by choice of coil geometry and pole face shape; the pole faces 44, 46 of the permeable yoke material can be contoured to fine tune the shape of the magnetic field to ensure that the particle beam remains focused during acceleration.

The superconducting coils are maintained at temperatures near absolute zero (e.g., about 4 degrees Kelvin) by enclosing the coil assembly (the coils and the bobbin) inside an evacuated annular aluminum or stainless steel cryostatic chamber 70 that provides a free space around the coil structure, except at a limited set of support points 71, 73. In an alternate version (FIG. 4) the outer wall of the cryostat may be made of low carbon steel to provide an additional return flux path for the magnetic field.

In some implementations, the temperature near absolute zero is achieved and maintained using one single-stage Gifford-McMahon cryo-cooler and three two-stage Gifford McMahon cryo-coolers. Each two stage cryo-cooler has a second stage cold end attached to a condenser that recondenses Helium vapor into liquid Helium. The cryo-cooler heads are supplied with compressed Helium from a compressor. The single-stage Gifford-McMahon cryo-cooler is arranged to cool high temperature (e.g., 50-70 degrees Kelvin) leads that supply current to the superconducting windings.

In some implementations, the temperature near absolute zero is achieved and maintained using two Gifford-McMahon cryo-coolers 72, 74 that are arranged at different positions on the coil assembly. Each cryo-cooler has a cold end 76 in contact with the coil assembly. The cryo-cooler heads 78 are supplied with compressed Helium from a compressor 80. Two other Gifford-McMahon cryo-coolers 77, 79 are arranged to cool high temperature (e.g., 60-80 degrees Kelvin) leads that supply current to the superconducting windings.

The coil assembly and cryostatic chambers are mounted within and fully enclosed by two halves 81, 83 of a pillbox-shaped magnet yoke 82. In this example, the inner diameter of the coil assembly is about 74.6 cm. The iron yoke 82 provides a path for the return magnetic field flux 84 and magnetically shields the volume 86 between the pole faces 44, 46 to prevent external magnetic influences from perturbing the shape of the magnetic field within that volume. The yoke also serves to decrease the stray magnetic field in the vicinity of the accelerator. In some implementations, the synchrocyclotron may have an active return system to reduce stray magnetic fields. An example of an active return system is described in U.S. patent application Ser. No. 13/907,601, which was filed on May 31, 2013, the contents of which are incorporated herein by reference. In the active return system, the relatively large magnetic yokes described herein are replaced by smaller magnetic structures, referred to as pole pieces. Superconducting coils run current opposite to the main coils described herein in order to provide magnetic return and thereby reduce stray magnetic fields.

Figure 9:
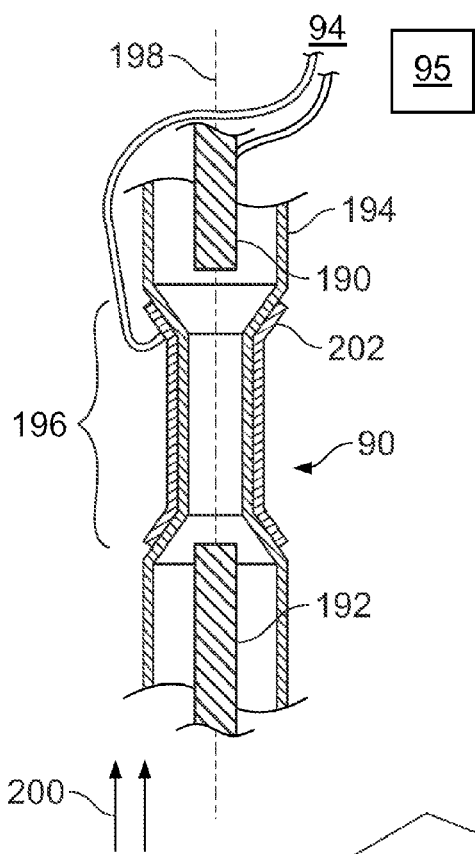
FIG. 9 is a cross-sectional view of an example ion source.

As shown in FIGS. 3 and 9, the synchrocyclotron includes a particle source 90 of a Penning ion gauge geometry located near the geometric center 92 of the magnet structure 82. The particle source may be as described below, or the particle source may be of the type described in U.S. patent application Ser. No. 11/948,662 incorporated herein by reference.

Particle source 90 is fed from a supply 99 of hydrogen through a gas line 101 and tube 194 that delivers gaseous hydrogen. Electric cables 94 carry an electric current from a current source 95 to stimulate electron discharge from cathodes 192, 190 that are aligned with the magnetic field, 200.

In some implementations, the gas in gas tube 101 may include a mixture of hydrogen and one or more other gases. For example, the mixture may contain hydrogen and one or more of the noble gases, e.g., helium, neon, argon, krypton, xenon and/or radon (although the mixture is not limited to use with the noble gases). In some implementations, the mixture may be a mixture of hydrogen and helium. For example, the mixture may contain about 75% or more of hydrogen and about 25% or less of helium (with possible trace gases included). In another example, the mixture may contain about 90% or more of hydrogen and about 10% or less of helium (with possible trace gases included). In examples, the hydrogen/helium mixture may be any of the following: >95%/<5%, >90%/<10%, >85%/<15%, >80%/<20%, >75%/<20%, and so forth.

Possible advantages of using a noble (or other) gas in combination with hydrogen in the particle source may include: increased beam intensity, increased cathode longevity, and increased consistency of beam output.

In this example, the discharged electrons ionize the gas exiting through a small hole from tube 194 to create a supply of positive ions (protons) for acceleration by one semicircular (dee-shaped) radio-frequency plate 100 that spans half of the space enclosed by the magnet structure and one dummy dee plate 102. In the case of an interrupted particle source (an example of which is described in U.S. patent application Ser. No. 11/948,662), all (or a substantial part) of the tube containing plasma is removed at the acceleration region, thereby allowing ions to be more rapidly accelerated in a relatively high magnetic field.

Figure 10:
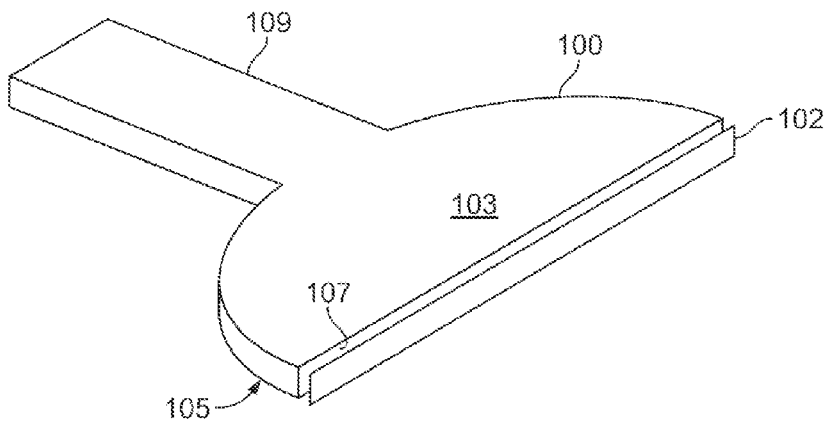
FIG. 10 is a perspective view of an example dee plate and an example dummy dee.

As shown in FIG. 10, the dee plate 100 is a hollow metal structure that has two semicircular surfaces 103, 105 that enclose a space 107 in which the protons are accelerated during half of their rotation around the space enclosed by the magnet structure. A duct 109 opening into the space 107 extends through the yoke to an external location from which a vacuum pump 111 can be attached to evacuate the space 107 and the rest of the space within a vacuum chamber 119 in which the acceleration takes place. The dummy dee 102 comprises a rectangular metal ring that is spaced near to the exposed rim of the dee plate. The dummy dee is grounded to the vacuum chamber and magnet yoke. The dee plate 100 is driven by a radio-frequency signal that is applied at the end of a radio-frequency transmission line to impart an electric field in the space 107. The radio frequency electric field is made to vary in time as the accelerated particle beam increases in distance from the geometric center. The radio frequency electric field may be controlled in the manner described in U.S. patent application Ser. No. 11/948,359, entitled "Matching A Resonant Frequency Of A Resonant Cavity To A Frequency Of An Input Voltage", the contents of which are incorporated herein by reference.

For the beam emerging from the centrally located particle source to clear the particle source structure as it begins to spiral outward, a large voltage difference is required across the radio frequency plates. 20,000 Volts is applied across the radio frequency plates. In some versions from 8,000 to 20,000 Volts may be applied across the radio frequency plates. To reduce the power required to drive this large voltage, the magnet structure is arranged to reduce the capacitance between the radio frequency plates and ground. This is done by forming holes with sufficient clearance from the radio frequency structures through the outer yoke and the cryostat housing and making sufficient space between the magnet pole faces.

The high voltage alternating potential that drives the dee plate has a frequency that is swept downward during the accelerating cycle to account for the increasing relativistic mass of the protons and the decreasing magnetic field. The dummy dee does not require a hollow semi-cylindrical structure as it is at ground potential along with the vacuum chamber walls. Other plate arrangements could be used such as more than one pair of accelerating electrodes driven with different electrical phases or multiples of the fundamental frequency. The RF structure can be tuned to keep the Q high during the required frequency sweep by using, for example, a rotating capacitor having intermeshing rotating and stationary blades. During each meshing of the blades, the capacitance increases, thus lowering the resonant frequency of the RF structure. The blades can be shaped to create a precise frequency sweep required. A drive motor for the rotating condenser can be phase locked to the RF generator for precise control. One bunch of particles is accelerated during each meshing of the blades of the rotating condenser.

The vacuum chamber 119 in which the acceleration occurs is a generally cylindrical container that is thinner in the center and thicker at the rim. The vacuum chamber encloses the RF plates and the particle source and is evacuated by the vacuum pump 111. Maintaining a high vacuum insures that accelerating ions are not lost to collisions with gas molecules and enables the RF voltage to be kept at a higher level without arcing to ground.

Protons traverse a generally spiral orbital path beginning at the particle source. In half of each loop of the spiral path, the protons gain energy as they pass through the RF electric field in space 107. As the ions gain energy, the radius of the central orbit of each successive loop of their spiral path is larger than the prior loop until the loop radius reaches the maximum radius of the pole face. At that location a magnetic and electric field perturbation directs ions into an area where the magnetic field rapidly decreases, and the ions depart the area of the high magnetic field and are directed through an evacuated tube 38, referred to herein as the extraction channel, to exit the yoke of the cyclotron. A magnetic regenerator may be used to change the magnetic field perturbation to direct the ions. The ions exiting the cyclotron will tend to disperse as they enter the area of markedly decreased magnetic field that exists in the room around the cyclotron. Beam shaping elements 107, 109 in the extraction channel 38 redirect the ions so that they stay in a straight beam of limited spatial extent.

The magnetic field within the pole gap needs to have certain properties to maintain the beam within the evacuated chamber as it accelerates. The magnetic field index n, which is shown below, $$n=-(r/B)dB/dr,$$

should be kept positive to maintain this "weak" focusing. Here r is the radius of the beam and B is the magnetic field. Additionally, in some implementations, the field index needs to be maintained below 0.2, because at this value the periodicity of radial oscillations and vertical oscillations of the beam coincide in a $v_r=2\ v_z$ resonance. The betatron frequencies are defined by $v_r=(1-n)^{1/2}$ and $v_z=n^{1/2}$. The ferromagnetic pole face is designed to shape the magnetic field generated by the coils so that the field index n is maintained positive and less than 0.2 in the smallest diameter consistent with a 250 MeV beam in the given magnetic field.

As the beam exits the extraction channel it is passed through a beam formation system 125 (FIG. 5) that can be programmably controlled to create a desired combination of scattering angle and range modulation for the beam. Beam formation system 125 may be used in conjunction with an inner gantry 601 (FIG. 14) to direct a beam to the patient.

During operation, the plates absorb energy from the applied radio frequency field as a result of conductive resistance along the surfaces of the plates. This energy appears as heat and is removed from the plates using water cooling lines 108 that release the heat in a heat exchanger 113 (FIG. 3).

Stray magnetic fields exiting from the cyclotron are limited by both the pillbox magnet yoke (which also serves as a shield) and a separate magnetic shield 114. The separate magnetic shield includes of a layer 117 of ferromagnetic material (e.g., steel or iron) that encloses the pillbox yoke, separated by a space 116. This configuration that includes a sandwich of a yoke, a space, and a shield achieves adequate shielding for a given leakage magnetic field at lower weight.

As mentioned, the gantry allows the synchrocyclotron to be rotated about the horizontal rotational axis 532. The truss structure 516 has two generally parallel spans 580, 582. The synchrocyclotron is cradled between the spans about midway between the legs. The gantry is balanced for rotation about the bearings using counterweights 122, 124 mounted on ends of the legs opposite the truss.

The gantry is driven to rotate by an electric motor mounted to one or both of the gantry legs and connected to the bearing housings by drive gears. The rotational position of the gantry is derived from signals provided by shaft angle encoders incorporated into the gantry drive motors and the drive gears.

At the location at which the ion beam exits the cyclotron, the beam formation system 125 acts on the ion beam to give it properties suitable for patient treatment. For example, the beam may be spread and its depth of penetration varied to provide uniform radiation across a given target volume. The beam formation system can include passive scattering elements as well as active scanning elements.

All of the active systems of the synchrocyclotron (the current driven superconducting coils, the RF-driven plates, the vacuum pumps for the vacuum acceleration chamber and for the superconducting coil cooling chamber, the current driven particle source, the hydrogen gas source, and the RF plate coolers, for example), may be controlled by appropriate synchrocyclotron control electronics (not shown), which may include, e.g., one or more computers programmed with appropriate programs to effect control.

The control of the gantry, the patient support, the active beam shaping elements, and the synchrocyclotron to perform a therapy session is achieved by appropriate therapy control electronics (not shown).

Figure 11:
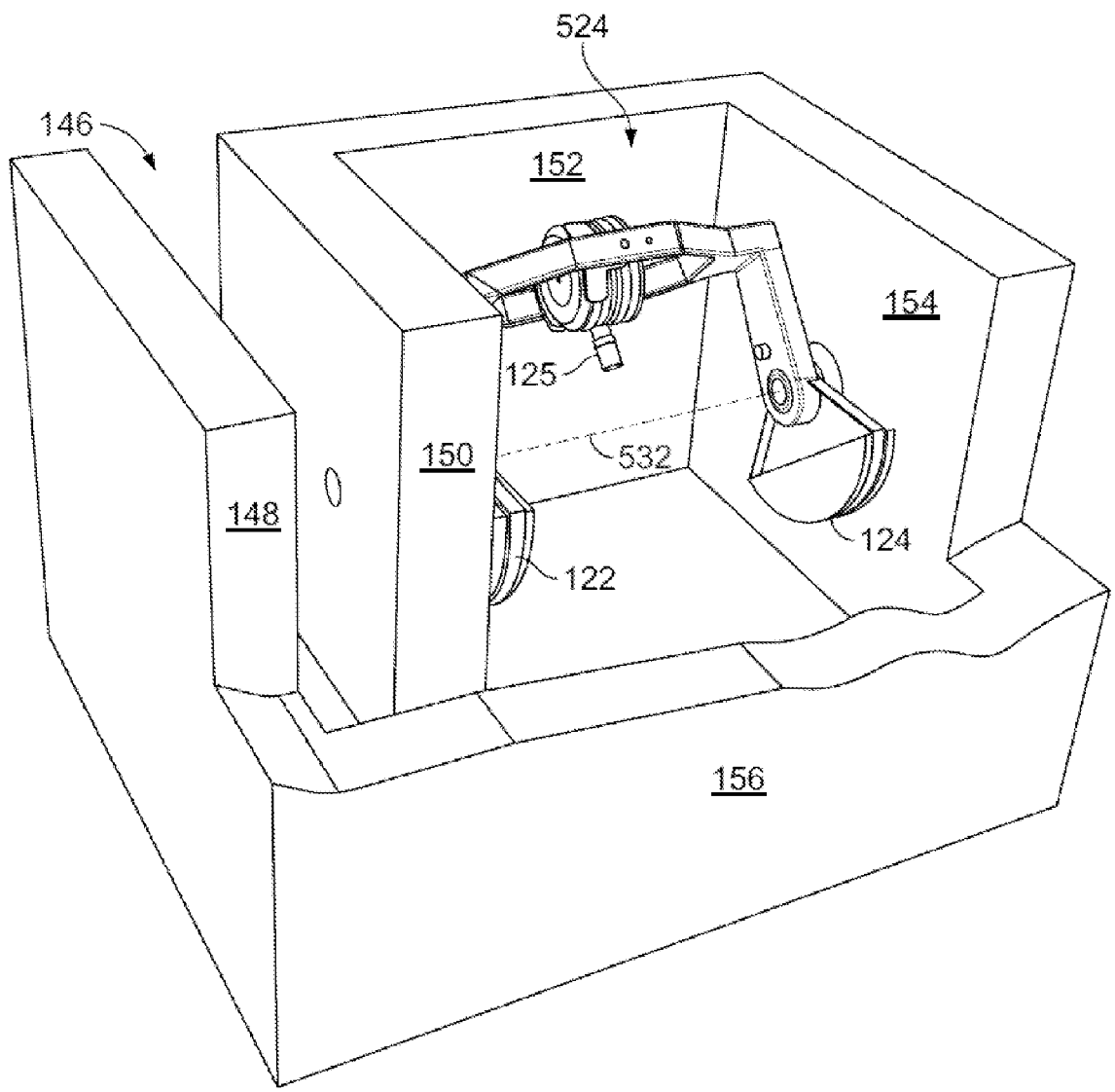
FIG. 11 is a perspective view of an example vault.
Figure 12:
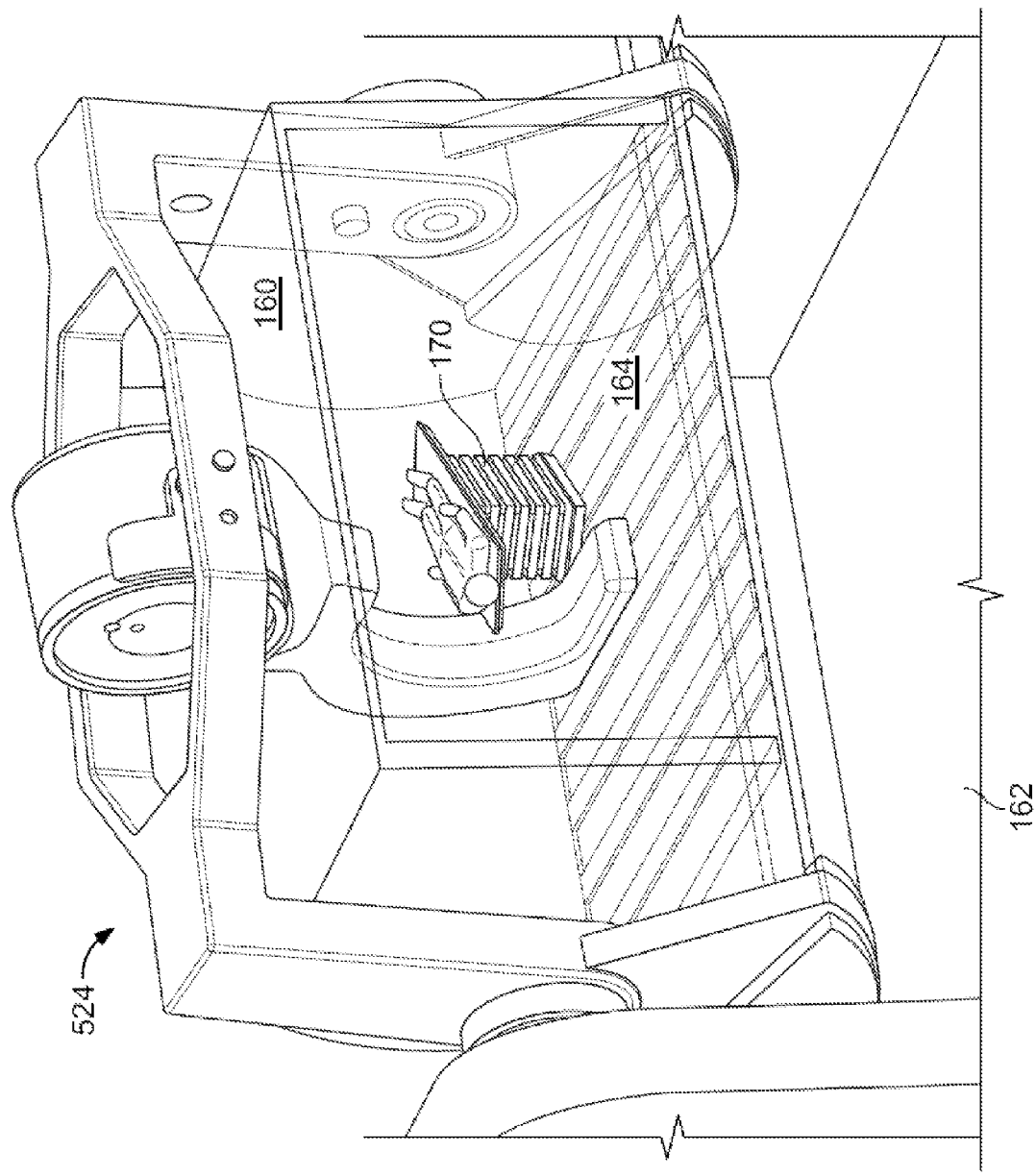
FIG. 12 is a perspective view of an example treatment room with a vault.

As shown in FIGS. 1, 11, and 12, the gantry bearings are supported by the walls of a cyclotron vault 524. The gantry enables the cyclotron to be swung through a range 520 of 180 degrees (or more) including positions above, to the side of, and below the patient. The vault is tall enough to clear the gantry at the top and bottom extremes of its motion. A maze 146 sided by walls 148, 150 provides an entry and exit route for therapists and patients. Because at least one wall 152 is not in line with the proton beam directly from the cyclotron, it can be made relatively thin and still perform its shielding function. The other three side walls 154, 156, 150/148 of the room, which may need to be more heavily shielded, can be buried within an earthen hill (not shown). The required thickness of walls 154, 156, and 158 can be reduced, because the earth can itself provide some of the needed shielding.

Figure 13:
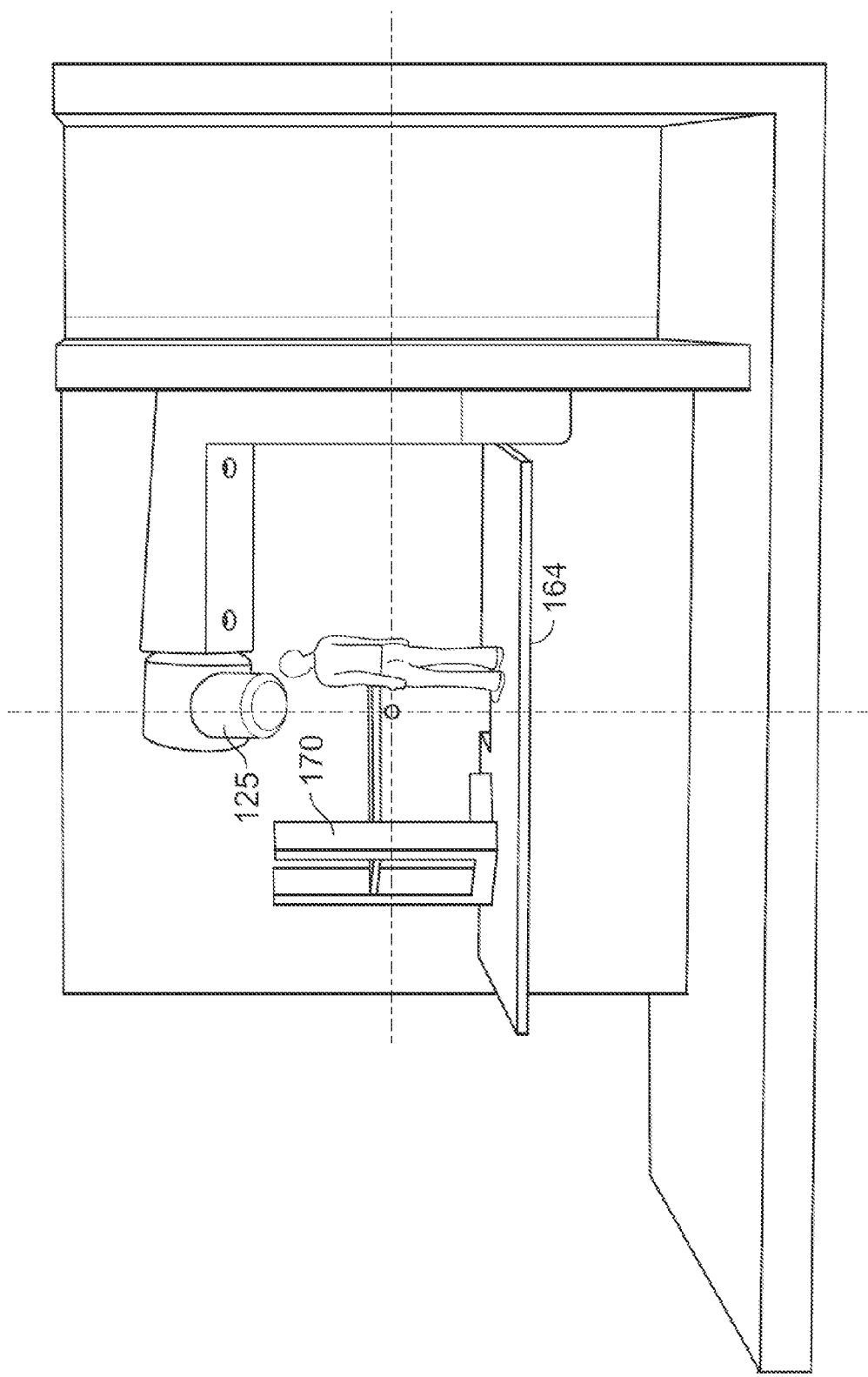
FIG. 13 shows a patient positioned next to an example particle accelerator.

Referring to FIGS. 12 and 13, for safety and aesthetic reasons, a therapy room 160 may be constructed within the vault. The therapy room is cantilevered from walls 154, 156, 150 and the base 162 of the containing room into the space between the gantry legs in a manner that clears the swinging gantry and also maximizes the extent of the floor space 164 of the therapy room. Periodic servicing of the accelerator can be accomplished in the space below the raised floor. When the accelerator is rotated to the down position on the gantry, full access to the accelerator is possible in a space separate from the treatment area. Power supplies, cooling equipment, vacuum pumps and other support equipment can be located under the raised floor in this separate space. Within the treatment room, the patient support 170 can be mounted in a variety of ways that permit the support to be raised and lowered and the patient to be rotated and moved to a variety of positions and orientations.

Figure 14:
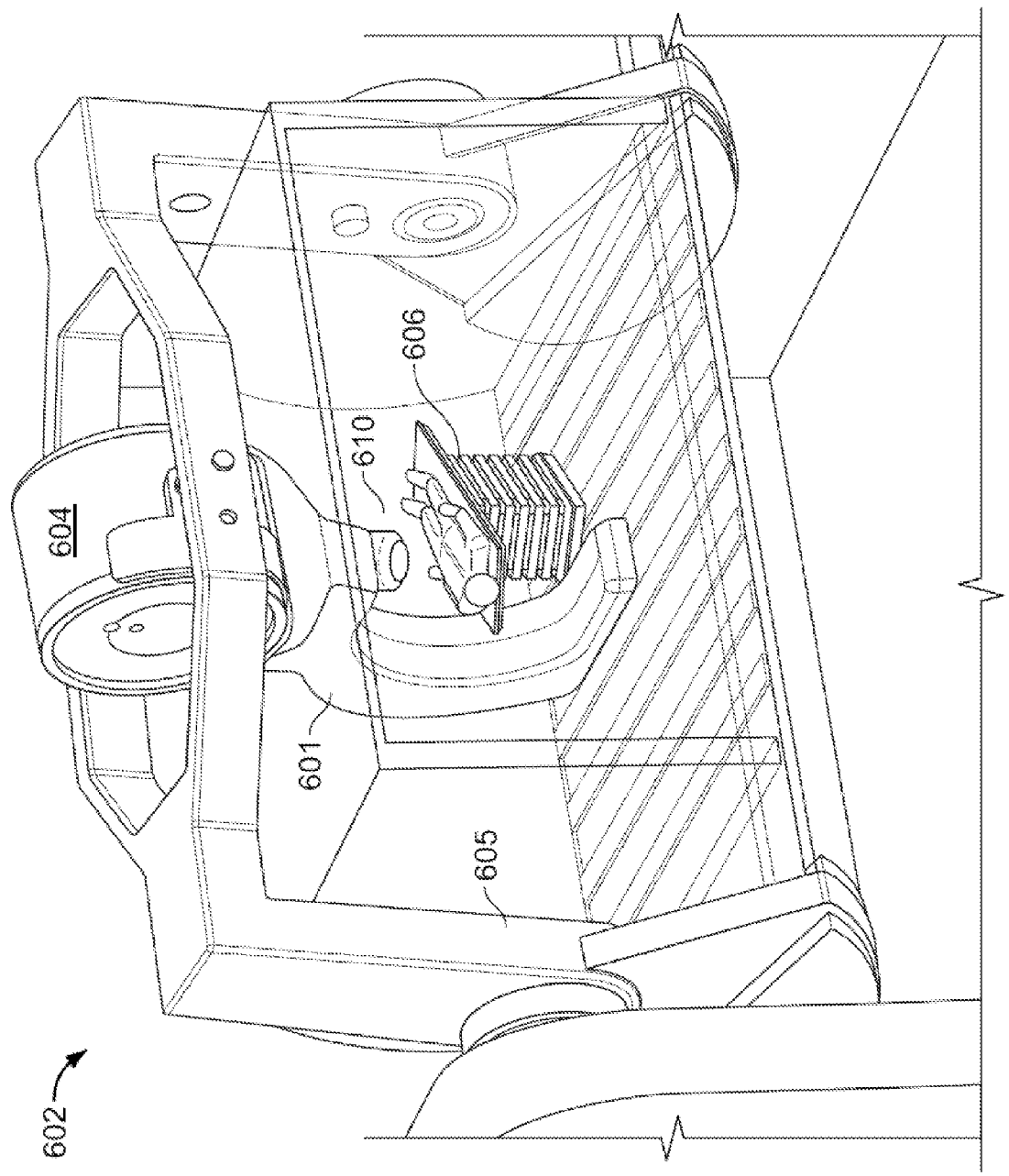
FIG. 14 shows a patient positioned within an example inner gantry in a treatment room.

In system 602 of FIG. 14, a beam-producing particle accelerator of the type described herein, in this case synchrocyclotron 604, is mounted on rotating gantry 605. Rotating gantry 605 is of the type described herein, and can angularly rotate around patient support 606. This feature enables synchrocyclotron 604 to provide a particle beam directly to the patient from various angles. For example, as in FIG. 14, if synchrocyclotron 604 is above patient support 606, the particle beam may be directed downwards toward the patient. Alternatively, if synchrocyclotron 604 is below patient support 606, the particle beam may be directed upwards toward the patient. The particle beam is applied directly to the patient in the sense that an intermediary beam routing mechanism is not required. A routing mechanism, in this context, is different from a shaping or sizing mechanism in that a shaping or sizing mechanism does not re-route the beam, but rather sizes and/or shapes the beam while maintaining the same general trajectory of the beam.

Further details regarding an example implementation of the foregoing system may be found in U.S. Pat. No. 7,728,311, filed on Nov. 16, 2006 and entitled "Charged Particle Radiation Therapy", and in U.S. patent application Ser. No. 12/275,103, filed on Nov. 20, 2008 and entitled "Inner Gantry". The contents of U.S. Pat. No. 7,728,311 and in U.S. patent application Ser. No. 12/275,103 are hereby incorporated by reference into this disclosure. In some implementations, the synchrocyclotron may be a variable-energy device, such as that described in U.S. patent application Ser. No. 13/916,401, filed on Jun. 12, 2013, the contents of which are incorporated herein by reference.

Example Implementations

As explained above, superconducting coils of a superconducting magnet are typically cooled to low temperatures to realize their superconducting properties. In some implementations, the superconducting coils are maintained at temperatures near absolute zero (e.g., about 4° Kelvin (K)) by enclosing a coil assembly (superconducting coils and a structure holding the coils) inside an evacuated annular aluminum or stainless steel cryostatic chamber that provides a free space around the coil structure, except at a limited set of support points.

Figure 15:
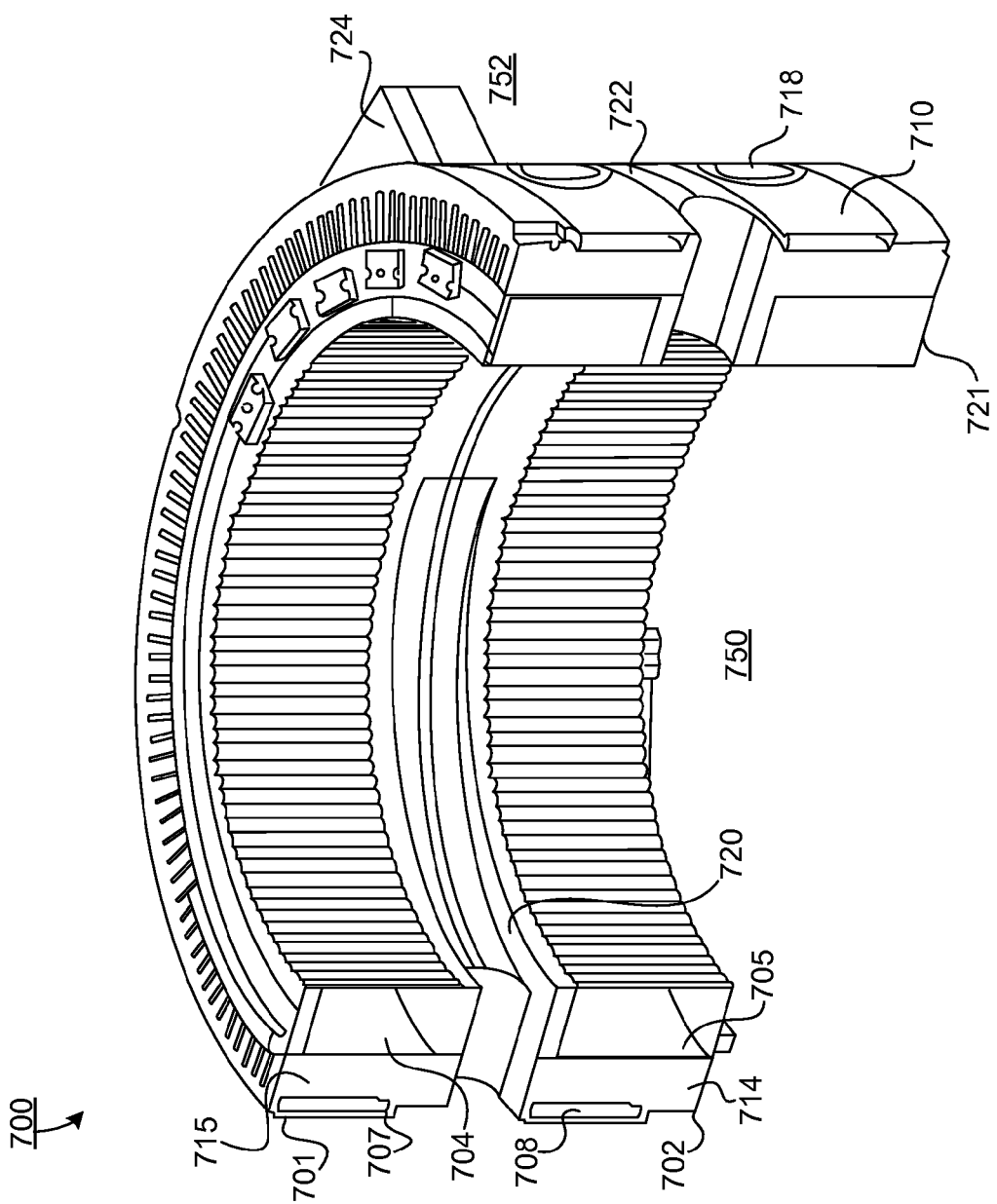
FIG. 15 is a perspective cut-away view of part of an example cold mass.
Figure 16:
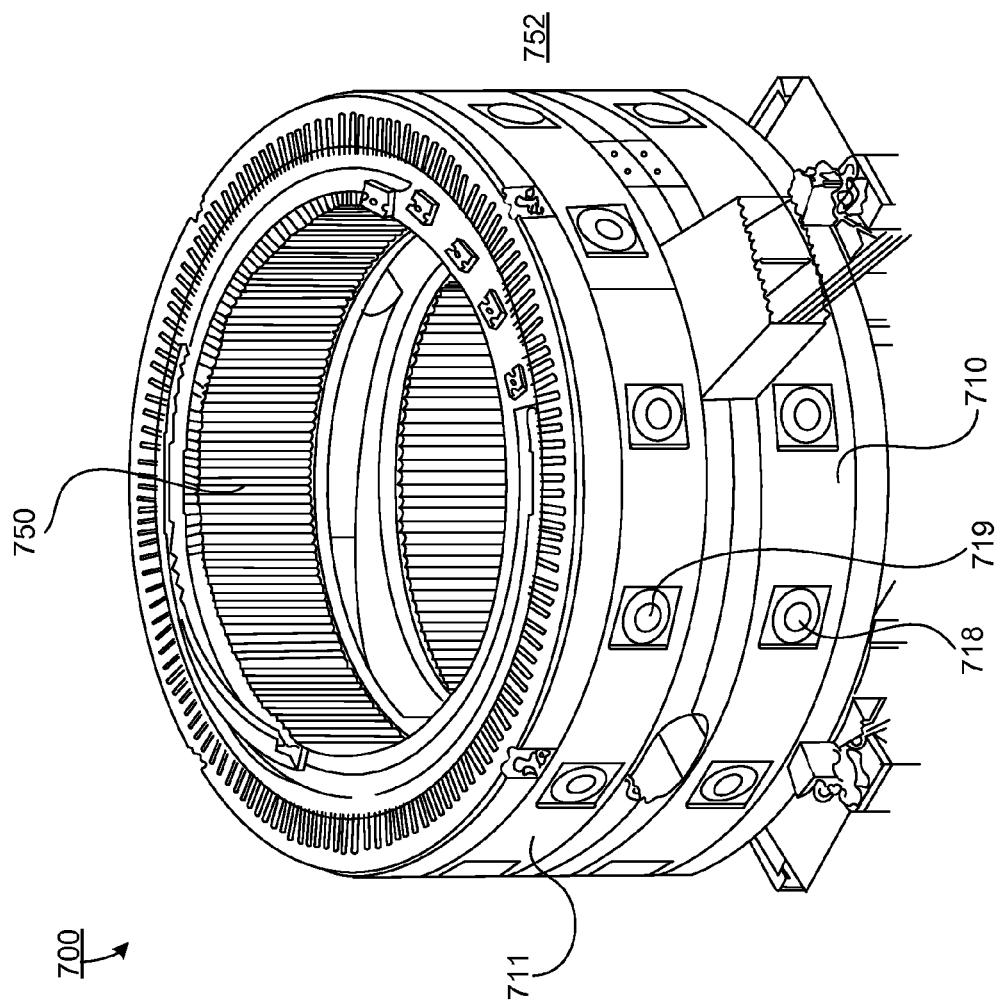
FIG. 16 is a perspective view of the cold mass.

A cross-section of a part of a superconducting magnet 700 that may be used in particle accelerator 700 is shown in FIG. 15. A perspective view of the same superconducting magnet is shown in FIG. 16. Superconducting magnet 700 includes structured halves 701, 702 (referred to as "bobbins"), that include coil chambers 704, 705, into which are placed pre-wound superconducting coils.

The assembly that includes the bobbin and the superconducting coil is part of a structure referred to as a "cold mass", since at least part of the assembly is maintained at low, e.g., superconducting, temperatures during operation. In an example implementation, the cold mass is a split superconducting solenoid coil pair supported in a structural stainless steel bobbin. A cooling turret is used to maintain the superconducting coil at appropriate temperature. In some implementations, the cooling turret includes a cryo-cooler condenser assembly (as described above), current leads, and a diode pack assembly. The cold mass is part of a cryostat, to which the turret is assembled to form the superconducting magnet. The cold mass may be suspended inside the yokes by support straps.

In the example implementation of FIGS. 15 and 16, a cooling chamber 707, 708 runs along an exterior circumference of each corresponding bobbin 701, 702. Cooling chamber 707, 708 may be machined into the structure of the corresponding bobbin and enclosed (e.g., made liquid-tight) via a stainless steel plate 710, 711 (shown for bobbin 702 only in FIG. 15). Stainless steel is, generally, a poor conductor of heat, although it may conduct some heat. Liquid helium may be used as coolant in some implementations. As such, each cooling chamber may be filled with liquid helium. Other liquid and/or gaseous coolants, however, may be used, even though the implementations described herein use liquid helium.

In each bobbin, a coil chamber 704, 705 holds a pre-wound superconducting coil. In some implementations, a superconducting coil is not wound around the bobbin, but rather is simply placed in a corresponding coil chamber. The coil may be held in place via support structures. The liquid helium and each corresponding superconducting coil remain separated in different chambers (e.g., in cooling chamber 707, 708 and coil chamber 704, 705, respectively). As a result, there is no direct physical contact between the superconducting coil and the coolant, e.g., the liquid helium. Furthermore, since the body of the bobbin is stainless steel, there is little, if any, thermal contact between the superconducting coils and the coolant via the body (e.g., 714, 715) of each bobbin. Accordingly, thermally-conductive structures are introduced, which contact both the superconducting coil and the liquid helium, and which are used to transfer heat between the two and thereby cool the superconducting coil.

As shown, the structure of each coil chamber 704, 705 is substantially circular. Accordingly, when placed in a coil chamber, a superconducting coil assumes this substantially circular configuration. If a superconducting coil deviates from this circular configuration, magnetic forces can affect the operation of the particle accelerator or cause damage to the coil. For example; during operation of the superconducting magnet, a hoop force may cause the superconducting coil to expand outwardly, thereby forcing the superconducting coil against the outer inside wall of the coil chamber. If the superconducting coil deviates enough from a circular configuration, this hoop force can cause the coil to tear.

Each superconducting coil generates a magnetic field that is stronger in an interior region of the circular configuration than in an exterior region of the circular configuration. For example, the magnetic field within region 750 enclosed by the superconducting coil is stronger than the magnetic field in a region 752, which is outside the area enclosed by the superconducting coil. In some implementations, the magnetic field in the interior region may be ten times as strong as the magnetic field in the exterior regions; however, this is not the case in all implementations. The magnetic field trails-off at distances from both the interior and the exterior regions of the superconducting coil.

Figure 17:
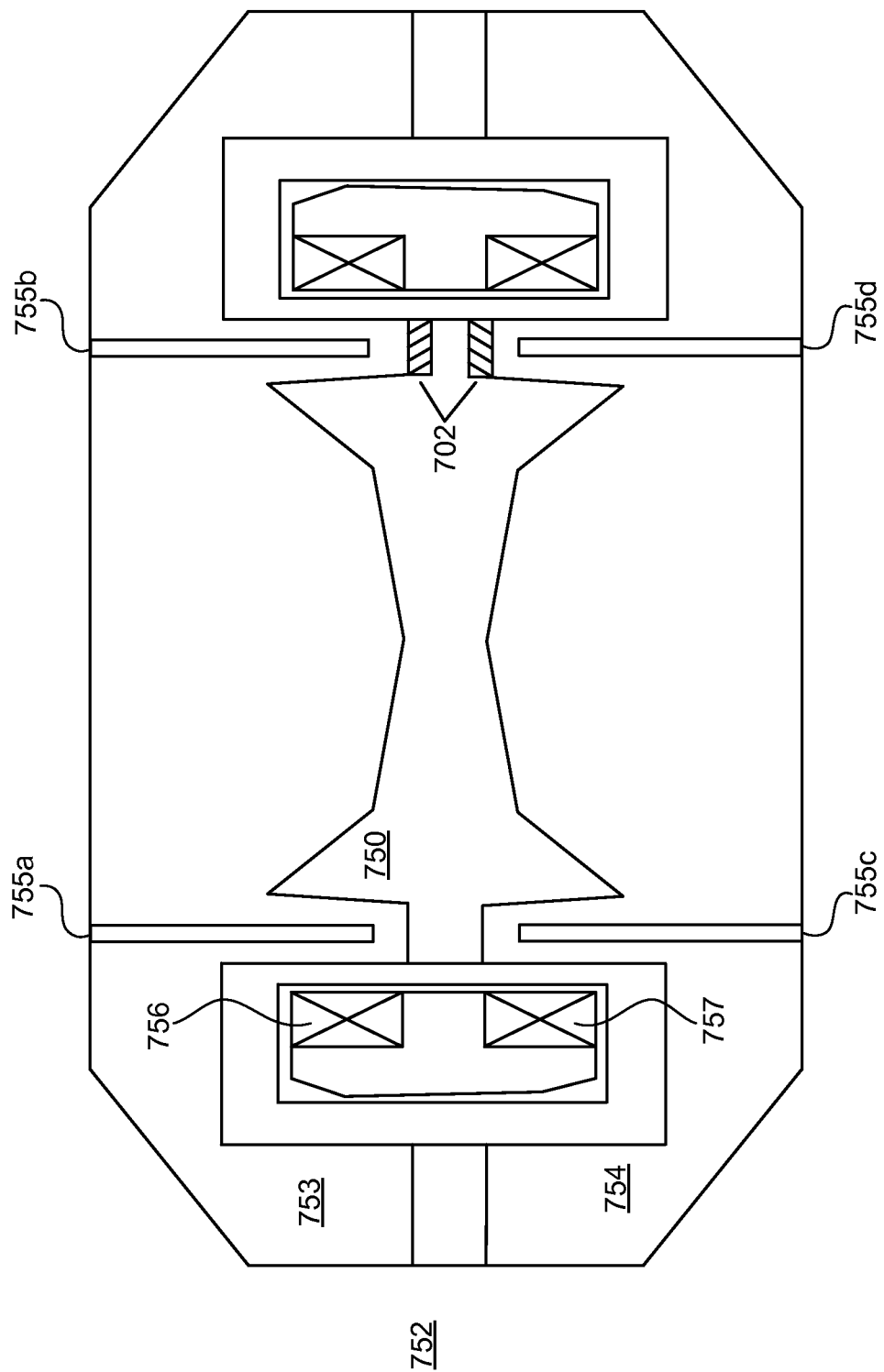
FIG. 17 is a cut-away view of an example yoke and acceleration cavity.

Referring to FIG. 17, one or more magnetic shims may be introduced into slots 755a, 755b, 755c, 755d of yokes 753, 754 in order to affect the magnetic field, and thus the magnetic force, exerted on the superconducting coils by the yokes. In some implementations, the magnetic shims are introduced into slots in the interior region 750 of the superconducting coil, although this is not a requirement. Because the magnetic force is greater in the interior region than in the exterior region, smaller and/or fewer magnetic shims may be used in the interior region to produce the same force that would be produced by larger and/or greater numbers of magnetic shims located in the exterior region. In other implementations, one or more of the magnetic shims may be in the interior region and/or one or more of the magnetic shims may be in the exterior region. In some implementations, the magnetic shims may simply be closer to the interior region than to the exterior region, or vice versa.

In this implementation, each yoke contains one or more slots proximate to a corresponding superconducting coil. For example, slot 755a is near to coil 756; slot 755c is near to coil 757 and so forth. The number and size of the slots and the magnetic shims varies from system-to-system depending on various factors, such as the magnetic field generated by the superconducting magnet.

Figure 18:
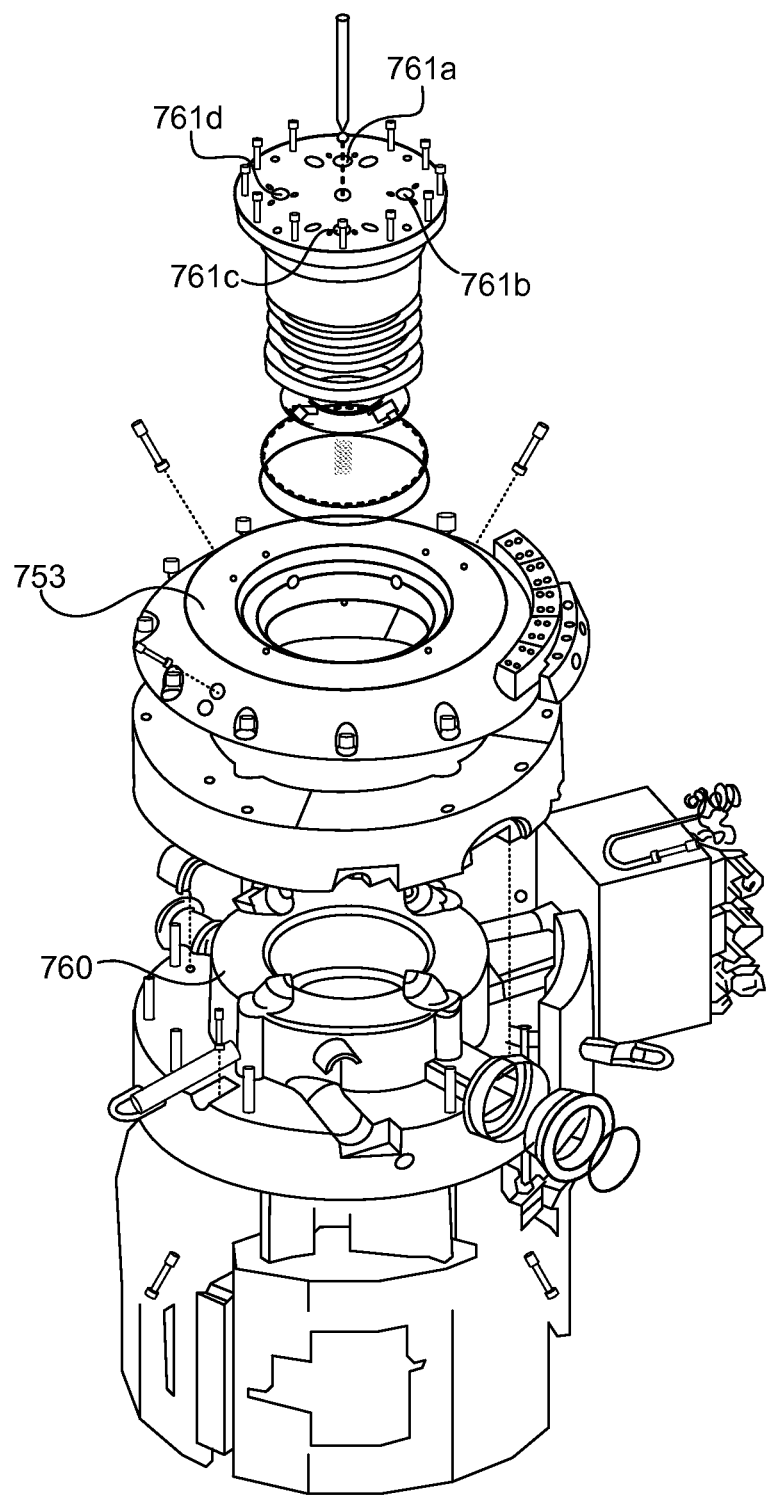
FIG. 18 is an exploded perspective view of a portion of an example superconducting magnet.

FIG. 18 shows an exploded perspective view of a portion of a superconducting magnet, which includes yoke 753 and the cold mass 760. Slots 761a, 761b, 761c and 761d show where four magnetic shims of the type described above may be introduced into top yoke 753 (the yoke in the figure). A corresponding configuration may be present for the bottom yoke (not shown).

Figure 19:
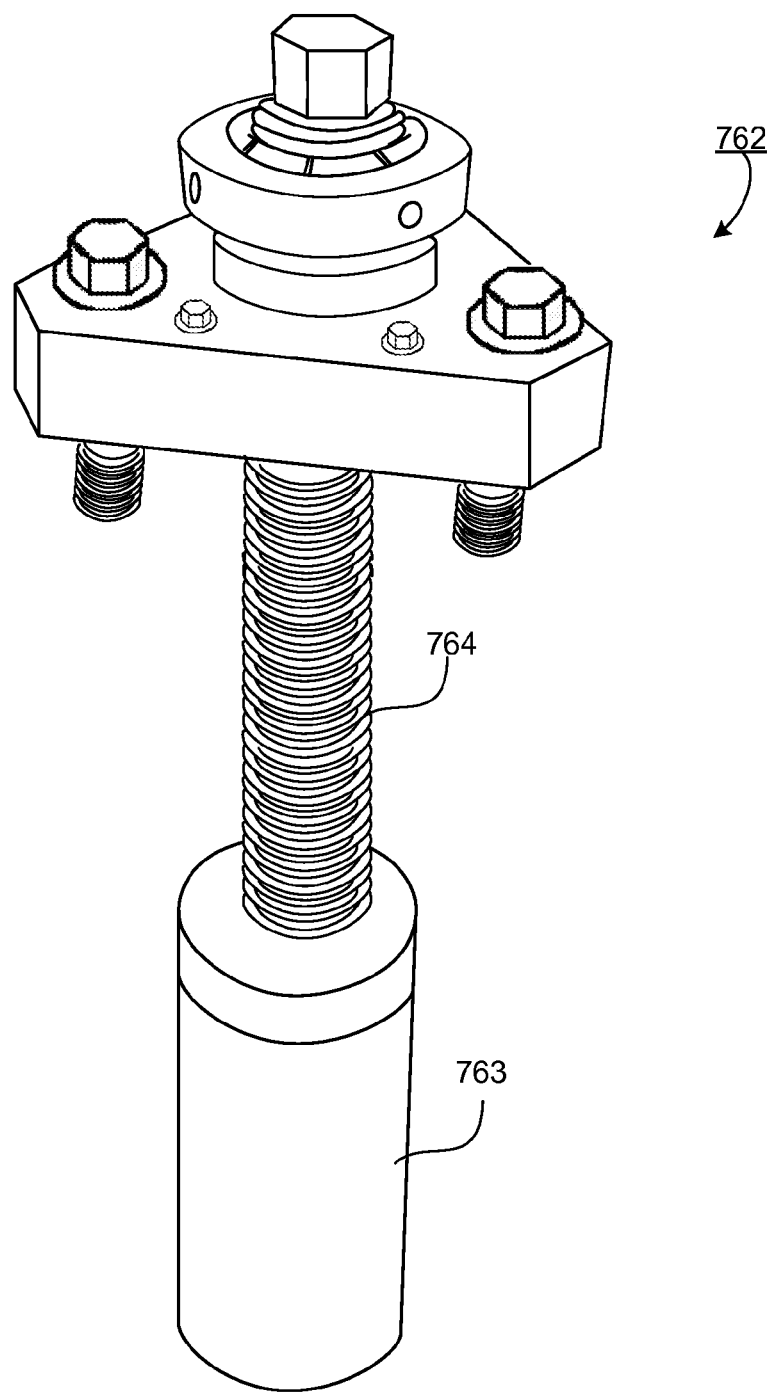
FIGS. 19 and 20 are perspective views of examples of different types of magnetic shims.

In some implementations, the magnetic shims are implemented using iron or steel magnetic shims, such as magnetic shim 762 shown in FIG. 19. Magnetic shim 762 may be in the shape of a rod (or plunger) or may have other appropriate shapes. A magnetic shim may be placed in a slot of the yoke near to a corresponding superconducting coil. Moving the magnetic shim downward, further inside the yoke increases the amount of ferromagnetic material near to the superconducting coil and thereby increases the amount of magnetic force exerted on the corresponding superconducting coil. By contrast, moving the magnetic shim upward and out of the yoke decreases the amount of ferromagnetic material near to the superconducting coil and thereby decreases the amount of magnetic force exerted on the corresponding superconducting coil.

Figure 20:
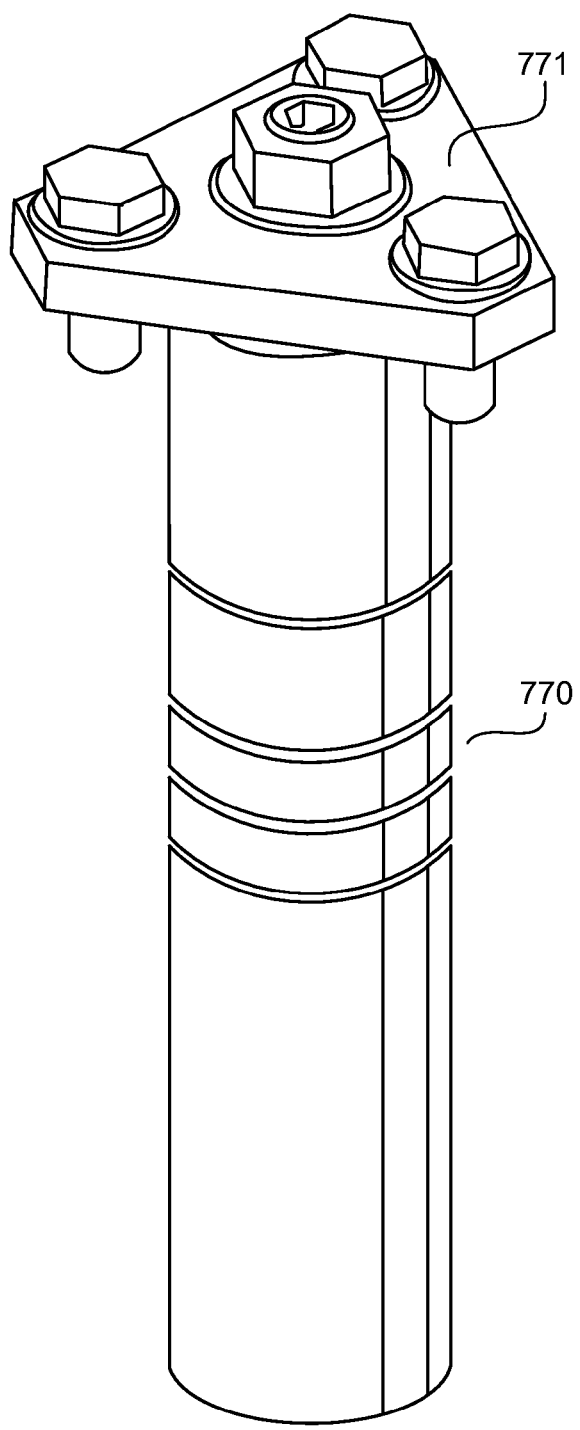

In the example of FIG. 19, magnetic shim 762 includes a rod like portion inside of enclosure 763. That portion may be moved into, or out of, the yoke using screw 764. Cap 765 may affix magnetic shim 762 to the yoke. FIG. 20 shows a magnetic shim 770, which may be permanently fixed in a slot, and held in place via cap 771. For example, magnetic shim 770 may be machined to a particular size, introduced into a slot, and fixed, without the possibility of further adjustment.

Figure 21:
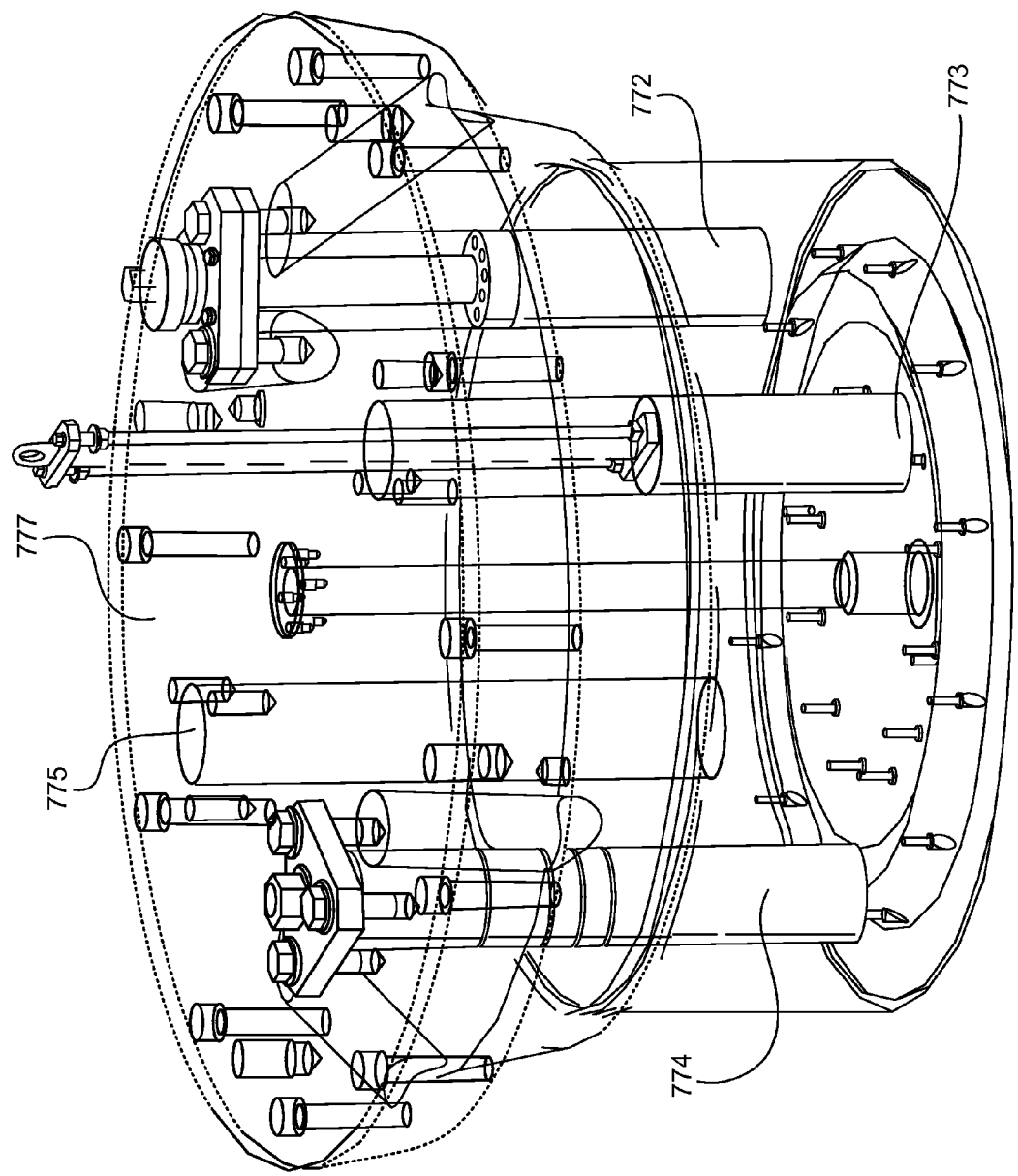
FIG. 21 is a perspective see-through view of magnetic shims incorporated into a yoke of a superconducting magnet.

FIG. 20 shows magnetic shims introduced into a cap 777 of a yoke. Shim 772 is of the type shown in FIG. 19, and shim 774 is of the type shown in FIG. 20. Shim 773 is part-way installed, but does not yet include a cap, nor is it yet fixed to the yoke. Slot 775 does not yet include a shim. It is noted that a yoke may contain all of the same type of magnetic shim, or different types may be used in the same yoke (as shown in FIG. 21). Also, not all slots require a shim.

Movement or the magnetic shim(s) may be computer-controlled through a control system that is part of the particle therapy system. For example, the movement of magnetic shim 773 may be controlled based on a rotational position of the particle accelerator (and, thus, a rotational position of the electromagnet inside the accelerator), as measured by the rotation position of the gantry on which the particle accelerator is mounted. The various parameters used to set the magnetic shim location vis-à-vis the rotational position of the accelerator may be measured empirically, and programmed into the control system computer. One or more computer-controlled actuators may be used to implement actual movement of the magnetic shim(s).

In some implementations, movement of the magnetic shim(s) may be controlled in real-time. In other implementations, optimal positions of the magnetic shim(s) may be determined through testing, and the magnetic shims may be permanently inserted into the slots in the yokes at appropriate depths. In some implementations, there may be eight slots/magnetic shims (four per yoke half). In other implementations, different numbers of slots/magnetic shims may be used. FIG. 21 shows an example in which four magnetic shims may be introduced into the corresponding yoke. In this example, a similar magnetic shim configuration is provided for the other yoke (not shown).

In some implementations, the magnetic shim(s) (e.g., the magnetic shim(s) described above) may instead be, or include, one or more miniature electromagnets, the current through which is controlled to affect the magnetic field produced by the regenerator in the manner described above. The current through the one or more elecrtomagnets may be computer-controlled through a control system that is part of the particle therapy system. For example, the current may be controlled based on a rotational position of the particle accelerator, as measured by the rotation position of the gantry on which the particle accelerator is mounted. The various parameters used to set the current vis-à-vis the rotational position of the accelerator may be measured empirically, and programmed into the control system computer.

Referring back to FIG. 17, as explained above, in some implementations, magnetic may be introduced into slots in interior region 750 of the superconducting coil for the purpose of adjusting the location of the superconducting coil. In some implementations, magnetic shims of the type described herein, although possibly magnetic shims that have a smaller size, may be introduced into interior region 750 in order to affect the energies of particle orbits within region 750. More specifically, as explained above, a magnetic field regenerator is positioned in the cavity (region 750) to adjust the existing magnetic field inside the cavity to thereby change locations of successive orbits of the particles accelerated from the plasma column so that, eventually, the particles output to an extraction channel contained in the yokes. The regenerator may increase the magnetic field at an area of the cavity, thereby causing each successive orbit of particles at that area to precess outward toward the entry point of the extraction channel, eventually reaching the extraction channel. The extraction channel receives particles accelerated from the plasma column and outputs the received particles from the cavity.

In some cases, as the superconducting coil moves during rotation, orbits that are affected by regenerator 702 change due to gravitational movement of the coil. This movement can be as little as tenths of millimeters. Nevertheless, as a result, the energy of the particle beam that enters the extraction channel may be different from the energy required to traverse the entire channel. To adjust for this change in the energy of particles entering the extraction channel, in some cases, a structure is placed inside, or at the entry point to, the extraction channel. The structure may be used to absorb excess energy in the particle beam. However, the structure can change the spots size of the resulting beam. In implementations of the particle therapy system that employ scanning to scan the particle beam across an irradiation target, changes to the particle beam spot size can be undesirable.

Accordingly, magnetic shims, examples of which are described herein, may be employed to eliminate the use of a structure inside, or at the entry point to, the extraction channel to absorb excess energy of the particle beam. For example, magnetic shims may be introduced into region 750 to change the magnetic field inside region 750 and thereby change the orbits of particles in region 750 so that the energy of the particles that reach the entrance to extraction channel (which interfaces to region 750) closely match the energy required to traverse the extraction channel. As a result of appropriate positioning of magnetic shims, an energy absorber is not required at the extraction channel to absorb energy from the particle beam and thereby affect the size of the particle beam spot.

More specifically, absent use of the magnetic shims or an absorbing structure, some particles entering the extraction channel may have an energy that exceeds that needed to traverse the extraction channel. As a result, such particles may hit the walls of the extraction channel or other structures during traversal, thereby preventing their output. In other cases, some particles may not have sufficient energy to reach the extraction channel, thereby also preventing their output. The magnetic shims described herein may be used to shape the magnetic field at one or more locations within region 750 so as to perturb the particle orbits at a particular energy level(s) so that the particles at that energy level(s) that reach the extraction channel have sufficient energy to enter the extraction channel and to traverse the extraction channel for output.

In some implementations, the magnetic shims may be used to shape the magnetic field in the cavity without the use of a regenerator. For example, described above is the case where one or more magnetic shims are used in concert with the regenerator to shape the magnetic field in the cavity. In some implementations, the regenerator itself may be replaced with one or more magnetic shims of the type described herein. Accordingly, the entire magnetic field in the cavity may be shaped using magnetic shims, making the system customizable.

Magnetic shims in region 750 may be computer-controlled. One or more magnetic shim locations may be set beforehand so that they are positioned without change during operation of the synchrocyclotron. Alternatively, one or more magnetic shims may be controlled interactively during operation of the synchrocyclotron so as to shape the magnetic field within region 750 in real time. One or more magnetic shims may be used within region 750.

In implementations that employ an active return system, such as that described in U.S. patent application Ser. No. 13/907,601, the sizes and locations of the various magnetic shims will be different from those presented herein. The magnetic shims may be introduced via holes in appropriate magnetic pole pieces in a manner similar to how they are introduced in the magnetic yokes. If necessary, additional ferromagnetic structures may be used to control coil position in implementations that employ an active return system.

Any two more of the foregoing features may be used in an appropriate combination to adjust the positioning of a superconducting coil in an electromagnet.

Elements of different implementations described herein may be combined to form other implementations not specifically set forth above. Elements may be left out of the processes, systems, apparatus, etc., described herein without adversely affecting their operation. Various separate elements may be combined into one or more individual elements to perform the functions described herein.

The example implementations described herein are not limited to use with a particle therapy system or to use with the example particle therapy systems described herein. Rather, the example implementations can be used in any appropriate system that includes a superconducting coil.

Additional information concerning the design of an example implementation of a particle accelerator that may be used in a system as described herein can be found in U.S. Provisional Application No. 60/760,788, entitled "High-Field Superconducting Synchrocyclotron" and filed Jan. 20, 2006; U.S. patent application Ser. No. 11/463,402, entitled "Magnet Structure For Particle Acceleration" and filed Aug. 9, 2006; and U.S. Provisional Application No. 60/850,565, entitled "Cryogenic Vacuum Break Pneumatic Thermal Coupler" and filed Oct. 10, 2006, all of which are incorporated herein by reference.

The following applications are incorporated by reference into the subject application: the U.S. Provisional Application entitled "CONTROLLING INTENSITY OF A PARTICLE BEAM" (Application No. 61/707,466), the U.S. Provisional Application entitled "ADJUSTING ENERGY OF A PARTICLE BEAM" (Application No. 61/707,515), the U.S. Provisional Application entitled "ADJUSTING COIL POSITION" (Application No. 61/707,548), the U.S. Provisional Application entitled "FOCUSING A PARTICLE BEAM USING MAGNETIC FIELD FLUTTER" (Application No. 61/707,572), the U.S. Provisional Application entitled "MAGNETIC FIELD REGENERATOR" (Application No. 61/707,590), the U.S. Provisional Application entitled "FOCUSING A PARTICLE BEAM" (Application No. 61/707,704), the U.S. Provisional Application entitled "CONTROLLING PARTICLE THERAPY (Application No. 61/707,624), and the U.S. Provisional Application entitled "CONTROL SYSTEM FOR A PARTICLE ACCELERATOR" (Application No. 61/707,645).

The following are also incorporated by reference into the subject application: U.S. Pat. No. 7,728,311 which issued on Jun. 1, 2010, U.S. patent application Ser. No. 11/948,359 which was filed on Nov. 30, 2007, U.S. patent application Ser. No. 12/275,103 which was filed on Nov. 20, 2008, U.S. patent application Ser. No. 11/948,662 which was filed on Nov. 30, 2007, U.S. Provisional Application No. 60/991,454 which was filed on Nov. 30, 2007, U.S. Pat. No. 8,003,964 which issued on Aug. 23, 2011, U.S. Pat. No. 7,208,748 which issued on Apr. 24, 2007, U.S. Pat. No. 7,402,963 which issued on Jul. 22, 2008, U.S. patent application Ser. No. 13/148,000 filed Feb. 9, 2010, U.S. patent application Ser. No. 11/937,573 filed on Nov. 9, 2007, U.S. patent application Ser. No. 11/187,633, titled "A Programmable Radio Frequency Waveform Generator for a Synchrocyclotron," filed Jul. 21, 2005, U.S. Provisional Application No. 60/590,089, filed on Jul. 21, 2004, U.S. patent application Ser. No. 10/949,734, titled "A Programmable Particle Scatterer for Radiation Therapy Beam Formation", filed Sep. 24, 2004, and U.S. Provisional Application No. 60/590,088, filed Jul. 21, 2005.

Any features of the subject application may be combined with one or more appropriate features of the following: the U.S. Provisional Application entitled "CONTROLLING INTENSITY OF A PARTICLE BEAM" (Application No. 61/707,466), the U.S. Provisional Application entitled "ADJUSTING ENERGY OF A PARTICLE BEAM" (Application No. 61/707,515), the U.S. Provisional Application entitled "ADJUSTING COIL POSITION" (Application No. 61/707,548), the U.S. Provisional Application entitled "FOCUSING A PARTICLE BEAM USING MAGNETIC FIELD FLUTTER" (Application No. 61/707,572), the U.S. Provisional Application entitled "MAGNETIC FIELD REGENERATOR" (Application No. 61/707,590), the U.S. Provisional Application entitled "FOCUSING A PARTICLE BEAM" (Application No. 61/707,704), the U.S. Provisional Application entitled "CONTROLLING PARTICLE THERAPY (Application No. 61/707,624), and the U.S. Provisional Application entitled "CONTROL SYSTEM FOR A PARTICLE ACCELERATOR" (Application No. 61/707,645), U.S. Pat. No. 7,728,311 which issued on Jun. 1, 2010, U.S. patent application Ser. No. 11/948,359 which was filed on Nov. 30, 2007, U.S. patent application Ser. No. 12/275,103 which was filed on Nov. 20, 2008, U.S. patent application Ser. No. 11/948,662 which was filed on Nov. 30, 2007, U.S. Provisional Application No. 60/991,454 which was filed on Nov. 30, 2007, U.S. patent application Ser. No. 13/907,601, which was filed on May 31, 2013, U.S. patent application Ser. No. 13/916,401, filed on Jun. 12, 2013, U.S. Pat. No. 8,003,964 which issued on Aug. 23, 2011, U.S. Pat. No. 7,208,748 which issued on Apr. 24, 2007, U.S. Pat. No. 7,402,963 which issued on Jul. 22, 2008, U.S. patent application Ser. No. 13/148,000 filed Feb. 9, 2010, U.S. patent application Ser. No. 11/937,573 filed on Nov. 9, 2007, U.S. patent application Ser. No. 11/187,633, titled "A Programmable Radio Frequency Waveform Generator for a Synchrocyclotron," filed Jul. 21, 2005, U.S. Provisional Application No. 60/590,089, filed on Jul. 21, 2004, U.S. patent application Ser. No. 10/949,734, titled "A Programmable Particle Scatterer for Radiation Therapy Beam Formation", filed Sep. 24, 2004, and U.S. Provisional Application No. 60/590,088, filed Jul. 21, 2005.

Except for the provisional application from which this patent application claims priority and the documents incorporated by reference above, no other documents are incorporated by reference into this patent application.

Other implementations not specifically described herein are also within the scope of the following claims.

What is claimed is:

1. A particle accelerator comprising:
   a coil to provide a magnetic field to a cavity;
   a cryostat comprising a chamber for holding the coil, the coil being in the chamber to define an interior region of the coil and an exterior region of the coil;
   magnetic structures adjacent to the cryostat, the magnetic structures having one or more slots at least part-way therethrough; and
   one or more magnetic shims in one or more corresponding slots, the one or more magnetic shims being movable to change a magnetic field produced via the magnetic structures and thereby adjust a position of the coil.

2. The particle accelerator of claim 1, wherein the one or more magnetic shims are controllable to move into or out of corresponding slots.

3. The particle accelerator of claim 2, wherein the one or more magnetic shims are computer controlled.

4. The particle accelerator of claim 2, wherein the one or more magnetic shims are controllable in response to rotation of the particle accelerator.

5. The particle accelerator of claim 4, wherein the one or more magnetic shims are controllable to adjust the position of the coil to compensate for motion of the coil caused by rotation of the particle accelerator.

6. The particle accelerator of claim 1, wherein at least one of the magnetic shims is within the interior region.

7. The particle accelerator of claim 6, wherein all of the magnetic shims are within the interior region.

8. The particle accelerator of claim 1, wherein the one or more magnetic shims comprise ferromagnetic material.

9. A proton therapy system comprising:
   the particle accelerator of claim 1; and
   a gantry on which the particle accelerator is mounted, the gantry being rotatable relative to a patient position;
   wherein the particle accelerator is configured to output protons to the patient position.

10. The proton therapy system of claim 9, wherein the particle accelerator is rotatable relative to a fixed position; and
   wherein the proton therapy system further comprises a control system to control movement of the one or more magnetic shims based on a rotational position of the gantry.

11. An electromagnet comprising:
   a superconducting coil in a substantially circular configuration to generate a magnetic field;
   magnetic structures adjacent to the superconducting coil, the magnetic structures having one or more slots at least part-way therethrough; and
   one or more magnetic shims in one or more corresponding slots, the one or more magnetic shims being movable to change a magnetic field produced via the magnetic structures and thereby adjust a position of the superconducting coil.

12. The electromagnet of claim 11, wherein the superconducting coil is configured to generate a magnetic field that is stronger in an interior of the circular configuration than in an exterior of the circular configuration; and
   wherein the one or more magnetic shims are closer to the interior of the circular configuration than to the exterior of the circular configuration.

13. The electromagnet of claim 12, wherein at least part of the one or more magnetic shims are within the interior of the circular configuration.

14. The electromagnet of claim 11, wherein all of the one or more magnetic shims are within the interior of the circular configuration.

15. The electromagnet of claim 11, wherein the one or more magnetic shims are controllable to move into or out of corresponding slots.

16. The electromagnet of claim 15, wherein the one or more magnetic shims are computer controlled.

17. The electromagnet of claim 15, wherein the one or more magnetic shims are controllable in response to rotation of the electromagnet.

18. The electromagnet of claim 17, wherein the one or more magnetic shims are controllable to adjust the position of the coil to compensate for motion of the coil caused by rotation of the electromagnet.

19. The particle accelerator of claim 11, wherein the one or more magnetic shims comprise one or more magnetic shims comprised of ferromagnetic material.

20. A proton therapy system comprising:
   a particle accelerator comprising the electromagnet of claim 11 for outputting particles comprising protons; and
   a gantry on which the particle accelerator is mounted, the gantry being rotatable relative to a patient position;

wherein the particle accelerator is configured to output protons to the patient position.

21. The proton therapy system of claim 20, wherein the particle accelerator is rotatable relative to a fixed position; and
wherein the proton therapy system further comprises a control system to control movement of the one or more magnetic shims based on a rotational position of the gantry.

22. A method of adjusting a position of a superconducting coil in an electromagnet, the method comprising:
determining a rotational position associated with the electromagnet; and
based on the rotational position, controlling a position of one or more magnetic shims in a magnetic structure proximate to the superconducting coil to change a magnetic field produced via the magnetic structure and thereby adjust a position of the superconducting coil.

23. The method of claim 22, wherein the electromagnet is part of a particle accelerator that is mounted on a gantry that is rotatable; and
wherein the rotational position is a position of the gantry.

24. The method of claim 22, wherein the superconducting coil is in a substantially circular configuration to generate a magnetic field;
wherein the magnetic field is stronger in an interior of the circular configuration than in an exterior of the circular configuration; and
wherein the one or more magnetic shims are closer to the interior of the circular configuration than to the exterior of the circular configuration.

25. The method of claim 24, wherein at least part of the one or more magnetic shims are within the interior of the circular configuration.

26. The method of claim 24, wherein all of the one or more magnetic shims are within the interior of the circular configuration.

27. The method of claim 22, wherein the one or more magnetic shims are controllable to move into or out of corresponding slots in the magnetic structure.

28. The method of claim 22, wherein the position of the one or more magnetic shims are controllable using a computer.

29. The method of claim 22, wherein the one or more magnetic shims are controllable to adjust the position of the superconducting coil to compensate for motion of the superconducting coil caused by rotation of the electromagnet.

30. The method of claim 22, wherein the one or more magnetic shims comprise one or more magnetic shims comprised of ferromagnetic material.

31. A particle accelerator comprising:
a coil to provide a magnetic field to a cavity in which particles are accelerated;
a cryostat comprising a chamber for holding the coil;
magnetic structures adjacent to the cryostat, the magnetic structures having one or more slots at least part-way therethrough; and
magnetic shims in corresponding slots, the magnetic shims being movable to adjust a magnetic field in the cavity in order to affect a particle orbit within the cavity and a position of the coil.

32. The particle accelerator of claim 31, further comprising:
an extraction channel, through which the particles pass for output from the particle accelerator, the extraction channel having an entrance at the cavity;
wherein one or more magnetic shims are movable in one or more corresponding slots so that an energy of particles entering the extraction channel from the cavity matches an energy required for the particles to traverse the extraction channel.

33. The particle accelerator of claim 32, wherein the entrance to the extraction channel does not include an energy absorbing structure through which a particle beam passes prior to entry to the extraction channel.

34. The particle accelerator of claim 31, wherein the magnetic structures comprise pole pieces and wherein the coil is a first coil; and
wherein the particle accelerator further comprises a second coil to operate as an active return for magnetic field resulting from current through the first coil.

35. A proton therapy system comprising:
the particle accelerator of claim 31; and
a gantry on which the particle accelerator is mounted, the gantry being rotatable relative to a patient position;
wherein the particle accelerator is configured to output protons to the patient position.

* * * * *